(12) United States Patent
Nishikawa et al.

(10) Patent No.: US 12,240,903 B2
(45) Date of Patent: Mar. 4, 2025

(54) BIOMARKERS FOR DETERMINING THE EFFECTIVENESS OF IMMUNE CHECKPOINT INHIBITORS

(71) Applicants: ONO PHARMACEUTICAL CO., LTD., Osaka (JP); NATIONAL CANCER CENTER, Tokyo (JP)

(72) Inventors: Hiroyoshi Nishikawa, Chiba (JP); Yosuke Togashi, Chiba (JP); Yukiya Ohyama, Osaka (JP); Takao Yoshida, Osaka (JP); Kazuhiko Takeda, Osaka (JP); Kenichi Koda, Osaka (JP); Atsushi Honda, Osaka (JP); Atsushi Oyagi, Osaka (JP); Toru Kakinuma, Osaka (JP); Masayuki Murata, Osaka (JP)

(73) Assignees: ONO PHARMACEUTICAL CO., LTD., Osaka (JP); NATIONAL CANCER CENTER, Tokyo (JP)

( * ) Notice: Subject to any disclaimer, the term of this patent is extended or adjusted under 35 U.S.C. 154(b) by 1069 days.

(21) Appl. No.: 17/058,794

(22) PCT Filed: May 30, 2019

(86) PCT No.: PCT/JP2019/021633
§ 371 (c)(1),
(2) Date: Nov. 25, 2020

(87) PCT Pub. No.: WO2019/230919
PCT Pub. Date: Dec. 5, 2019

(65) Prior Publication Data
US 2021/0198361 A1   Jul. 1, 2021

(30) Foreign Application Priority Data

May 31, 2018 (JP) .................................. 2018-105017
Oct. 4, 2018 (JP) .................................. 2018-189370

(51) Int. Cl.
C07K 16/28 (2006.01)
A61K 39/00 (2006.01)
A61P 35/00 (2006.01)
G01N 33/50 (2006.01)

(52) U.S. Cl.
CPC .......... *C07K 16/2818* (2013.01); *A61P 35/00* (2018.01); *G01N 33/505* (2013.01); *A61K 2039/507* (2013.01); *G01N 2800/52* (2013.01)

(58) Field of Classification Search
CPC ......................... G01N 33/505; G01N 2800/52
See application file for complete search history.

(56) References Cited

U.S. PATENT DOCUMENTS

| 2012/0282249 | A1 | 11/2012 | Fox et al. |
| 2014/0377251 | A1 | 12/2014 | Diluzio et al. |
| 2015/0202291 | A1 | 7/2015 | Bosch et al. |
| 2016/0340431 | A1 | 11/2016 | Fox et al. |
| 2016/0340432 | A1 | 11/2016 | Fox et al. |
| 2017/0002078 | A1 | 1/2017 | Fox et al. |
| 2018/0055882 | A1 | 3/2018 | Rosenblum et al. |
| 2018/0133313 | A1 | 5/2018 | Coric et al. |
| 2018/0207279 | A1 | 7/2018 | Fox et al. |
| 2018/0289811 | A1 | 10/2018 | Fox et al. |
| 2019/0076532 | A1 | 3/2019 | Diluzio et al. |
| 2019/0231878 | A1 | 8/2019 | Brown et al. |
| 2019/0247361 | A1 | 8/2019 | Loumaye et al. |
| 2019/0331682 | A1* | 10/2019 | Zitvogel ......... G01N 33/57492 |
| 2020/0206353 | A1 | 7/2020 | Fox et al. |
| 2021/0000953 | A1 | 1/2021 | Coric et al. |
| 2021/0052733 | A1 | 2/2021 | Diluzio et al. |
| 2022/0370617 | A1 | 11/2022 | Diluzio et al. |

FOREIGN PATENT DOCUMENTS

| CN | 106999590 A | 8/2017 |
| CN | 108129565 B | 9/2022 |
| CN | 109689048 B | 10/2022 |
| WO | 2014/194293 A1 | 12/2014 |

OTHER PUBLICATIONS

Zuo et al. Leukemia Res 70:56-61 (Year: 2018).*
Adil I. Daud et al., "Tumor immune profiling predicts response to anti-PD-1 therapy in human melanoma", The Journal of Clinical Investigation, vol. 126, No. 9, Sep. 2016, 7 pages total, XP055585410.
Michael A. Curran et al., "PD-1 and CTLA-4 combination blockade expands infiltrating T cells and reduces regulatory T and myeloid cells within B16 melanoma tumors", PNAS, vol. 107, No. 9, Mar. 2010, 6 pages total, XP055067204.
Sergio A. Quezada et al., "CTLA4 blockade and GM-CSF combination immunotherapy alters the intratumor balance of effector and regulatory T cells", The Journal of Clinical Investigation, vol. 116, No. 7, Jul. 2006, 11 pages total, XP002556462.
Communication dated Feb. 2, 2022 issued by the European Patent Office in counterpart European Application No. 19812634.4.
Office Action dated Jun. 29, 2022, issued by the Intellectual Property Office of Singapore in corresponding Singaporean Patent Application No. 11202011651S.

(Continued)

*Primary Examiner* — Jessica H Roark

(74) *Attorney, Agent, or Firm* — Sughrue Mion, PLLC

(57) ABSTRACT

A method for identifying a patient with malignant tumor on which the effect of an immune checkpoint inhibitor can be more expected, and agents for suppressing the progression of, suppressing the recurrence of, and/or treating malignant tumor, characterized by prescriptions based on identifying a patient with a malignant tumor on which the effect of an immune checkpoint inhibitor can be more expected, by analyzing evaluation items including combinations such as the PD-1 expression intensity, the percentage of the number of PD-1 expressing cells and the like in Treg cells and CD8+ T cells in tumor tissue or blood.

19 Claims, 23 Drawing Sheets

(56) References Cited

OTHER PUBLICATIONS

Ge Liping et al., "Advances in the study of non-small cell lung cancer treated with immune checkpoint inhibitors", Modern Oncology, vol. 25, No. 22, Nov. 2017, pp. 3713-3716, (4 pages total).
Yoon-Koo Kang et al., "Nivolumab in patients with advanced gastric or gastro-oesophageal junction cancer refractory to, or intolerant of, at least two previous chemotherapy regimens (ONO-4538-12, Attraction-2): a randomised double-blind, placebo-controlled, phase 3 trial", vol. 390, Dec. 2, 2017, www.thelancet.com, (11 pages total).
Rieneke van de Ven et al., "High PD-1 expression on regulatory and effector T-cells in lung cancer draining lymph nodes", ERJ Open Research, vol. 3, Article ID 00110-2016, ISSN 2312-0541, 2017, 9 pages total.
Wu et al., "Stromal PD-L1-Positive Regulatory T cells and PD-1-Positive CD8-Positive T cells Define the Response of Different Subsets of Non-Small Cell Lung Cancer to PD-1/PD-L1 Blockade Immunotherapy", Journal of Thoracic Oncology, vol. 13, No. 4, ISSN 1556-0864, Dec. 18, 2017, pp. 521-532, 12 pages total.
McDermott et al., "Atezolizumab, an Anti-Programmed Death-Ligand 1 Antibody, in Metastatic Renal Cell Carcinoma: Long-Term Safety, Clinical Activity, and Immune Correlates From a Phase Ia Study", Journal of Clinical Oncology, vol. 34, No. 8, ISSN 0732-183X, Mar. 10, 2016, pp. 833-842, 18 pages total.
Concha-Benavente et al., "Characterisation of Potential Predictive Biomarkers of Response to Nivolumab in Checkmate 141 in Patients With Squamous Cell Carcinoma of the Head and Neck (SCCHN)", Asia-Pac J. Clinical Oncology, vol. 13, No. S4, ISSN 1743-7555, 2017, p. 141, 1 page total.
Office Action dated Jul. 14, 2023, issued by Japanese Patent Office in Japanese Patent Application No. 2020-522606.
Communication with drafting date of Mar. 24, 2023 by the Japanese Intellectual Property Office in Japanese Application No. 2020-522606.
Office Action dated Jul. 14, 2023, issued by Chinese Patent Office in Chinese Patent Application No. 201980036678.6.
Tanday, "Nivolumab for recurrent or metastatic head and neck cancer", The Lancet Oncology, Oct. 13, 2016, p. 483, vol. 17, http://dx.doi.org/10.1016/S1470-2045(16)30505-8.
Office Action issued Nov. 1, 2023 by the State Intellectual Property Administration, PRC in Chinese Patent Application No. 201980036678.6.
Communication issued on Jul. 22, 2024 by the China National Intellectual Property Administration for Chinese Patent Application No. 201980036678.6.
Communication issued on Jul. 23, 2024 by the Intellectual Property Office of the Philippines for Philippines Patent Application No. Jan. 2020/552011.
Communication from the China National Intellectual Property Administration dated Oct. 24, 2024 in Application No. 201980036678.6.

\* cited by examiner

[Figure 1]
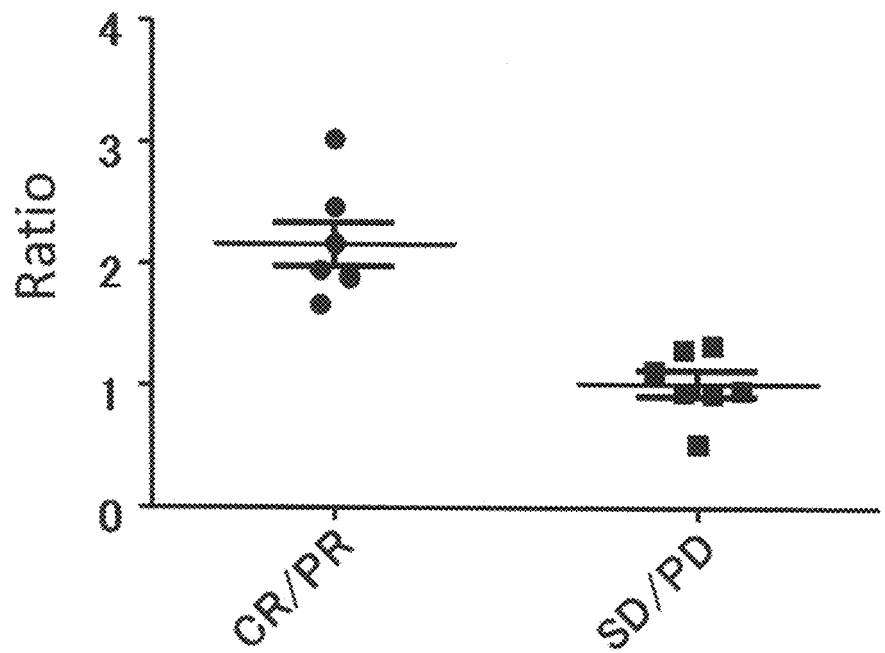
[Figure 2]
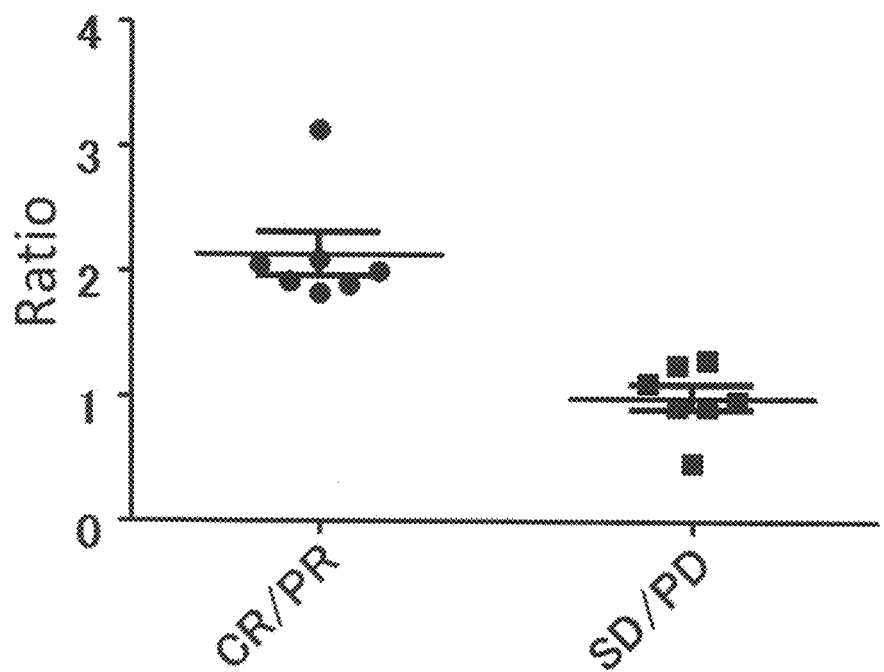

[Figure 3]
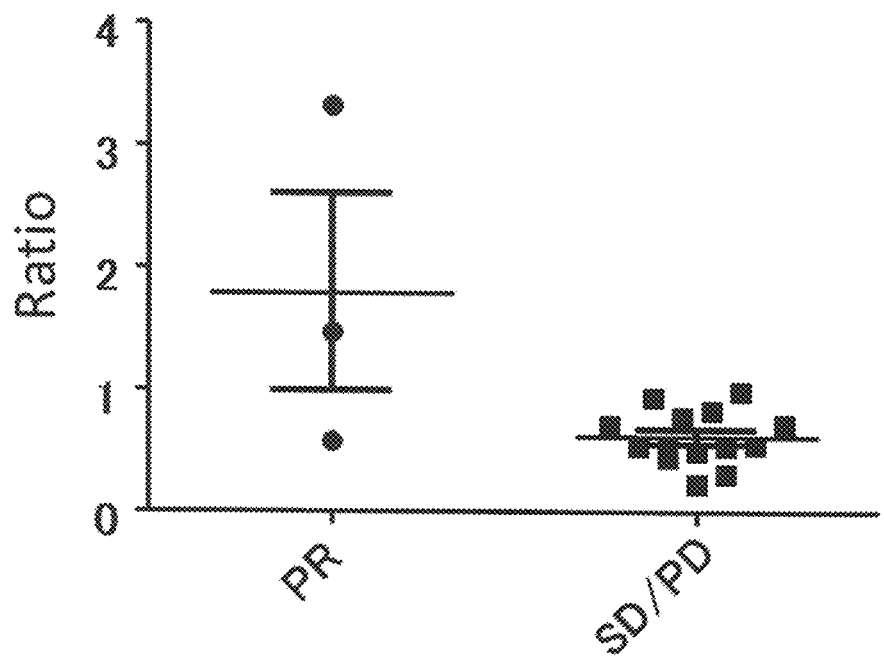
[Figure 4]
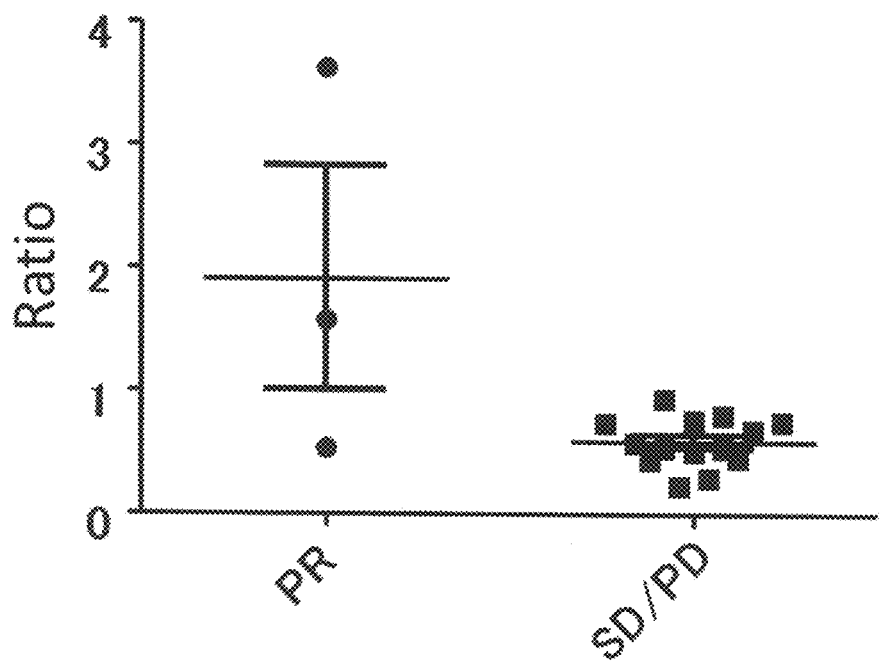

[Figure 5]
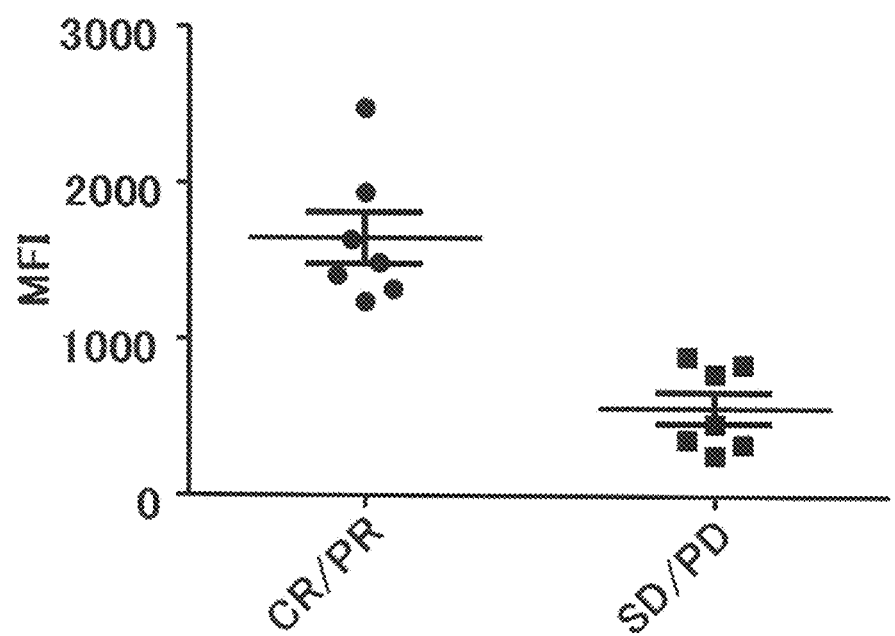
[Figure 6]
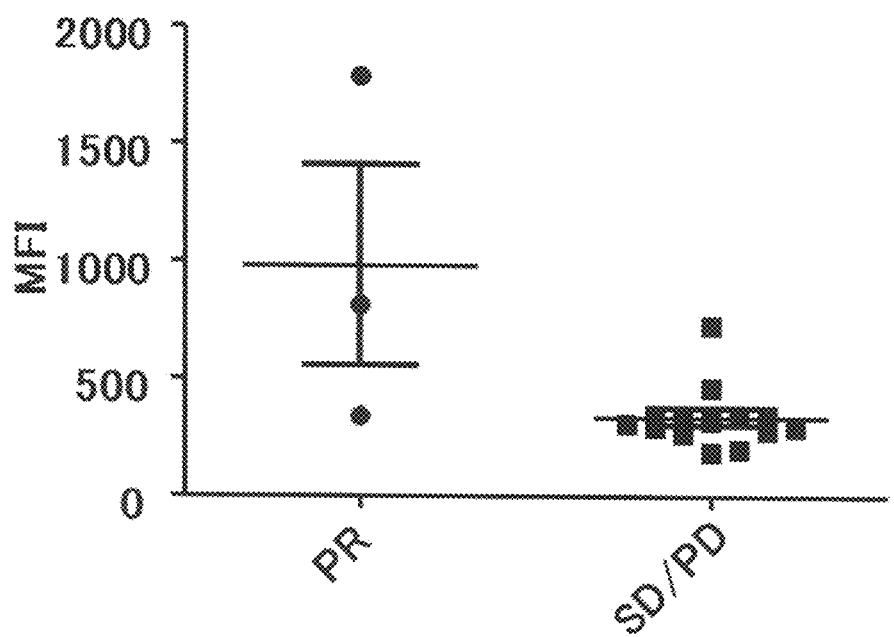

[Figure 7]
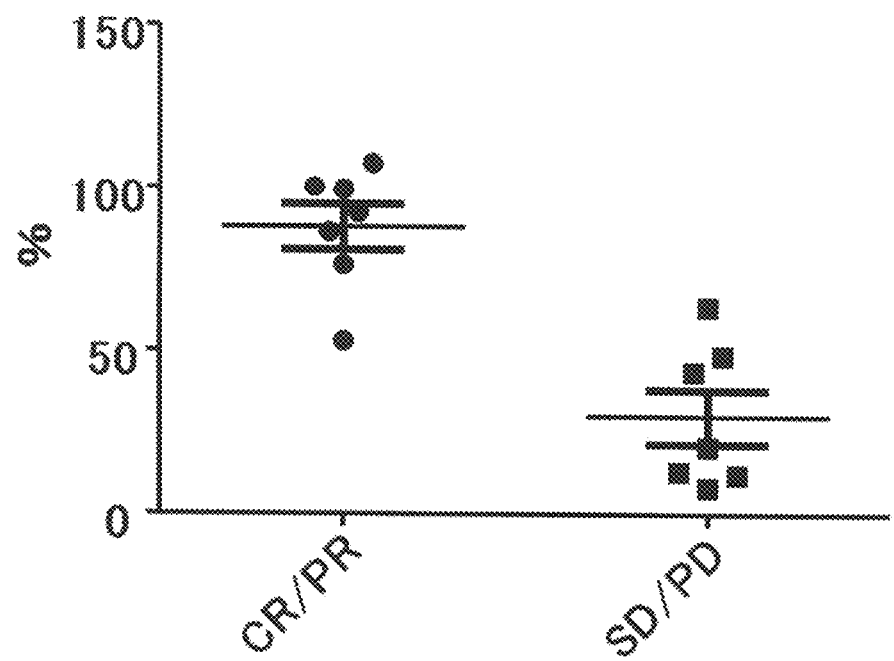
[Figure 8]
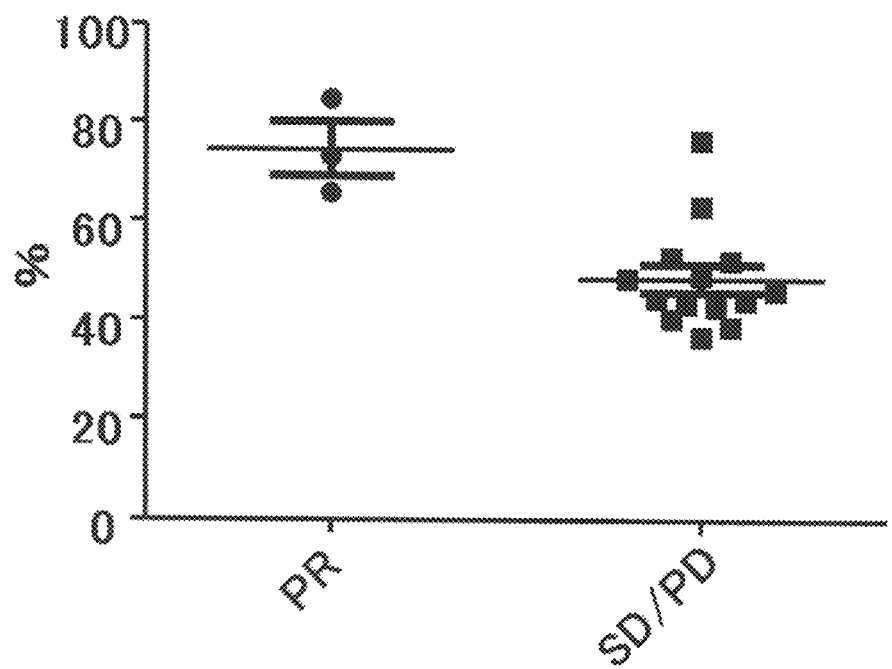

[Figure 9]
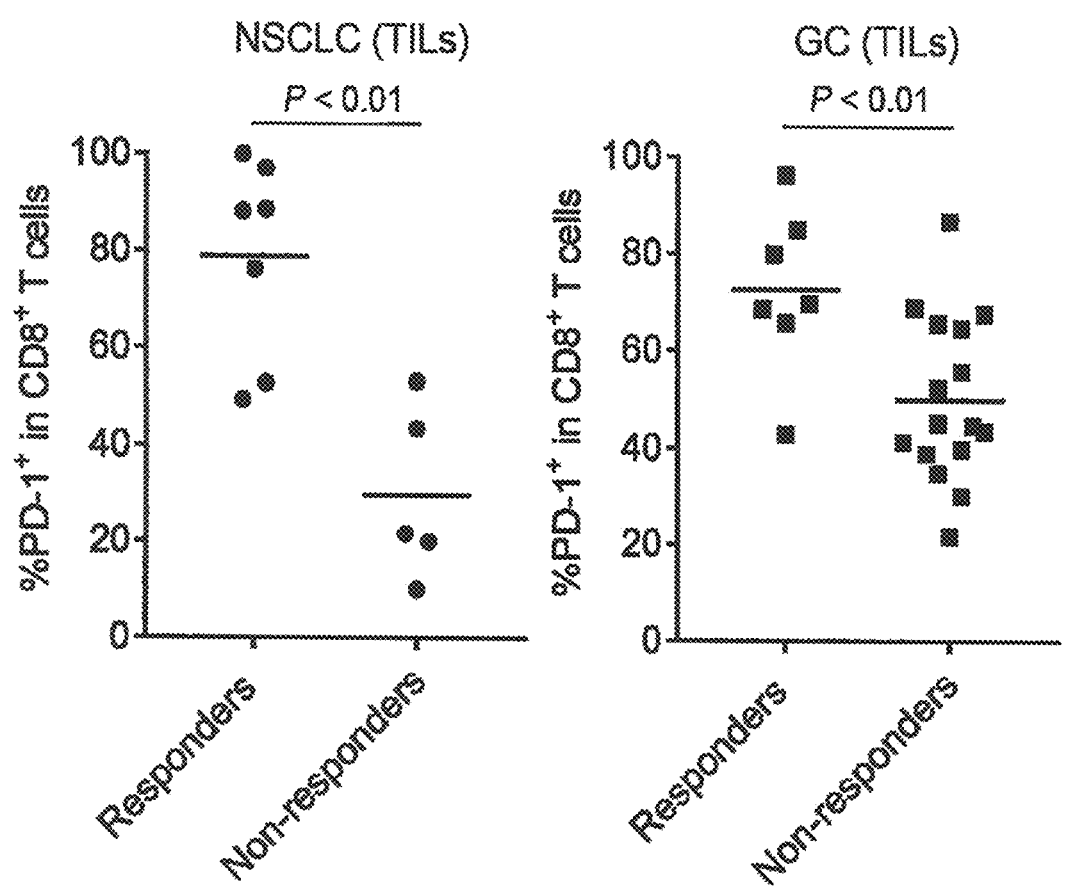

[Figure 10]
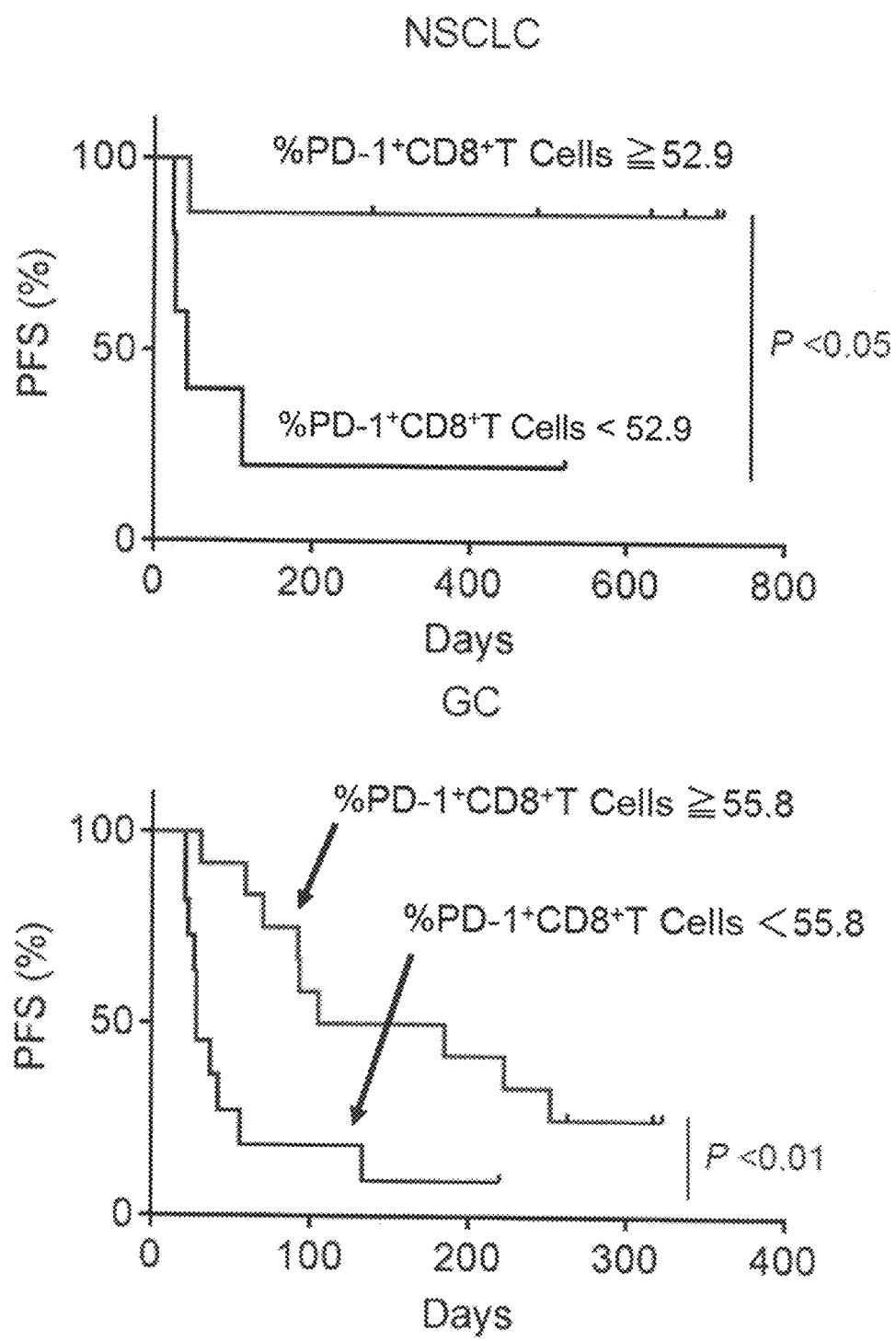

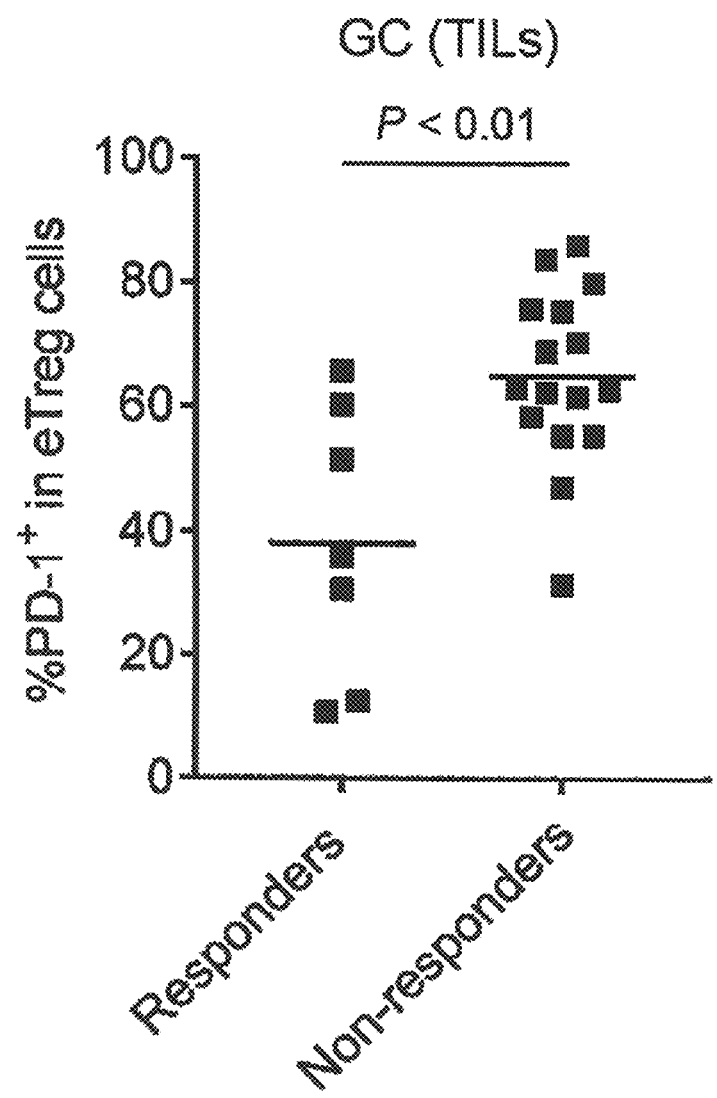
[Figure 11]

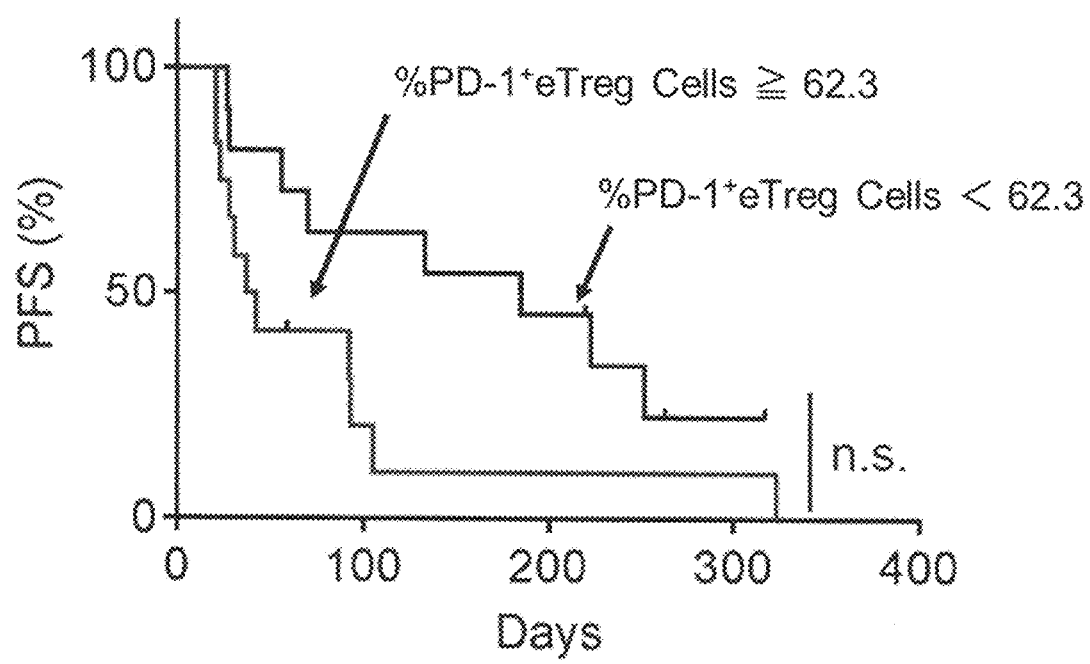
[Figure 12]

[Figure 13]
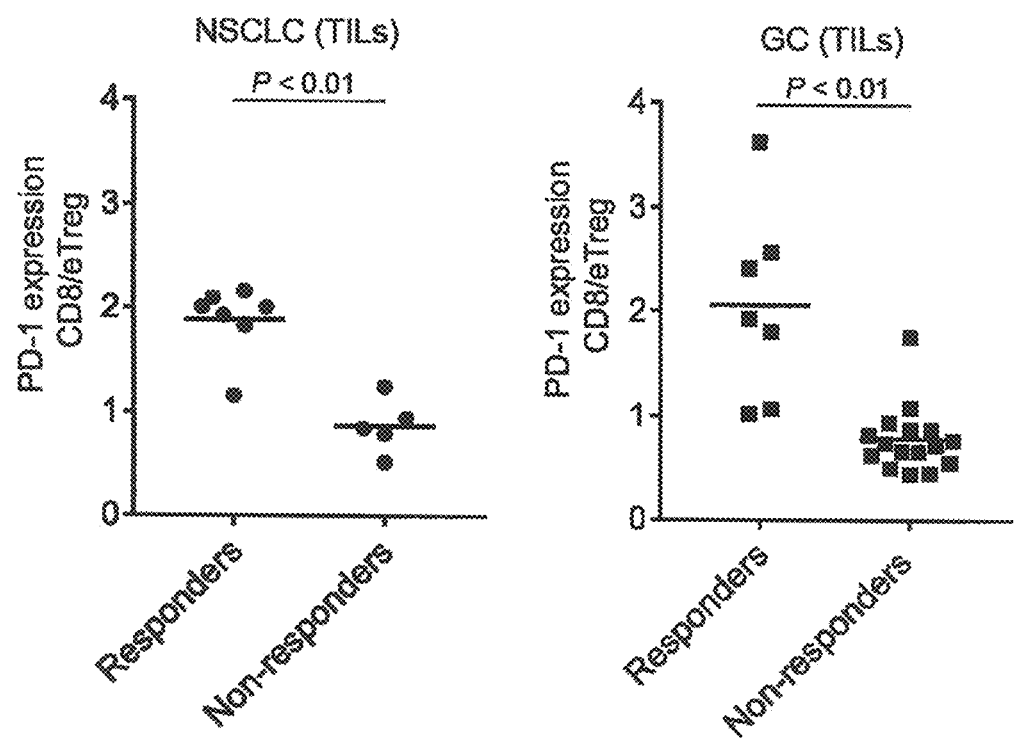

[Figure 14]
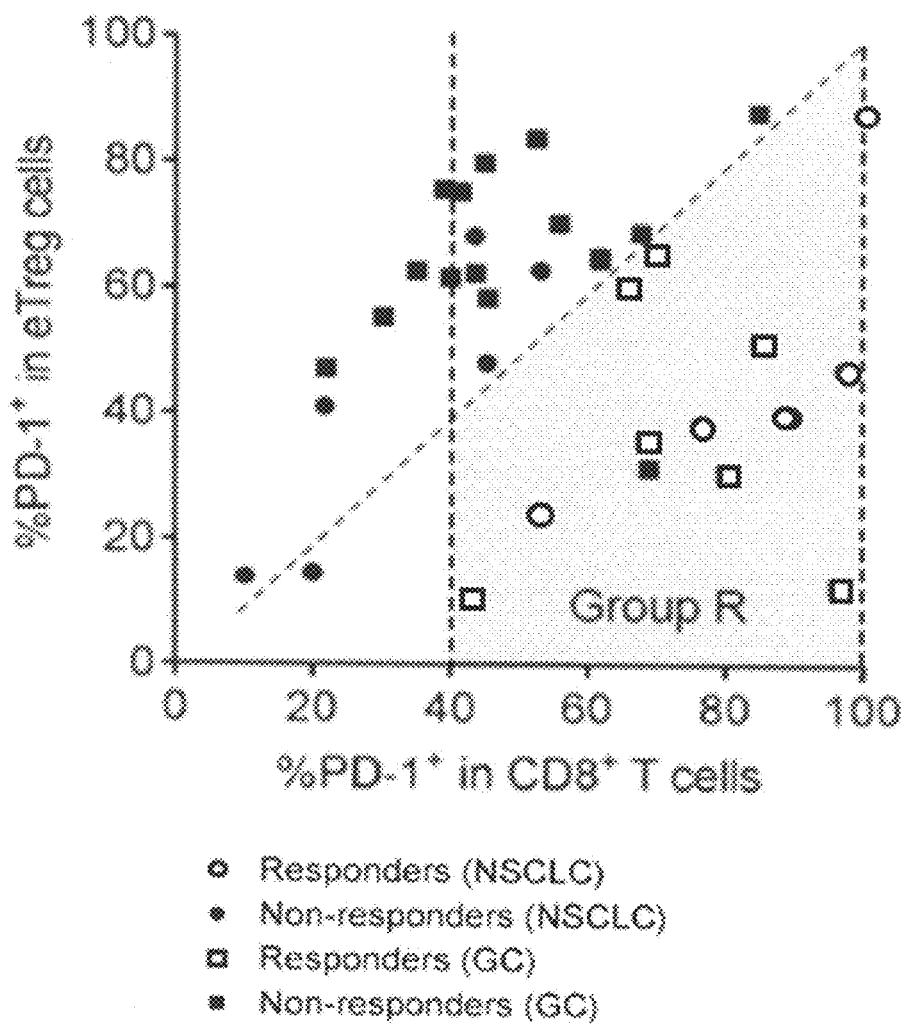

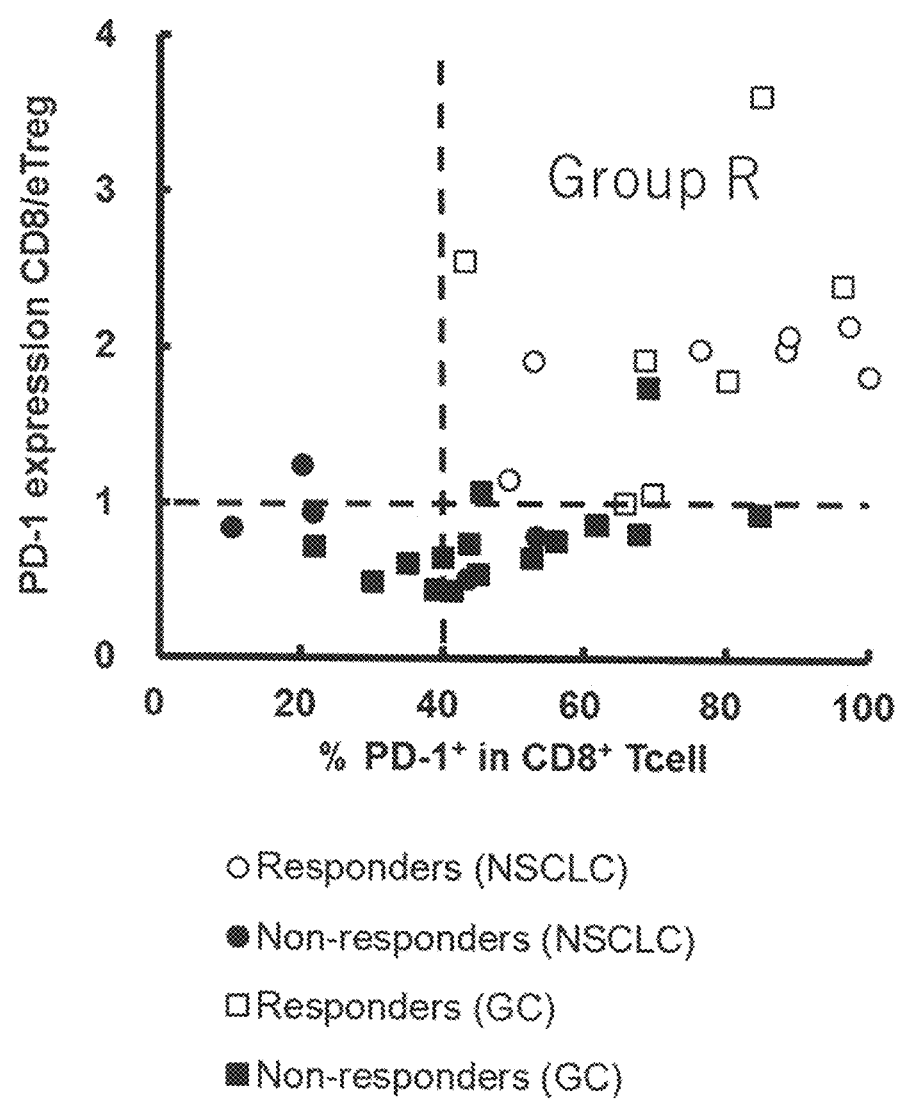
[Figure 15]

[Figure 16]
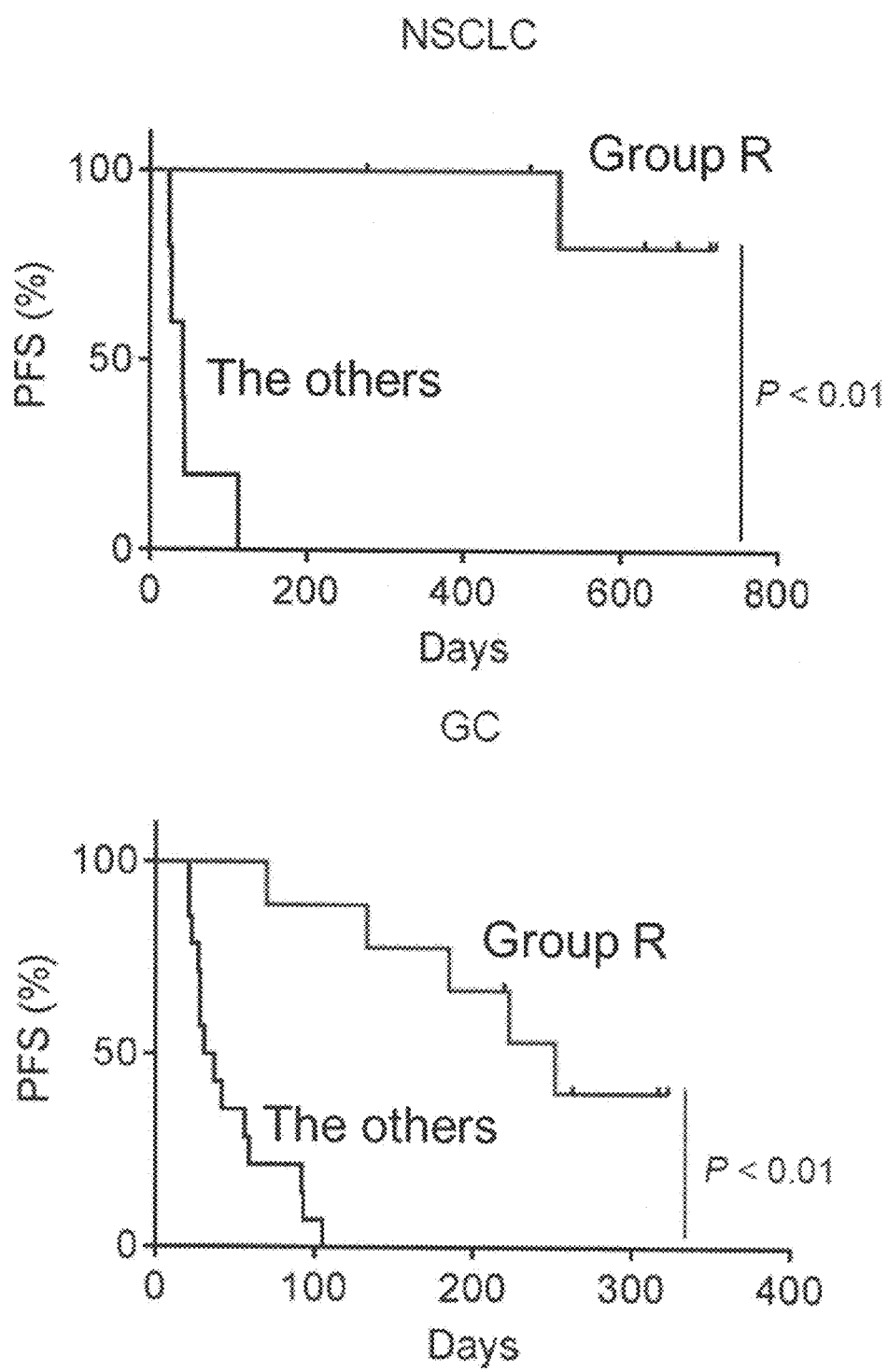

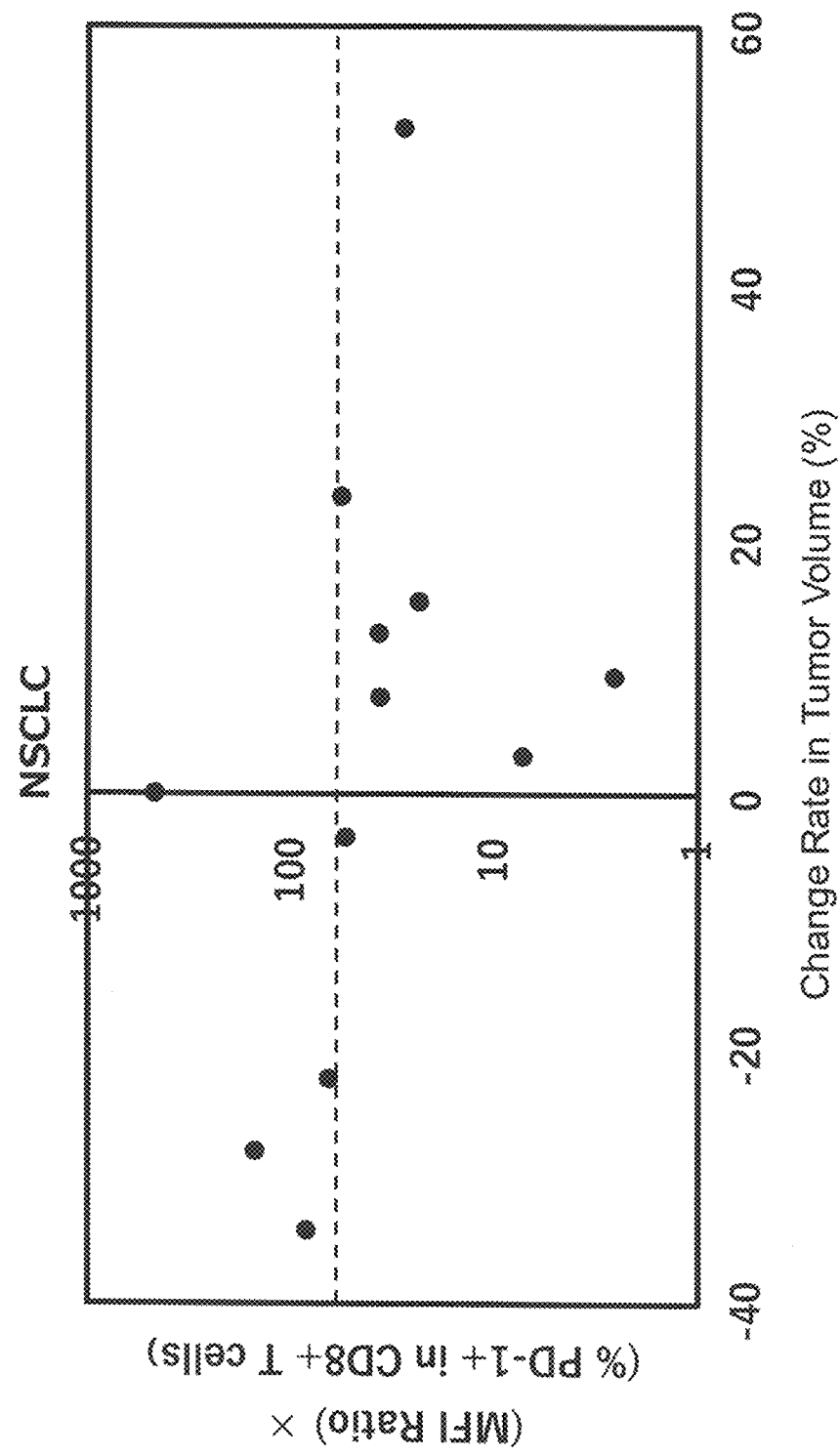
[Figure 17]

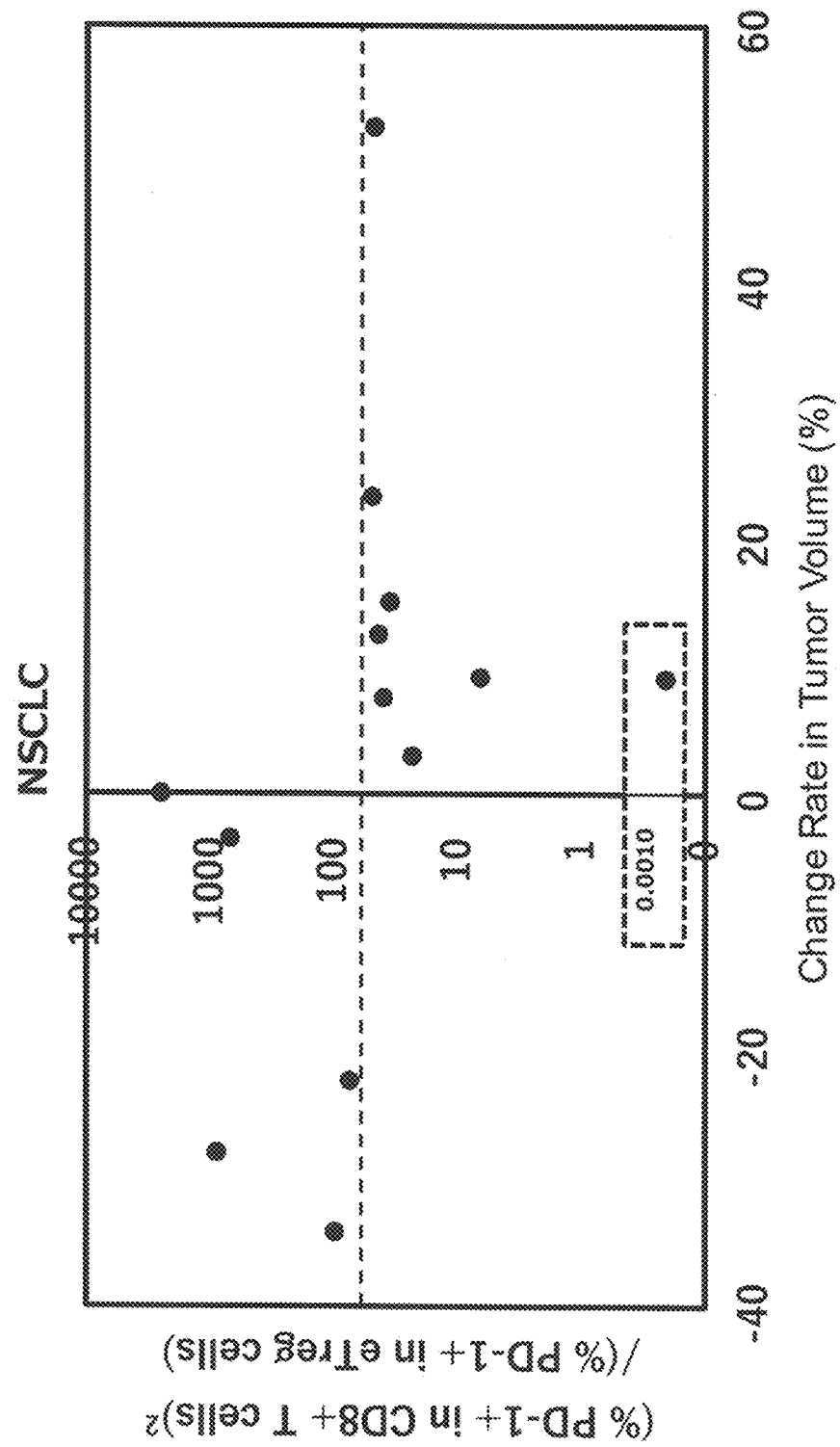
[Figure 18]

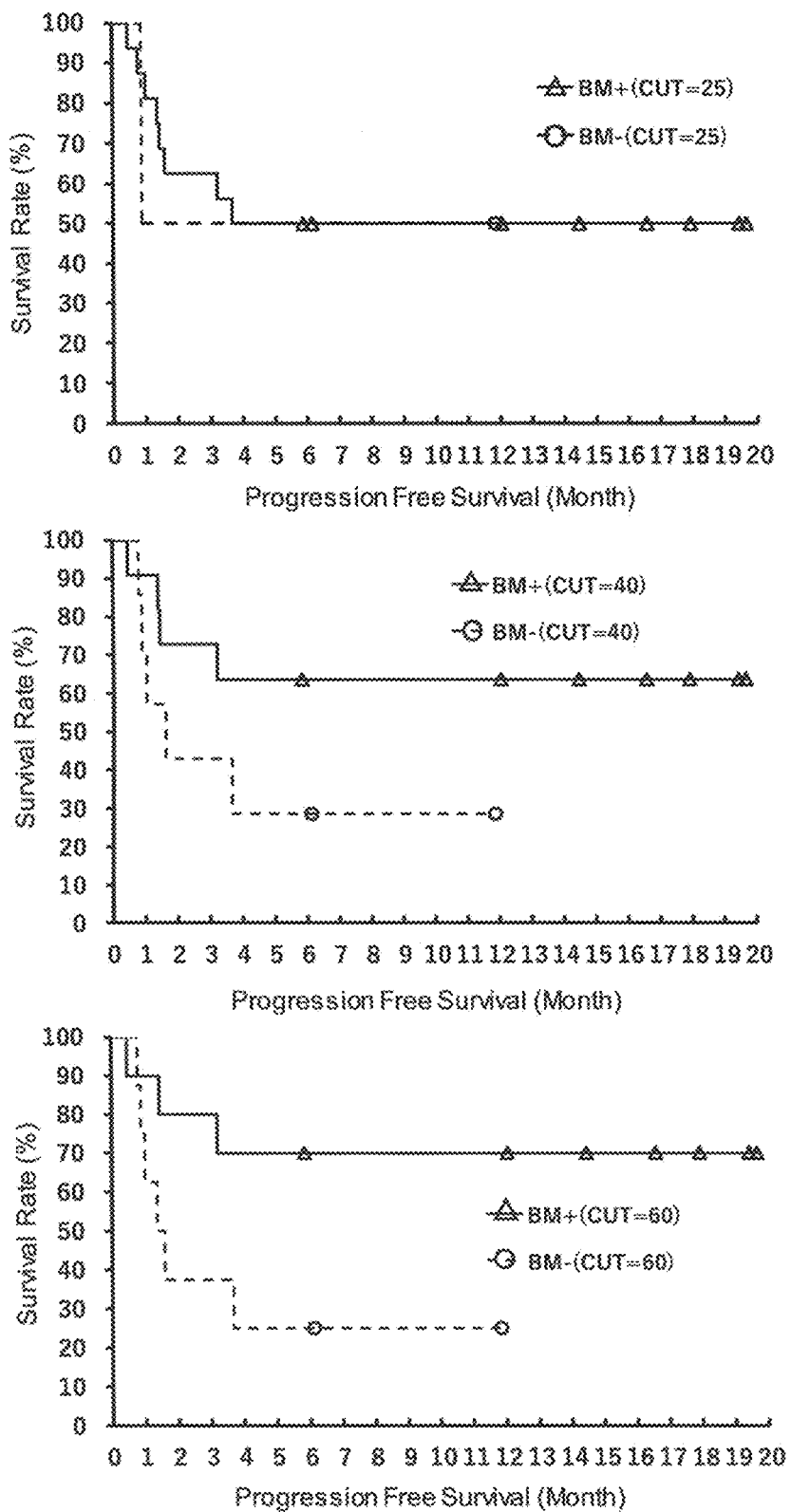
[Figure 19]

[Figure 20]
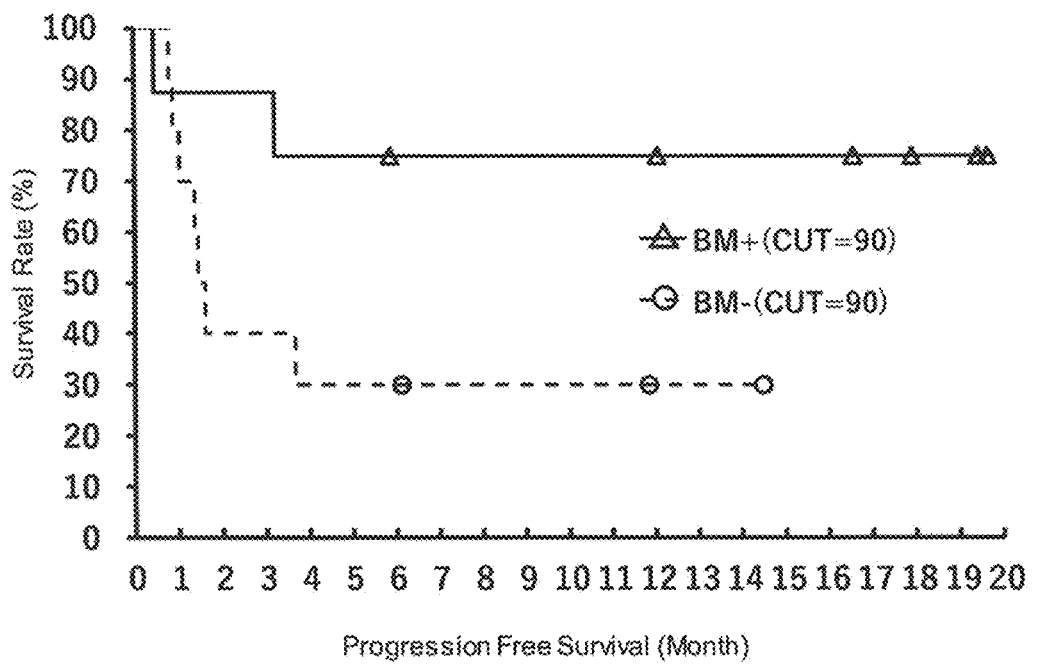
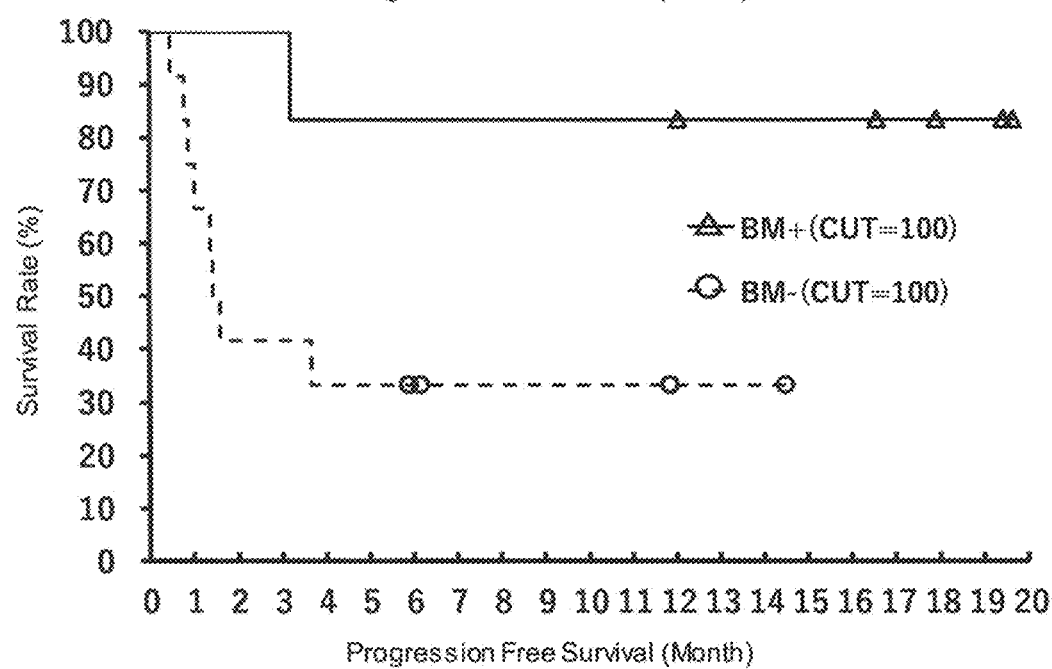

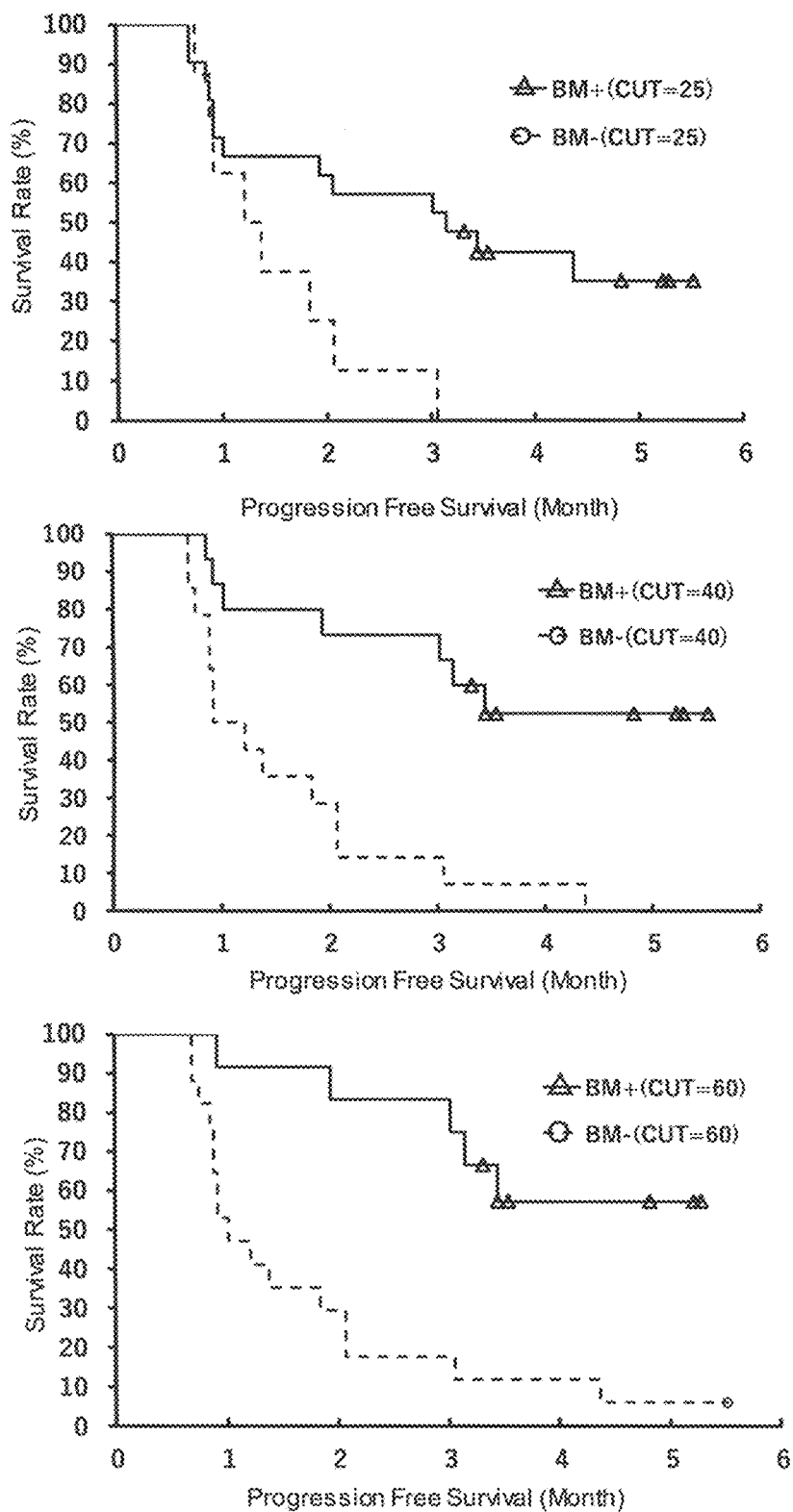
[Figure 21]

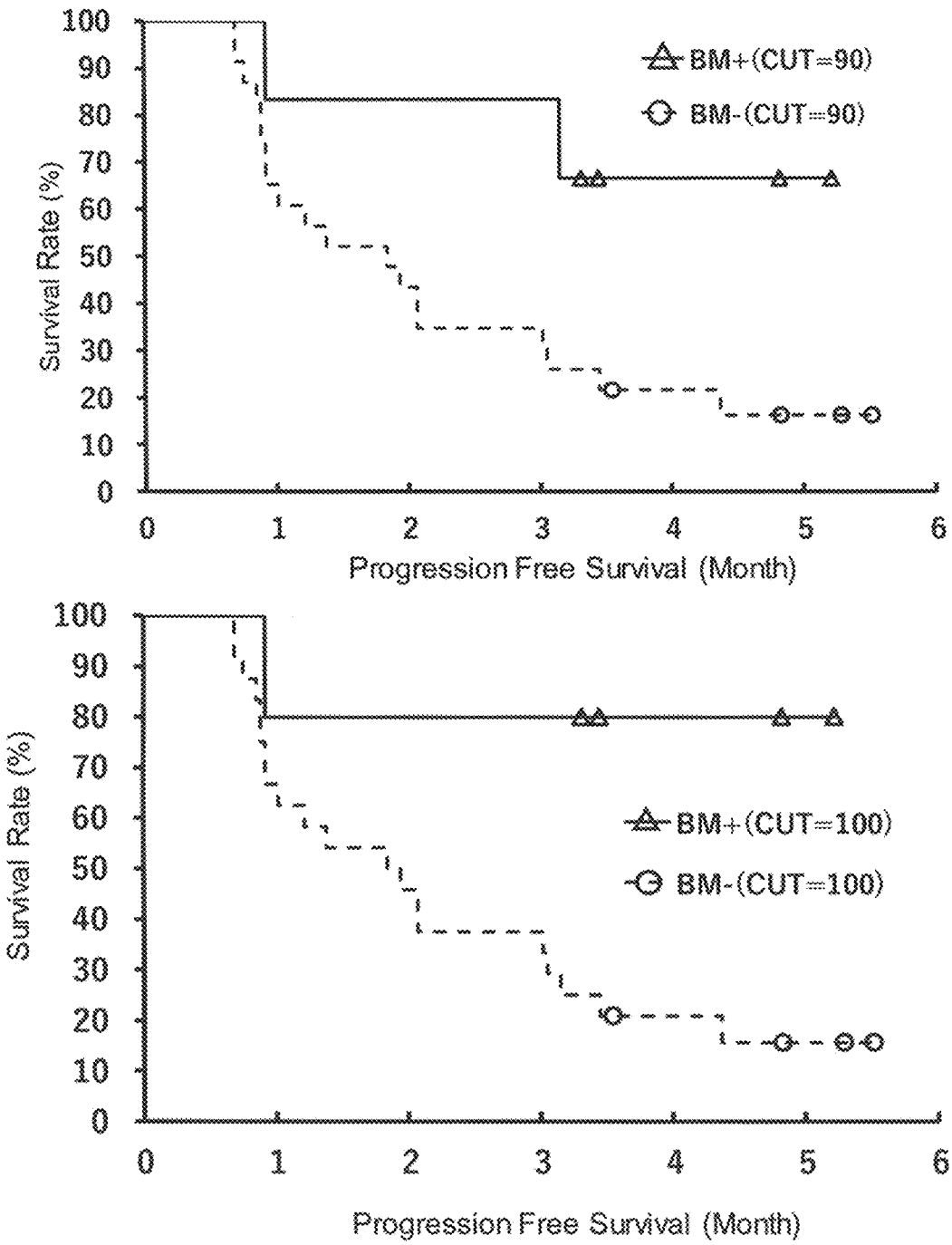
[Figure 22]

[Figure 23]
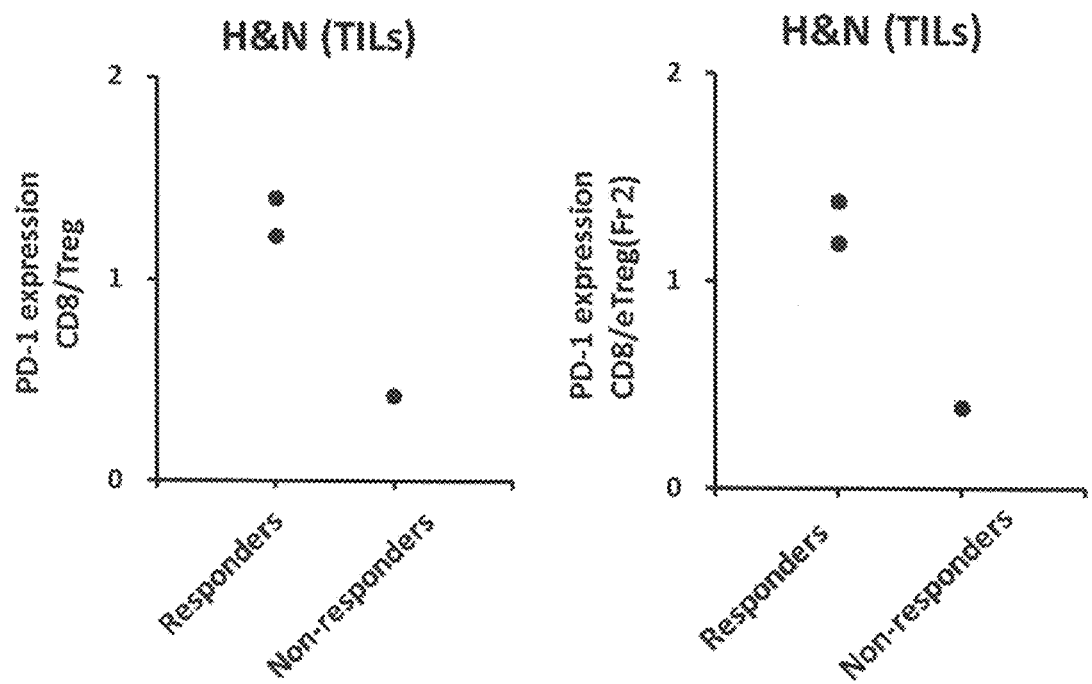

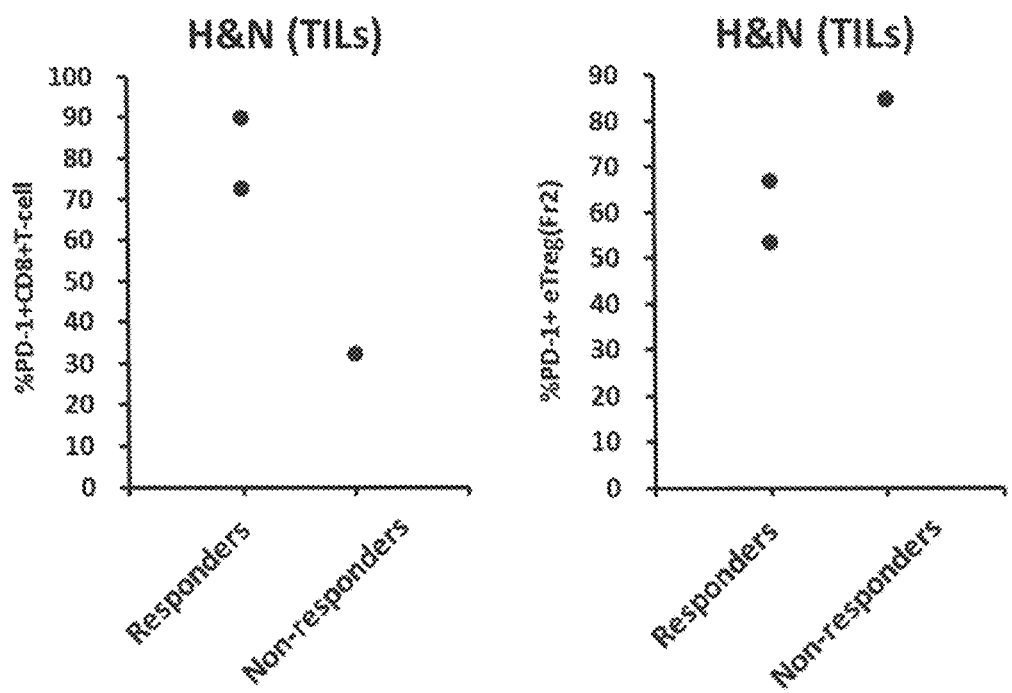
[Figure 24]

[Figure 25]
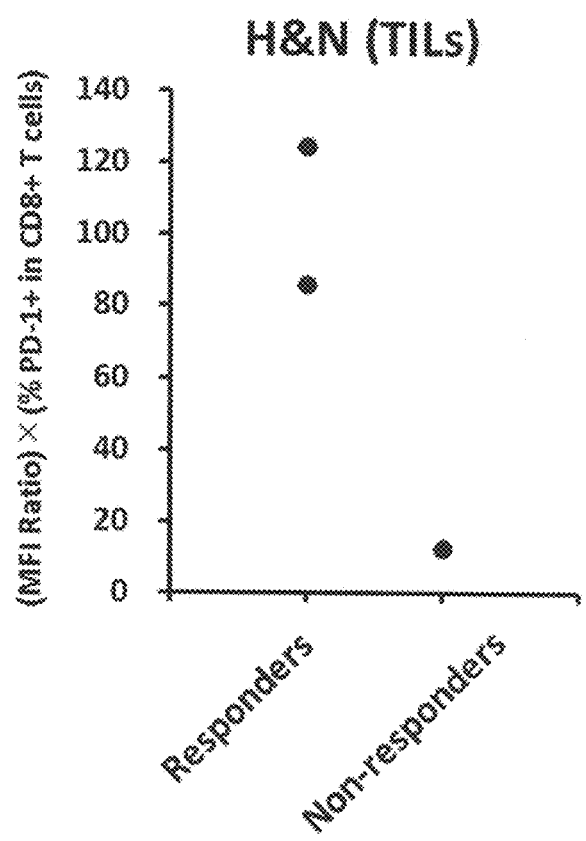

[Figure 26]
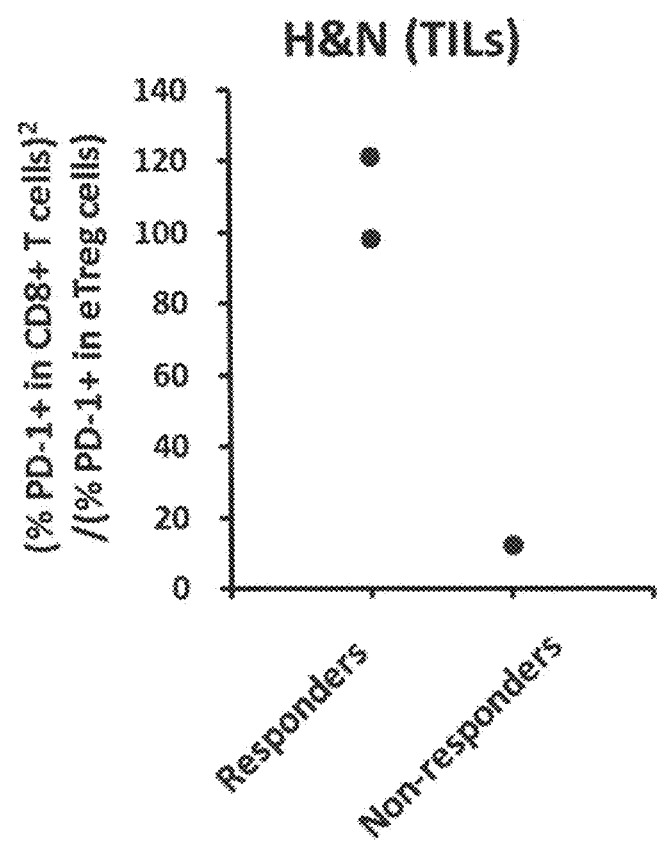

[Figure 27]
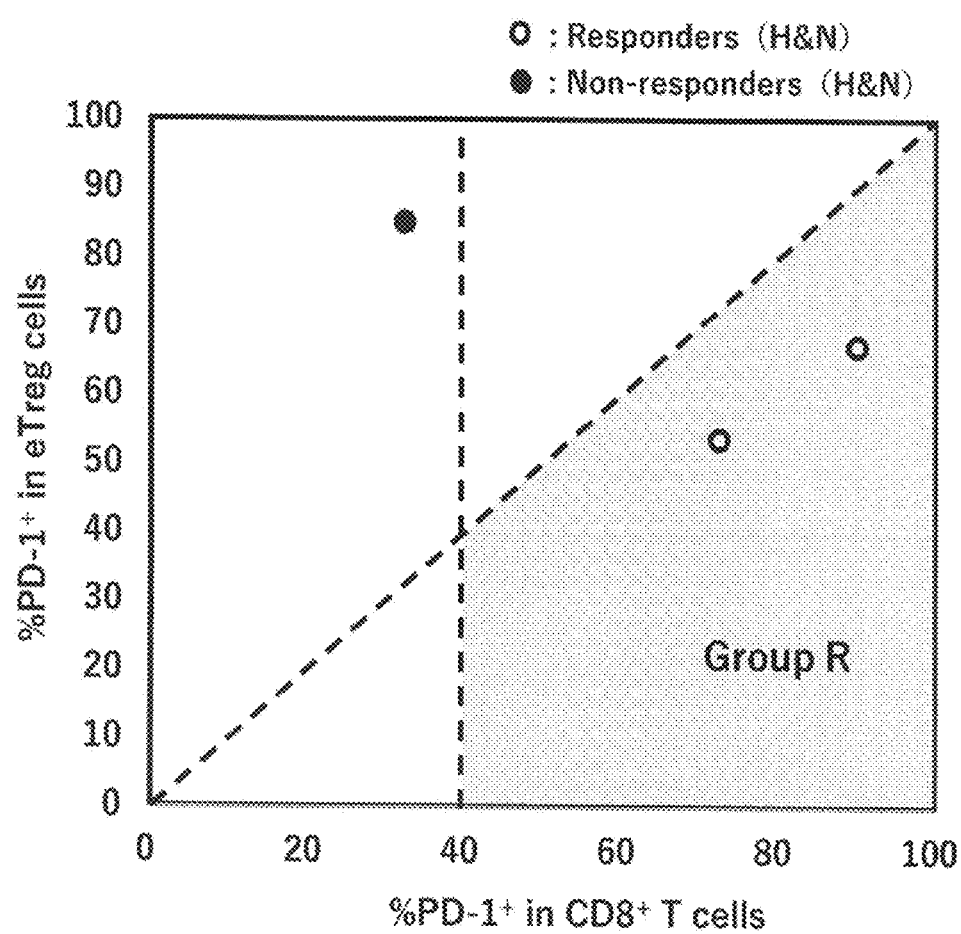

BIOMARKERS FOR DETERMINING THE EFFECTIVENESS OF IMMUNE CHECKPOINT INHIBITORS

This application is a National Stage of International Application No. PCT/JP2019/021633 filed May 30, 2019, claiming priority based on Japanese Patent Application No. 2018-105017, filed May 31, 2018, and Japanese Patent Application No. 2018-189370, filed Oct. 4, 2018, the contents of all of which are incorporated herein by reference in their entirety.

TECHNICAL FIELD

The present invention relates to methods for identifying a patient with malignant tumor in which the effect of an immune checkpoint inhibitor can be more expected, and methods for suppressing the progression of, suppressing the recurrence of, and/or treating malignant tumors, characterized by prescriptions based on those methods.

BACKGROUND ART

Unlike conventional treatments such as surgery, radiation therapy, and drug therapy with anti-neoplastic drugs or molecular targeted drugs, cancer immunotherapy acts on the immune surveillance mechanism inherent in patients with malignant tumors. This is a therapy for suppressing or treating the progress of a malignant tumor by enhancing immunity against the malignant tumor. Recent studies on tumor immunity have revealed that the development of malignant tumors involves an immunosuppressive environment centered on their topical tumor tissue, and that tumors themselves use the systems that evade immune surveillance mechanisms. So-called immune checkpoint molecules such as PD-1 or its ligand, PD-L1, are known as molecules used in such an evasion system, and these inhibitors have already achieved certain results in clinical practice.

However, it is a fact that there are still patients with malignant tumor who do not have any sufficient therapeutic effects even with these immune checkpoint inhibitors, and it is urgently necessary to identify effectiveness markers which can identify patients with promising effects.

The present invention is based on the finding that evaluation items comprising a combination of the respective PD-1 expression intensity, PD-1 expression percentage and the like in $CD8^+$ T cells and Treg cells existing in tumor tissue can be utilized for prediction of effectiveness of an immune checkpoint inhibitor to be administered.

To date, there have been reports suggesting that the ratio between the number of $CD8^+$ T cells and the number of Treg cells in peripheral blood may be correlated with the prognosis of patients with malignant tumors (Non-Patent Document 1), but there is no report about therapy to predict the presence or absence of the effectiveness of the immune checkpoint inhibitor prior to its administration by evaluating the combination of the respective PD-1 expression intensity, PD-1 expression percentage and the like in the respective fractions of immune cell in tumor tissue and then prescribe the immune checkpoint inhibitor for patients identified based on that biomarker.

CITATION LIST

[Non Patent Literature] Non Patent Literature 1: Journal of Clinical Oncology 34, no. 8 (March 2016) 833-842.

SUMMARY OF INVENTION

Technical Problem

The object of the present invention is to provide methods for identifying a patient with malignant tumor on which the effect of an immune checkpoint inhibitor can be more expected, and to provide agents for suppressing the progression of, suppressing the recurrence of, and/or treating malignant tumors, characterized by prescriptions based on those methods.

Solution to Problem

The inventors of the present invention have conducted intensive studies, and as a result, found that the respective evaluation items consisting of a combination of the PD-1 expression intensity, PD-1 expression percentage and the like in Treg cells and $CD8^+$ T cells can be biomarkers capable of predicting the effectiveness for immune checkpoint inhibitors, and completed the present invention.

That is, the present invention is as follows:

[1] An agent for suppressing the progression of, suppressing the recurrence of, and/or treating malignant tumor containing a substance inhibiting an immune checkpoint as an active ingredient, characterized by being administered to a patient with malignant tumor in which a ratio of the PD-1 expression intensity in $CD8^+$ T cells in tumor tissue or blood from the patient with malignant tumor to the PD-1 expression intensity in Treg cells in the same tumor tissue or blood (hereinafter, in the present specification, the ratio may be abbreviated as "Biomarker 1") is about 0.7 or more.

[2] The agent according to the preceding item [1], wherein the ratio described in the preceding item [1] is about 0.74 or more.

[3] The agent according to the preceding item [1], wherein the ratio described in the preceding item [1] is about 0.8 or more.

[4] The agent according to the preceding item [1], wherein the ratio described in the preceding item [1] is about 0.9 or more.

[5] The agent according to the preceding item [1], wherein the ratio described in the preceding item [1] is about 1.0 or more.

[6] The agent according to the preceding item [1], wherein the ratio described in the preceding item [1] is about 1.1 or more.

[7] The agent according to the preceding item [1], wherein the ratio described in the above item [1] is about 1.2 or more.

[8] The agent according to the preceding item [1], wherein the ratio described in the preceding item [1] is about 1.25 or more.

[9] The agent according to the preceding item [1], wherein the ratio described in the preceding item [1] is about 1.27 or more.

[10] The agent according to the preceding item [1], wherein the ratio described in the preceding item [1] is about 1.3 or more.

[11] The agent according to the preceding item [1], wherein the ratio described in the preceding item [1] is about 1.4 or more.

[12] The agent according to the preceding item [1], wherein the ratio described in the preceding item [1] is about 1.5 or more.

[13] The agent according to the preceding item [1], wherein the ratio described in the preceding item [1] is about 1.6 or more.

[14] The agent according to the preceding item [1], wherein the ratio described in the preceding item [1] is about 1.7 or more.

[15] The agent according to the preceding item [1], wherein the ratio described in the preceding item [1] is about 1.8 or more.

[16] The agent according to the preceding item [1], wherein the ratio described in the preceding item [1] is about 1.9 or more.

[17] The agent according to the preceding item [1], wherein the ratio described in the preceding item [1] is an arbitrary ratio between about 0.7 and about 1.9, or more.

[18] The agent according to any one of the preceding items [1] to [17], wherein the ratio described in the preceding item [1] is an arbitrary ratio between about 2.6 and about 5.9, or less.

[19] An agent for suppressing the progression of, suppressing the recurrence of, and/or treating malignant tumor containing a substance inhibiting an immune checkpoint as an active ingredient, characterized by being administered to a patient with malignant tumor in which the mean fluorescence intensity (hereinafter, abbreviated as MFI, which may be abbreviated as "Biomarker 2" in the present specification), measured by flow cytometry, of the PD-1 expression intensity in $CD8^+$ T cells in tumor tissue or blood from the patient with malignant tumor is about 400 or more.

[20] The agent according to the preceding item [19], wherein the MFI of PD-1 expression described in the preceding item [19] is about 410 or more.

[21] The agent according to the preceding item [19], wherein the MFI of PD-1 expression described in the preceding item [19] is about 450 or more.

[22] The agent according to the preceding item [19], wherein the MFI of PD-1 expression described in the preceding item [19] is about 500 or more.

[23] The agent according to the preceding item [19], wherein the MFI of PD-1 expression described in the preceding item [19] is about 550 or more.

[24] The agent according to the preceding item [19], wherein the MFI of PD-1 expression described in the preceding item [19] is about 600 or more.

[25] The agent according to the preceding item [19], wherein the MFI of PD-1 expression described in the preceding item [19] is about 650 or more.

[26] The agent according to the preceding item [19], wherein the MFI of PD-1 expression described in the preceding item [19] is about 700 or more.

[27] The agent according to the preceding item [19], wherein the MFI of PD-1 expression described in the preceding item [19] is about 750 or more.

[28] The agent according to the preceding item [19], wherein the MFI of PD-1 expression described in the preceding item [19] is about 800 or more.

[29] The agent according to the preceding item [19], wherein the MFI of PD-1 expression described in the preceding item [19] is about 810 or more.

[30] The agent according to the above item [19], wherein the MFI of PD-1 expression described in the preceding item [19] is about 850 or more.

[31] The agent according to the preceding item [19], wherein the MFI of PD-1 expression described in the preceding item [19] is an arbitrary numerical value between about 400 and about 850, or more.

[32] The agent according to any one of the preceding items [19] to [31], wherein the MFI of PD-1 expression described in the preceding item [19] is an arbitrary numerical value between about 2050 and about 2810, or less.

[33] An agent for suppressing the progression of, suppressing the recurrence of, and/or treating malignant tumor containing a substance inhibiting an immune checkpoint as an active ingredient, characterized by being administered to a patient with malignant tumor in which a percentage (%) of the number of PD-1-expressing cells among $CD8^+$ T cells in tumor tissue or blood from the patient with malignant tumor (hereinafter, the percentage is abbreviated as "Biomarker 3" in the present specification) is about 35% or more.

[34] The agent according to the preceding item [33], wherein the percentage described in the preceding item [33] is about 40% or more.

[35] The agent according to the preceding item [33], wherein the percentage described in the preceding item [33] is about 45% or more.

[36] The agent according to the preceding item [33], wherein the percentage described in the preceding item [33] is about 49.7% or more.

[37] The agent according to the preceding item [33], wherein the percentage described in the preceding item [33] is about 50% or more.

[38] The agent according to the preceding item [33], wherein the percentage described in the preceding item [33] is about 50.7% or more.

[39] The agent according to the preceding item [33], wherein the percentage described in the preceding item [33] is about 60% or more.

[40] The agent according to the preceding item [33], wherein the percentage described in the preceding item [33] is about 70% or more.

[41] The agent according to the preceding item [33], wherein the percentage described in the preceding item [33] is an arbitrary percentage between about 35 and about 70%, or more.

[42] An agent for suppressing the progression of, suppressing the recurrence of, and/or treating malignant tumor containing a substance inhibiting an immune checkpoint as an active ingredient, characterized by being administered to a patient with malignant tumor in which a percentage (%) of the number of PD-1-expressing cells among Treg cells in tumor tissue or blood from the patient with malignant tumor (hereinafter, the percentage is abbreviated as "Biomarker 4" in the present specification) is less than about 65%.

[43] The agent according to the preceding item [42], wherein the percentage described in the preceding item [42] is less than about 60%.

[44] The agent according to the preceding item [42], wherein the percentage described in the preceding item [42] is less than about 58.4%.

[45] The agent according to the preceding item [42], wherein the percentage described in the preceding item [42] is less than about 55%.

[46] The agent according to the preceding item [42], wherein the percentage described in the preceding item [42] is less than an arbitrary ratio between about 65 to about 55%.

[47] An agent for suppressing the progression of, suppressing the recurrence of, and/or treating malignant tumor containing a substance inhibiting an immune checkpoint as an active ingredient, characterized by being administered to a patient with malignant tumor, in which either of:
(a1) a ratio of the PD-1 expression intensity in $CD8^+$ T cells in tumor tissue or blood from the patient with malignant tumor to the PD-1 expression intensity in Treg cells in the same tumor tissue or blood (Biomarker 1), and
(a2) a ratio of the percentage (%) of the number of PD-1-expressing cells among the same $CD8^+$ T cells (Biomarker 3) to the percentage (%) of the number of PD-1-expressing cells among the same Treg cells (Biomarker 4),
is about 0.8 or more, and
(b) the percentage (%) of the number of PD-1-expressing cells among the same CD8+ T cells (Biomarker 3) is about 35% or more (hereinafter, in the specification, the combination of the ratio in the preceding (a1) or (a2) and the percentage in preceding (b) may be abbreviated as "Biomarker 5").

[48] The agent according to the preceding item [47], wherein the ratio described in the preceding (a1) or (a2) in the preceding item [47] is about 0.9 or more.

[49] The agent according to the preceding item [47], wherein the ratio described in the preceding (a1) or (a2) in the preceding item [47] is about 1.0 or more.

[50] The agent according to the preceding item [47], wherein the ratio described in the preceding (a1) or (a2) in the preceding item [47] is about 1.1 or more.

[Si] The agent according to the preceding item [47], wherein the ratio described in the preceding (a1) or (a2) in the preceding item [47] is about 1.2 or more.

[52] The agent according to any one of the preceding items [47] to [Si], wherein the percentage described in the preceding (b) in the preceding item [47] is about 40% or more.

[53] The agent according to any one of the preceding items [47] to [51], wherein the percentage described in the preceding (b) in the preceding item [47] is about 45% or more.

[54] An agent for suppressing the progression of, suppressing the recurrence of, and/or treating malignant tumor containing substance inhibiting an immune checkpoint as an active ingredient, characterized by being administered to a patient with malignant tumor, in which either of:
(a1) a ratio of the PD-1 expression intensity in CD8+ T cells in tumor tissue from the patient with malignant tumor to the PD-1 expression intensity of Treg cells in the same tissue, and
(a2) a ratio of the percentage (%) of the number of PD-1-expressing cells among the same CD8+ T cells to the percentage (%) of the number of PD-1-expressing cells among the same Treg cells,
is about 1.0 or more, and
(b) the percentage (%) of the number of PD-1-expressing cells among the same CD8+ T cells is about 40% or more.

[55] An agent for suppressing the progression of, suppressing the recurrence of, and/or treating malignant tumor containing substance inhibiting an immune checkpoint as an active ingredient, characterized by being administered to a patient with malignant tumor, in which the numerical value calculated by multiplying the ratio of the PD-1 expression intensity in CD8+ T cells in tumor tissue or blood from the patient with malignant tumor to the PD-1 expression intensity in Treg cells in the same tumor tissue or blood (Biomarker 1) by the percentage (%) of the number of PD-1-expressing cells among the same CD8+ T cells (Biomarker 3) (hereinafter, may be abbreviated as "Biomarker 6" in the present specification) is about 25 or more.

[56] An agent for suppressing the progression of, suppressing the recurrence of, and/or treating malignant tumor containing a substance inhibiting an immune checkpoint as an active ingredient, characterized by being administered to a patient with malignant tumor, in which the numerical value calculated by dividing the square of the percentage (%) of the number of PD-1-expressing cells among CD8+ T cells in tumor tissue or blood from the patient with malignant tumor (Biomarker 3) by the percentage (%) of the number of PD-1-expressing cells among Treg cells in the same tissue or blood (Biomarker 4)(hereinafter, may be abbreviated as "Biomarker 7" in the present specification) is about 25 or more.

[57] The agent according to the preceding item [55] or [56], wherein the numerical value described in the preceding item [55] or [56] is about 40 or more or about 44.4 or more.

[58] The agent according to the preceding item [55] or [56], wherein the numerical value described in the preceding item [55] or [56] is about 46.0 or more or about 50 or more.

[59] The agent according to the preceding item [55] or [56], wherein the numerical value described in the preceding item [55] or [56] is about 60 or more.

[60] The agent according to the preceding item [55] or [56], wherein the numerical value described in the preceding item [55] or [56] is about 90 or more.

[61] The agent according to the preceding item [55] or [56], wherein the numerical value of described in the preceding item [55] or [56] is about 100 or more.

[62] The agent according to any one of the preceding items [1] to [18], [47] to [55], and [57] to [61], wherein the respective PD-1 expression intensities in Treg cells and CD8+ cells in tumor tissue or blood is represented by the MFI measured by flow cytometry, the expression intensity or expression intensity score measured by multiplex immunohistochemical staining, the signal intensity or expression intensity score measured by in situ hybridization, the expression intensity or signal intensity measured by mass cytometry, the expression level or gene count value measured by single cell RNA sequencing, or the expression intensity or expression intensity score measured by mass imaging.

[63] The agent according to any one of the preceding items [33] to [61], wherein the respective numbers of CD8+ T cells and Treg cells in tumor tissue or blood and the respective numbers of PD-1-expressing cells among them are measured by flow cytometry or immunostaining.

[64] The agent according to any one of the preceding items [1] to [18] and [42] to [63], wherein the Treg cells are Fraction II Treg cells (hereinafter, may be abbreviated as "Treg cells (Fr. II)" or "eTreg cells").

[65] The agent according to any one of the preceding items [1] to [64], wherein the substance inhibiting an immune checkpoint is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[66] The agent according to the preceding item [65], wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283.

[67] The agent according to the preceding item [65], wherein the anti-PD-L1 antibody is Atezolizumab, Avelumab, Durvalumab, BMS-936559, STI-1014, KN035, LY3300054, HLX20, SHR-1316, CS1001, MSB2311, BGB- A333, KL-A167, CK-301, AK106, AK104, ZKAB001, FAZ053, CBT-502, JS003 or CX-072.

[68] The agent according to the preceding item [65], wherein the anti-CTLA-4 antibody is Ipilimumab, AGEN1884 or Tremelimumab.

[69] The agent according to any one of the preceding items [1] to [68], wherein the malignant tumor is solid cancer or blood cancer.

[70] The agent according to the preceding item [69], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., high frequency microsatellite instability (hereinafter, abbreviated as "MSI-H") and/or mismatch repair deficient (hereinafter, abbreviated as "dMMR") positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[71] The agent according to the preceding item [69], wherein the blood cancer is one or more cancers selected from multiple myeloma, malignant lymphoma (e.g., non-Hodgkin's lymphoma (e.g., follicular lymphoma, diffuse large B-cell lymphoma, MALT lymphoma, lymphoplasmacytic lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), central nervous system malignant lymphoma, myelodysplastic syndrome and myeloproliferative syndrome.

[72] The agent according to any one of the preceding items [1], [18], [62] and [64] to [70], wherein in the case that the malignant tumor is non-small cell lung cancer, the ratio described in the preceding item [1] is 1.2 or more.

[73] The agent according to any one of the preceding items [19], [32] and [65] to [70], wherein in the case that the malignant tumor is non-small cell lung cancer, the MFI of PD-1 expression described in the preceding item [19] is 800 or more.

[74] The agent according to any one of the preceding items [56] and [63] to [70], wherein in the case that the malignant tumor is non-small cell lung cancer, the numerical value described in the preceding item [56] is about 40 or more.

[75] The agent according to any one of the preceding items [1], [18], [62] and [64] to [70], wherein in the case that the malignant tumor is gastric cancer, the ratio described in the preceding item [1] is 0.7 or more.

[76] The agent according to any one of the preceding items [19], [32] and [65] to [70], wherein in the case that the malignant tumor is gastric cancer, the MFI of PD-1 expression described in the preceding item [19] is 410 or more.

[77] The agent according to any one of the preceding items [1] to [69], wherein the malignant tumor is childhood cancer or unknown primary cancer.

[78] The agent according to any one of the preceding items [1] to [77], wherein the malignant tumor is one on which the therapeutic effects of other anti-neoplastic drugs are insufficient or not sufficient.

[79] The agent according to any one of the preceding items [1] to [77], wherein the malignant tumor is one worsened after treatment with other anti-neoplastic agents.

[80] The agent according to any one of the preceding items [1] to [77], wherein the patient with malignant tumor has not been treated with any other anti-neoplastic agents.

[81] The agent according to any one of the preceding items [1] to [80], prescribed in a postoperative adjuvant therapy or preoperative adjuvant therapy.

[82] The agent according to any one of the preceding items [1] to [81], wherein the malignant tumor is incurable or unresectable, metastatic, recurrent, refractory and/or distant metastatic.

[83] The agent according to any one of the preceding items [1] to [82], wherein the percentage of PD-L1-expressing tumor cells among tumor cells in tumor tissue (hereinafter, abbreviated as "TPS") or the numerical value obtained by dividing the number of PD-L1 positive cells (tumor cells, lymphocytes and macrophages) by the total number of tumor cells and multiplying by 100 (hereinafter, abbreviated as "CPS") is 50% or more, 25% or more, 10% or more, 5% or more, or 1% or more.

[84] The agent according to any one of the preceding items [1] to [82], wherein TPS or CPS is less than 50%, less than 25%, less than 10%, less than 5% or less than 1%.

[85] The agent according to any one of the preceding items [1] to [84], wherein the malignant tumor has MSI-H and/or dMMR.

[86] The agent according to any one of the preceding items [1] to [84], wherein the malignant tumor does not have MSI-H and/or dMMR, or has low frequency microsatellite instability (hereinafter abbreviated as "MSI-L").

[87] The agent according to any one of the preceding items [70], [72] to [74] and [77] to [86], wherein malignant melanoma or non-small cell lung cancer is BRAF V600E mutation-positive.

[88] The agent according to any one of the preceding items [70], [72] to [74] and [77] to [86], wherein malignant melanoma or non-small cell lung cancer is BRAF V600 wild type.

[89] The agent according to any one of the preceding items [70], [72] to [74] and [77] to [88], wherein non-small cell lung cancer is EGFR gene mutation positive and/or ALK fusion gene positive.

[90] The agent according to any one of the preceding items [70], [72] to [74] and [77] to [88], wherein non-small cell lung cancer is EGFR gene mutation negative and/or ALK fusion gene negative.

[91] The agent according to any one of the preceding items [1] to [90], wherein tumor mutation burden (hereinafter, abbreviated as "TMB") in the malignant tumor is high frequency (10 mutations or more per $10^6$ bases).

[92] The agent according to any one of the preceding items [1] to [90], wherein TMB in the malignant tumor is low frequency (less than 10 mutations per $10^6$ bases).

[93] The agent according to any one of the preceding items [1] to [92], which is used in combination with other anti-neoplastic drugs.

[94] The agent according to any one of the preceding items [78] to [80] or [93], wherein other anti-neoplastic agents are one or more drugs selected from alkylating agents, platinum preparations, antimetabolites (e.g., antifolate, pyridine metabolism inhibitor and purine metabolism inhibitor), ribonucleotide reductase inhibitors, nucleotide analogs, topoisomerase inhibitors, microtubule polymerization inhibitors, microtubule depolymerization inhibitors, antitumor antibiotics, cytokine preparations, anti-hormonal drugs, molecular targeted drugs, and cancer immunotherapeutic drugs.

[95] The agent according to any one of the preceding items [1] to [94], wherein the patient with malignant tumor is a patient who is prior to administration of a drug containing the substance inhibiting an immune checkpoint as an active ingredient.

[96] An agent for suppressing the progression of, suppressing the recurrence of, and/or treating malignant tumor containing an anti-PD-1 antibody or anti-PD-L1 antibody as an active ingredient, characterized by being administered to a patient with malignant tumor in which a ratio of the PD-1 expression intensity (e.g., MFI) in $CD8^+$ T cells in tumor tissue or blood from the patient with malignant tumor prior to administration of a drug containing the anti-PD-1 antibody or anti-PD-L1 antibody as an active ingredient to the PD-1 expression intensity (e.g., MFI) in Treg cells (Fr. II) in the same tumor tissue or blood is about 0.7 or more;
   wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283, and the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
   wherein the malignant tumor is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[97] An agent for suppressing the progression of, suppressing the recurrence of, and/or treating malignant tumor containing an anti-PD-1 antibody or anti-PD-L1 antibody as an active ingredient, characterized by being administered to a patient with malignant tumor in which either of;
   (a1) a ratio of the PD-1 expression intensity (e.g., MFI) in $CD8^+$ T cells in tumor tissue from the patient with malignant tumor prior to administration of a drug containing the anti-PD-1 antibody or anti-PD-L1 antibody as an active ingredient to the PD-1 expression intensity (e.g., MFI) of Treg cells (Fr. II) in the same tumor tissue, and
   (a2) a ratio of the percentage (%) of the number of PD-1-expressing cells among the same $CD8^+$ T cells to the percentage (%) of the number of PD-1-expressing cells among the same Treg cells (Fr. II),
   is about 1.0 or more, and
   (b) the percentage (%) of the number of PD-1-expressing cells among the same $CD8^+$ T cells is about 40% or more;
   wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283, and the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
   wherein the malignant tumor is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[98] The agent according to any one of the preceding items [1] to [97], wherein the tumor tissue is at least a tumor mass itself, invasive periphery of the tumor, or one containing lymph node adjacent to the tumor.

[1-1] A method for suppressing the progression of, suppressing the recurrence of, and/or treating malignant tumor including administrating an effective amount of an immune checkpoint inhibitor to a patient with malignant tumor in which a ratio of the PD-1 expression intensity in CD8$^+$ T cells in tumor tissue or blood from the patient with malignant tumor to the PD-1 expression intensity in Treg cells in the same tumor tissue or blood is 0.7 or more (or in which it has been confirmed that the ratio is 0.7 or more).

[1-2] A method for suppressing the progression of, suppressing the recurrence of, and/or treating malignant tumor including administrating an effective amount of an immune checkpoint inhibitor to a patient with malignant tumor in which the MFI, measured by flow cytometry, of the PD-1 expression intensity in CD8$^+$ T cells in tumor tissue or blood from the patient with malignant tumor is about 400 or more (or in which it has been confirmed that the MFI is about 400 or more).

[1-3] A method for suppressing the progression of, suppressing the recurrence of, and/or treating malignant tumor including administrating an effective amount of an immune checkpoint inhibitor to a patient with malignant tumor in which a percentage (%) of the number of PD-1-expressing cells among CD8$^+$ T cells in tumor tissue or blood from the patient with malignant tumor is about 35% or more (or in which it has been confirmed that the percentage (%) is about 35% or more).

[1-4] A method for suppressing the progression of, suppressing the recurrence of, and/or treating malignant tumor including administrating an effective amount of an immune checkpoint inhibitor to a patient with malignant tumor in which a percentage (%) of the number of PD-1-expressing cells among Treg cells in tumor tissue or blood from the patient with malignant tumor is less than about 65% (or in which it has been confirmed that the percentage (%) is less than 65%).

[1-5] A method for suppressing the progression of, suppressing the recurrence of, and/or treating malignant tumor including administrating an effective amount of an immune checkpoint inhibitor to a patient with malignant tumor in which either of,
(a1) a ratio of the PD-1 expression intensity in CD8$^+$ T cells in tumor tissue or blood from the patient with malignant tumor to the PD-1 expression intensity in Treg cells in the same tumor tissue or blood, and
(a2) a ratio of the percentage (%) of the number of PD-1-expressing cells among the same CD8$^+$ T cells to the percentage (%) of the number of PD-1-expressing cells among the same Treg cells,
is about 0.8 or more (or in which it has been confirmed that either of the ratios is about 0.8 or more), and
(b) the percentage (%) of the number of PD-1-expressing cells among the same CD8$^+$ T cells is about 35% or more (or in which it has been confirmed that the percentage (%) is about 35% or more).

[1-6] A method for suppressing the progression of, suppressing the recurrence of, and/or treating malignant tumor including administrating an effective amount of an immune checkpoint inhibitor to a patient with malignant tumor in which the numerical value calculated by multiplying the ratio of the PD-1 expression intensity in CD8$^+$ T cells in tumor tissue or blood from the patient with malignant tumor to the PD-1 expression intensity in Treg cells in the same tumor tissue or blood by the percentage (%) of the number of PD-1-expressing cells among the same CD8$^+$ T cells is about 25 or more (or in which it has been confirmed that the percentage (%) is about 25 or more).

[1-7] A method for suppressing the progression of, suppressing the recurrence of, and/or treating malignant tumor including administrating an effective amount of an immune checkpoint inhibitor to a patient with malignant tumor in which the numerical value calculated by dividing the square of the percentage (%) of the number of PD-1-expressing cells among CD8$^+$ T cells in tumor tissue or blood from the patient with malignant tumor by the percentage (%) of the number of PD-1-expressing cells among Treg cells in the same tissue or blood is about 25 or more (or in which it has been confirmed that the numerical value is about 25 or more).

The respective methods in the preceding [1-1] to [1-7] mean a therapeutic method or the like in which an effective amount of the immune checkpoint inhibitor is administered to only a patient with malignant tumor identified based on the respective biomarkers, which may also include the process to identify such a patient.

[2-1] An immune checkpoint inhibitor for use in suppressing the progression and/or recurrence of, and/or treating malignant tumor in a patient with malignant tumor in which a ratio of the PD-1 expression intensity in CD8$^+$ T cells in tumor tissue or blood from the patient with malignant tumor to the PD-1 expression intensity in Treg cells in the same tumor tissue or blood is about 0.7 or more.

[2-2] An immune checkpoint inhibitor for use in suppressing the progression and/or recurrence of, and/or treating malignant tumor in a patient with malignant tumor in which the MFI, measured by flow cytometry, of the PD-1 expression intensity in CD8$^+$ T cells in tumor tissue or blood from the patient with malignant tumor is about 400 or more.

[2-3] An immune checkpoint inhibitor for use in suppressing the progression and/or recurrence of, and/or treating malignant tumor in a patient with malignant tumor in which a percentage (%) of the number of PD-1-expressing cells among CD8⁺ T cells in tumor tissue or blood from the patient with malignant tumor is about 35% or more.

[2-4] An immune checkpoint inhibitor for use in suppressing the progression and/or recurrence of, and/or treating malignant tumor in a patient with malignant tumor in which a percentage (%) of the number of PD-1-expressing cells among Treg cells in tumor tissue or blood from the patient with malignant tumor is less than about 65%.

[2-5] An immune checkpoint inhibitor for use in suppressing the progression and/or recurrence of, and/or treating malignant tumor in a patient with malignant tumor in which either of;
- (a1) a ratio of the PD-1 expression intensity in CD8⁺ T cells in tumor tissue or blood from the patient with malignant tumor to the PD-1 expression intensity in Treg cells in the same tumor tissue or blood, and
- (a2) a ratio of the percentage (%) of the number of PD-1-expressing cells among the same CD8⁺ T cells to the percentage (%) of the number of PD-1-expressing cells among the same Treg cells, is about 0.8 or more, and
- (b) the percentage (%) of the number of PD-1-expressing cells among the same CD8⁺ T cells is about 35% or more.

[2-6] An immune checkpoint inhibitor for use in suppressing the progression and/or recurrence of, and/or treating malignant tumor in a patient with malignant tumor in which the numerical value calculated by multiplying the ratio of the PD-1 expression intensity in CD8⁺ T cells in tumor tissue or blood from the patient with malignant tumor to the PD-1 expression intensity in Treg cells in the same tumor tissue or blood by the percentage (%) of the number of PD-1-expressing cells among the same CD8⁺ T cells is about 25 or more.

[2-7] An immune checkpoint inhibitor for use in suppressing the progression and/or recurrence of, and/or treating malignant tumor in a patient with malignant tumor in which the numerical value calculated by dividing the square of the percentage (%) of the number of PD-1-expressing cells among CD8⁺ T cells in tumor tissue or blood from the patient with malignant tumor by the percentage (%) of the number of PD-1-expressing cells among Treg cells in the same tissue or blood is about 25 or more.

[3-1] Use of a substance inhibiting an immune checkpoint for manufacturing a therapeutic agent to suppress the progression of, suppress the recurrence of, and/or treat malignant tumor, characterized by being administered to a patient with malignant tumor in which a ratio of the PD-1 expression intensity in CD8⁺ T cells in tumor tissue or blood from the patient with malignant tumor to the PD-1 expression intensity in Treg cells in the same tumor tissue or blood is about 0.7 or more.

[3-2] Use of a substance inhibiting an immune checkpoint for manufacturing a therapeutic agent to suppress the progression of, suppress the recurrence of, and/or treat malignant tumor, characterized by being administered to a patient with malignant tumor in which either of;
- (a1) a ratio of the PD-1 expression intensity in CD8⁺ T cells in tumor tissue or blood from the patient with malignant tumor to the PD-1 expression intensity in Treg cells in the same tumor tissue or blood, and
- (a2) a ratio of the percentage (%) of the number of PD-1-expressing cells among the same CD8⁺ T cells to the percentage (%) of the number of PD-1-expressing cells among the same Treg cells, is about 0.8 or more, and
- (b) the percentage (%) of the number of PD-1 expressing cells among the same CD8⁺ T cells is about 35% or more.

[3-3] Use of a substance inhibiting an immune checkpoint for manufacturing a therapeutic agent to suppress the progression of, suppress the recurrence of, and/or treat malignant tumor, characterized by being administered to a patient with malignant tumor in which the numerical value calculated by multiplying the ratio of the PD-1 expression intensity in CD8⁺ T cells in tumor tissue or blood from the patient with malignant tumor to the PD-1 expression intensity in Treg cells in the same tumor tissue or blood by the percentage (%) of the number of PD-1-expressing cells among the same CD8⁺ T cells is about 25 or more.

[3-4] Use of a substance inhibiting an immune checkpoint for manufacturing a therapeutic agent to suppress the progression of, suppress the recurrence of, and/or treat malignant tumor, characterized by being administered to a patient with malignant tumor in which the numerical value calculated by dividing the square of the percentage (%) of the number of PD-1-expressing cells among CD8⁺ T cells in tumor tissue or blood from the patient with malignant tumor by the percentage (%) of the number of PD-1-expressing cells among Treg cells in the same tissue or blood is 25 or more.

[4-1] A method for identifying a patient with malignant tumor on which an effect of immune checkpoint inhibitor can be more expected or a patient with malignant tumor on which any effect of the immune checkpoint inhibitor cannot be expected, based on the following ratio, obtained by collecting a cell population containing Treg cells and CD8⁺ T cells from tumor tissue or blood from the patient with malignant tumor, purifying the cell population if necessary, measuring the respective PD-1 expression intensities in the same Treg cells and CD8⁺ T cells, using flow cytometry, multiple immunohistochemical staining, in situ hybridization, mass cytometry, single cell RNA sequencing, or mass imaging, and determining the ratio of the PD-1 expression intensity in the same CD8⁺ T cells to the PD-1 expression intensity in the same Treg cells.

[4-2] The method according to the preceding item [4-1], identifying a patient having the ratio of about 0.7 or more as a patient with malignant tumor on which the effect of the immune checkpoint inhibitor can be more expected.

[4-3] The method according to the preceding item [4-2], wherein the ratio described in the preceding item [4-2] is about 0.74 or more.

[4-4] The method according to the preceding item [4-2], wherein the ratio described in the preceding item [4-2] is about 0.8 or more.

[4-5] The method according to the preceding item [4-2], wherein the ratio described in the preceding item [4-2] is about 0.9 or more.

[4-6] The method according to the preceding item [4-2], wherein the ratio described in the preceding item [4-2] is about 1.0 or more.

[4-7] The method according to the preceding item [4-2], wherein the ratio described in the preceding item [4-2] is about 1.1 or more.

[4-8] The method according to the preceding item [4-2], wherein the ratio described in the preceding item [4-2] is about 1.2 or more.

[4-9] The method according to the preceding item [4-2], wherein the ratio described in the preceding item [4-2] is about 1.25 or more.

[4-10] The method according to the preceding item [4-2], wherein the ratio described in the preceding item [4-2] is about 1.27 or more.

[4-11] The method according to the preceding item [4-2], wherein the ratio described in the preceding item [4-2] is about 1.3 or more.

[4-12] The method according to the preceding item [4-2], wherein the ratio described in the preceding item [4-2] is about 1.4 or more.

[4-13] The method according to the preceding item [4-2], wherein the ratio described in the preceding item [4-2] is about 1.5 or more.

[4-14] The method according to the preceding item [4-2], wherein the ratio described in the preceding item [4-2] is about 1.6 or more.

[4-15] The method according to the preceding item [4-2], wherein the ratio described in the preceding item [4-2] is about 1.7 or more.

[4-16] The method according to the preceding item [4-2], wherein the ratio described in the preceding item [4-2] is about 1.8 or more.

[4-17] The method according to the preceding item [4-2], wherein the ratio described in the preceding item [4-2] is about 1.9 or more.

[4-18] The method according to the preceding item [4-2], wherein the ratio described in the preceding item [4-2] is an arbitrary ratio between about 0.7 and about 1.9, or more.

[4-19] The method according to any one of the preceding items [4-2] to [4-18], wherein the ratio described in the preceding item [4-2] is an arbitrary ratio between about 2.6 and about 5.9, or less.

[4-20] A method for identifying a patient with malignant tumor on which an effect of immune checkpoint inhibitor can be more expected or a patient with malignant tumor on which any effect of the immune checkpoint inhibitor cannot be expected, based on the following MFI, obtained by collecting a cell population containing $CD8^+$ T cells from tumor tissue or blood from the patient with malignant tumor, purifying the cell population if necessary, and measuring the MFI of PD-1 expression in $CD8^+$ T cells using flow cytometry.

[4-21] The method according to the preceding item [4-20], identifying a patient having the MFI of about 400 or more as a patient with malignant tumor on which the effect of the immune checkpoint inhibitor can be more expected.

[4-22] The method according to the preceding item [4-21], wherein the MFI described in the preceding item [4-21] is about 410 or more.

[4-23] The method according to the preceding item [4-21], wherein the MFI described in the preceding item [4-21] is about 450 or more.

[4-24] The method according to the preceding item [4-21], wherein the MFI described in the preceding item [4-21] is about 500 or more.

[4-25] The method according to the preceding item [4-21], wherein the MFI described in the preceding item [4-21] is about 550 or more.

[4-26] The method according to the preceding item [4-21], wherein the MFI described in the preceding item [4-21] is about 600 or more.

[4-27] The method according to the preceding item [4-21], wherein the MFI described in the preceding item [4-21] is about 650 or more.

[4-28] The method according to the preceding item [4-21], wherein the MFI described in the preceding item [4-21] is about 700 or more.

[4-29] The method according to the preceding item [4-21], wherein the MFI described in the preceding item [4-21] is about 750 or more.

[4-30] The method according to the preceding item [4-21], wherein the MFI described in the preceding item [4-21] is about 800 or more.

[4-31] The method according to the preceding item [4-21], wherein the MFI described in the preceding item [4-21] is about 810 or more.

[4-32] The method according to the preceding item [4-21], wherein the MFI described in the preceding item [4-21] is about 850 or more.

[4-33] The method according to the preceding item [4-21], wherein the MFI described in the preceding item [4-21] is an arbitrary numerical value between about 400 and about 850, or more.

[4-34] The method according to any one of the preceding items [4-21] to [4-33], wherein the MFI of PD-1 expression described in the preceding item [4-21] is an arbitrary numerical value between about 2050 and about 2810, or less.

[4-35] A method for identifying a patient with malignant tumor on which an effect of immune checkpoint inhibitor can be more expected or a patient with malignant tumor on which any effect of the immune checkpoint inhibitor cannot be expected, based on the following percentage, obtained by collecting a cell population containing $CD8^+$ T cells from tumor tissue or blood from the patient with malignant tumor, purifying the cell population if necessary, measuring the number of the same $CD8^+$ T cells and the number of PD-1-expressing cells among them, using flow cytometry or immunostaining, and determining the percentage (%) of the number of PD-1-expressing cells among the same $CD8^+$ T cells.

[4-36] The method according to the preceding item [4-35], identifying a patient having the percentage of about 35% or more as a patient with malignant tumor on which the effect of the immune checkpoint inhibitor can be more expected.

[4-37] The method according to the preceding item [4-36], wherein the percentage described in the preceding item [4-36] is about 40% or more.

[4-38] The method according to the preceding item [4-36], wherein the percentage described in the preceding item [4-36] is about 45% or more.

[4-39] The method according to the preceding item [4-36], wherein the percentage described in the preceding item [4-36] is about 49.7% or more.

[4-40] The method according to the preceding item [4-36], wherein the percentage described in the preceding item [4-36] is about 50% or more.

[4-41] The method according to the preceding item [4-36], wherein the percentage described in the preceding item [4-36] is about 50.7% or more.

[4-42] The method according to the preceding item [4-36], wherein the percentage described in the preceding item [4-36] is about 60% or more.

[4-43] The method according to the preceding item [4-36], wherein the percentage described in the preceding item [4-36] is about 70% or more.

[4-44] The method according to the preceding item [4-36], wherein the percentage described in the preceding item [4-36] is an arbitrary percentage between about 35 and 70%, or more.

[4-45] A method for identifying a patient with malignant tumor on which an effect of immune checkpoint inhibitor can be more expected or a patient with malignant tumor on which any effect of the immune checkpoint inhibitor cannot be expected, based on the following percentage, obtained by collecting a cell population containing Treg cells from tumor tissue or blood from the patient with malignant tumor, purifying the cell population if necessary, measuring the number of the same Treg cells and the number of PD-1-expressing cells among them, using flow cytometry or immunostaining, and determining the percentage (%) of the number of PD-1-expressing cells among the same Treg cells.

[4-46] The method according to the preceding item [4-45], identifying a patient having the percentage of less than about 65% as a patient with malignant tumor on which the effect of the immune checkpoint inhibitor can be more expected.

[4-47] The method according to the preceding item [4-46], wherein the percentage described in the preceding item [4-46] is less than about 60%.

[4-48] The method according to the preceding item [4-46], wherein the percentage described in the preceding item [4-46] is less than about 58.4%.

[4-49] The method according to the preceding item [4-46], wherein the percentage described in the preceding item [4-46] is less than about 55%.

[4-50] The method according to the preceding item [4-46], wherein the percentage described in the preceding item [4-46] is less than an arbitrary percentage between about 65 and about 55%.

[4-51] A method for identifying a patient with malignant tumor on which an effect of immune checkpoint inhibitor can be more expected or a patient with malignant tumor on which any effect of the immune checkpoint inhibitor cannot be expected, based on combination of the ratio in the following (a1) or (a2) and the percentage in the following (b), obtained by;
(i) collecting a cell population containing $CD8^+$ T cells and Treg cells from tumor tissue or blood from the patient with malignant tumor, and purifying the cell population if necessary;
(ii) measuring (iia) the respective PD-1 expression intensities in the same $CD8^+$ T cells and Treg cells or (iib) the respective numbers of the same $CD8^+$ T cells and Treg cells and the respective numbers of PD-1 expressing cells among them, using flow cytometry, immunostaining, multiplex immunohistochemical staining, in situ hybridization, mass cytometry, single-cell RNA sequencing or mass imaging; and
(iii) determining (a1) a ratio of the PD-1 expression intensity in the same $CD8^+$ T cells to the PD-1 expression intensity in Treg cells, or (a2) a ratio of the percentage (%) of the number of PD-1-expressing cells among the same $CD8^+$ T cells to the percentage (%) of the number of PD-1-expressing cells among the same Treg cells, and
(b) the percentage (%) of the number of PD-1-expressing cells among the same $CD8^+$ T cells.

[4-52] The method according to the preceding item [4-51], identifying a patient in which the ratio described in (a1) or (a2) of the preceding item [4-51] is about 0.8 or more, and the percentage described in (b) of the same item is about 35% or more, as a patient with malignant tumor on which the effect of the immune checkpoint inhibitor can be more expected.

[4-53] The method according to the preceding item [4-52], wherein the ratio described in (a1) or (a2) of the preceding item [4-52] is about 0.9 or more.

[4-54] The method according to the preceding item [4-52], wherein the ratio described in (a1) or (a2) of the preceding item [4-52] is about 1.0 or more.

[4-55] The method according to the preceding item [4-52], wherein the ratio described in (a1) or (a2) of the preceding item [4-52] is about 1.1 or more.

[4-56] The method according to the preceding item [4-52], wherein the ratio described in (a1) or (a2) of the preceding item [4-52] is about 1.2 or more.

[4-57] The method according to any one of the preceding items [4-52] to [4-56], wherein the percentage described in (b) of the preceding item [4-52] is about 40% or more.

[4-58] The method according to any one of the preceding items [4-52] to [4-56], wherein the percentage described in (b) of the preceding item [4-52] is about 45% or more.

[4-59] A method for identifying a patent with malignant tumor on which an effect of immune checkpoint inhibitor can be more expected, comprising:
(i) collecting a cell population containing $CD8^+$ T cells and Treg cells from tumor tissue or blood from the patient with malignant tumor, and purifying the cell population if necessary;
(ii) measuring (iia) the respective PD-1 expression intensities in the same $CD8^+$ T cells and Treg cells or (iib) the respective numbers of the same $CD8^+$ T cells and Treg cells and the respective numbers of PD-1 expressing cells among them, using flow cytometry, immunostaining, multiplex immunohistochemical staining, in situ hybridization, mass cytometry, single-cell RNA sequencing or mass imaging; and
(iii) identifying a patient in which either of;
(a1) a ratio of the PD-1 expression intensity in the same $CD8^+$ T cells to the PD-1 expression intensity in the same Treg cells, and
(a2) a ratio of the percentage (%) of the number of PD-1-expressing cells among the same $CD8^+$ T cells to the percentage (%) of the number of PD-1-expressing cells among the same Treg cells,
is about 1.0 or more, and
(b) the percentage (%) of the number of PD-1-expressing cells among the same $CD8^+$ T cells is about 40% or more,
as a patient with malignant tumor on which an effect of immune checkpoint inhibitor can be more expected.

[4-60] A method for identifying a patient with malignant tumor on which an effect of immune checkpoint inhibitor can be more expected or a patient with malignant tumor on which any effect of the immune checkpoint inhibitor cannot be expected, based on the following numerical value obtained by:
(i) collecting a cell population containing $CD8^+$ T cells and Treg cells from tumor tissue or blood from the patient with malignant tumor, and purifying the cell population if necessary;
(ii) measuring the respective PD-1 expression intensities in the same $CD8^+$ T cells and Treg cells and the number of the same $CD8^+$ T cells and the number of PD-1 expressing cells among them, using flow cytometry, immunostaining, multiplex immunohistochemical staining, in situ hybridization, mass cytometry, single-cell RNA sequencing or mass imaging; and
(iii) determining the numerical value calculated by multiplying the ratio of the PD-1 expression intensity in the same $CD8^+$ T cells to the PD-1 expression intensity in the same Treg cells by the percentage (%) of the number of PD-1-expressing cells among the same $CD8^+$ T cells.

[4-61] A method for identifying a patient with malignant tumor on which an effect of immune checkpoint inhibitor can be more expected or a patient with malignant tumor on which any effect of the immune checkpoint inhibitor cannot be expected, based on the following numerical value obtained by:
- (i) collecting a cell population containing CD8$^+$ T cells and Treg cells from tumor tissue or blood from the patient with malignant tumor, and purifying the cell population if necessary;
- (ii) measuring the respective numbers of the same CD8$^+$ T cells and Treg cells and the respective numbers of PD-1 expressing cells among them, using flow cytometry, or immunostaining; and
- (iii) determining the numerical value calculated by dividing the square of the percentage (%) of the number of PD-1-expressing cells among the same CD8$^+$ T cells by the percentage (%) of the number of PD-1-expressing cells among the same Treg cells.

[4-62] The method according to the preceding item [4-60] or [4-61], identifying a patient having the numerical value of about 25 or more, as a patient with malignant tumor on which the effect of the immune checkpoint inhibitor can be more expected.

[4-63] The method according to the preceding item [4-62], identifying the patient in which the numerical value described in the preceding item [4-62] is about 40 or more or about 44.4 or more.

[4-64] The method according to the preceding item [4-62], identifying the patient in which the numerical value described in the preceding item [4-62] is about 46.0 or more or about 50 or more.

[4-65] The method according to the preceding item [4-62], identifying the patient in which the numerical value described in the preceding item [4-62] is about 60 or more.

[4-66] The method according to the preceding item [4-62], identifying the patient in which the numerical value described in the preceding item [4-62] is about 90 or more.

[4-67] The method according to the preceding item [4-62], identifying the patient in which the numerical value described in the preceding item [4-62] is about 100 or more.

[4-68] The method according to any one of the preceding items [4-1] to [4-19] and [4-45] to [4-67], wherein the Treg cells are Treg cells (Fr. II).

[4-69] The method according to any one of the preceding items [4-1] to [4-68], wherein the immune checkpoint inhibitor is an anti-PD-1 antibody, anti-PD-L1 antibody, PD-1 antagonist, PD-L1/VISTA antagonist, PD-L1/TIM3 antagonist, anti-PD-L2 Antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[4-70] The method according to the preceding item s [4-69], wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283.

[4-71] The method according to the preceding item [4-69], wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072.

[4-72] The method according to the preceding item [4-69], wherein the anti-CTLA-4 antibody is Ipilimumab, AGEN1884 or Tremelimumab.

[4-73] The method according to any one of the preceding items [4-1] to [4-72], wherein the malignant tumor is solid cancer or blood cancer.

[4-74] The method according to the preceding item [4-73], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[4-75] The method according to the preceding item [4-73], wherein the blood cancer is one or more cancer(s) selected from multiple myeloma, malignant lymphoma (e.g., non-Hodgkin's lymphoma (e.g., follicular lymphoma, diffuse large B-cell lymphoma, MALT lymphoma, lymphoplasmacytic lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), central nervous system malignant lymphoma, myelodysplastic syndrome and myeloproliferative syndrome.

[4-76] The method according to any one of preceding items [4-1], [4-2], [4-19] and [4-68] to [4-74], wherein in the case that the malignant tumor is non-small cell lung cancer, the ratio described in the preceding item [4-1] is 1.2 or more.

[4-77] The method according to any one of the preceding items [4-20], [4-34], and [4-68] to [4-74], wherein in the case that the malignant tumor is non-small cell lung cancer, the MFI of PD-1 expression described in the preceding item [4-20] is 800 or more.

[4-78] The method according to any one of the preceding items [4-62] and [4-68] to [4-74], wherein in the case that the malignant tumor is non-small cell lung cancer, the numerical value described in the preceding item [4-62] is about 40 or more.

[4-79] The method according to any one of the preceding items [4-1], [4-2], [4-19], [4-19], and [4-68] to [4-74], wherein in the case that the malignant tumor is gastric cancer, the ratio described in the preceding item [4-1] is 0.7 or more.

[4-80] The method according to any one of the preceding items [4-20], [4-34], and [4-68] to [4-74], wherein in the case that the malignant tumor is gastric cancer, the MFI of PD-1 expression described in the preceding item [4-20] is 410 or more.

[4-81] The method according to any one of the preceding items [4-1] to [4-73], wherein the malignant tumor is childhood cancer or unknown primary cancer.

[4-82] The method according to any one of the preceding items [4-1] to [4-81], wherein the malignant tumor is one on which the therapeutic effects of other anti-neoplastic drugs are insufficient or not sufficient.

[4-83] The method of any one of the preceding items [4-1] to [4-82], wherein the malignant tumor is one worsened after treatment with other anti-neoplastic agents.

[4-84] The method according to any one of the preceding items [4-1] to [4-81], wherein the patient with malignant tumor has not been treated with any other anti-neoplastic agents.

[4-85] The method according to any one of the preceding items [4-1] to [4-84], prescribed in a postoperative adjuvant therapy or preoperative adjuvant therapy.

[4-86] The method according to any one of the preceding items [4-1] to [4-85], wherein the malignant tumor is incurable or unresectable, metastatic, recurrent, refractory and/or distant metastatic.

[4-87] The method according to any one of the preceding items [4-1] to [4-86], wherein the TPS or CPS is 50% or more, 25% or more, 5% or more, or 1% or more.

[4-88] The method according to any one of the preceding items [4-1] to [4-86], wherein the TPS or CPS is less than 50%, less than 25%, less than 5% or less than 1%.

[4-89] The method according to any one of the preceding items [4-1] to [4-88], wherein the malignant tumor has MSI-H and/or dMMR.

[4-90] The method according to any one of the preceding items [4-1] to [4-88], wherein the malignant tumor does not have MSI-H and/or dMMR, or has MSI-L.

[4-91] The method according to any one of the preceding items [4-74], [4-76] to [4-78], and [4-81] to [4-90], wherein malignant melanoma or non-small cell lung cancer is BRAF V600E mutation-positive.

[4-92] The method according to any one of the preceding items [4-74], [4-76] to [4-78] and [4-81] to [4-90], wherein malignant melanoma or non-small cell lung cancer is BRAF V600 wild type.

[4-93] The method according to any one of the preceding items [4-74], [4-76] to [4-78] and [4-81] to [4-92], wherein non-small cell lung cancer is EGFR gene mutation positive and/or ALK fusion gene positive.

[4-94] The method according to any one of the preceding items [4-74], [4-76] to [4-78] and [4-81] to [4-92], wherein non-small cell lung cancer is EGFR gene mutation negative and/or ALK fusion gene negative.

[4-95] The method according to any one of the preceding items [4-1] to [4-94], wherein TMB in the malignant tumor is high frequent.

[4-96] The method according to any one of the preceding items [4-1] to [4-94], wherein TMB in the malignant tumor is low frequency.

[4-97] The method according to any one of the preceding items [4-1] to [4-96], wherein the patient with malignant tumor is a patient who is prior to administration of the immune checkpoint inhibitor.

[4-98] A method for identifying a patient with malignant tumor on which an effect of a drug containing an anti-PD-1 antibody or anti-PD-L1 antibody as an active ingredient can be more expected, comprising:
  (i) collecting a cell population containing Treg cells (Fr. II) and CD8$^+$ T cells from tumor tissue or blood from the patient with malignant tumor prior to administration of the drug containing the antibody as an active ingredient, and purifying the cell population if necessary;
  (ii) measuring the respective PD-1 expression intensities in the same Treg cells (Fr. II) and CD8$^+$ T cells, using flow cytometry, immunostaining, multiple immunohistochemical staining, in situ hybridization, mass cytometry, single cell RNA sequencing, or mass imaging; and
  (iii) identifying a patient in which the ratio of the PD-1 expression intensity in the same CD8$^+$ T cells to the PD-1 expression intensity in the same Treg cells (Fr. II) is about 0.7 or more, as a patient on which the effect of the drug can be more expected;
  wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283;
  wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
  wherein the malignant cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[4-99] A method for identifying a patient with malignant tumor on which an effect of a drug containing an anti-PD-1 antibody or anti-PD-L1 antibody as an active ingredient can be more expected, comprising:
  (i) collecting a cell population containing Treg cells (Fr. II) and CD8$^+$ T cells from tumor tissue or blood from the patient with malignant tumor prior to administration of the drug containing the antibody as an active ingredient, and purifying the cell population if necessary;
  (ii) measuring (iia) the respective PD-1 expression intensities in the same CD8$^+$ T cells and Treg cells (Fr. II) or (iib) the respective numbers of the same CD8$^+$ T cells and Treg cells (Fr. II) and the respective numbers of PD-1 expressing cells among them, using flow cytometry, immunostaining, multiplex immunohistochemical staining, in situ hybridization, mass cytometry, single-cell RNA sequencing or mass imaging;
  (iii) identifying a patient in which either of:
  (a1) a ratio of the PD-1 expression intensity in the same CD8$^+$ T cells to the PD-1 expression intensity in the same Treg cells (Fr. II), and
  (a2) a ratio of the percentage (%) of the number of PD-1-expressing cells among the same CD8$^+$ T cells to the percentage (%) of the number of PD-1-expressing cells among the same Treg cells (Fr. II),
  is about 1.0 or more, and
  (b) the percentage (%) of the number of PD-1-expressing cells among the same CD8$^+$ T cells is about 40% or more,
  as a patient on which the effect of the drug can be more expected;
  wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283;
  wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
  wherein the malignant cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[4-100] The method according to any one of the preceding items [4-1] to [4-99], wherein the tumor tissue is at least a tumor mass itself, invasive periphery of the tumor, or one containing lymph node adjacent to the tumor.

[4-101] The method according to any one of the preceding items [4-1] to [4-19] and [4-51] to [4-100], wherein the respective PD-1 expression intensities in the same Treg cells or the Treg cells (Fr. II) and the same CD8$^+$ T cells is represented by the MFI measured by flow cytometry.

[5-1] Use of a ratio of the PD-1 expression intensity in CD8$^+$ T cells in tumor tissue or blood from a patient with malignant tumor to the PD-1 expression intensity in Treg cells in the same tumor tissue or blood, as a biomarker for predicting the effectiveness in suppressing the progression of, suppressing the recurrence of, and/or treating malignant tumor with an immune checkpoint inhibitor.

[5-2] Use of the PD-1 expression intensity in CD8$^+$ T cells in tumor tissue or blood from a patient with malignant tumor, as a biomarker for predicting the effectiveness in suppressing the progression of, suppressing the recurrence of, and/or treating malignant tumor with an immune checkpoint inhibitor.

[5-3] Use of a percentage (%) of the number of PD-1-expressing cells among CD8$^+$ T cells in tumor tissue or blood from a patient with malignant tumor, as a biomarker for predicting the effectiveness in suppressing the progression of, suppressing the recurrence of, and/or treating malignant tumor with an immune checkpoint inhibitor.

[5-4] Use of a percentage (%) of the number of PD-1-expressing cells among Treg cells in tumor tissue or blood from a patient with malignant tumor, as a biomarker for predicting the effectiveness in suppressing the progression of, suppressing the recurrence of, and/or treating malignant tumor with an immune checkpoint inhibitor.

[5-5] Use of combination of:
  (a1) a ratio of the PD-1 expression intensity in CD8$^+$ T cells in tumor tissue or blood from the patient with malignant tumor to the PD-1 expression intensity in Treg cells in the same tumor tissue or blood, or (a2) a ratio of the percentage (%) of the number of PD-1-expressing cells among the same CD8+ T cells to the percentage (%) of the number of PD-1 expressing cells among the same Treg cells, and (b) the percentage (%) of the number of PD-1-expressing cells among the same CD8+ T cells, as a biomarker for predicting the effectiveness in suppressing the progression of, suppressing the recurrence of, and/or treating malignant tumor with an immune checkpoint inhibitor.

[5-6] Use of the numerical value calculated by multiplying the ratio of the PD-1 expression intensity in CD8+ T cells in tumor tissue or blood from a patient with malignant tumor to the PD-1 expression intensity in Treg cells in the same tumor tissue or blood by the percentage (%) of the number of PD-1-expressing cells among the same CD8+ T cells, as a biomarker for predicting the effectiveness in suppressing the progression of, suppressing the recurrence of, and/or treating malignant tumor with an immune checkpoint inhibitor.

[5-7] Use of the numerical value calculated by dividing the square of the percentage (%) of the number of PD-1-expressing cells among CD8+ T cells in tumor tissue or blood from a patient with malignant tumor by the percentage (%) of the number of PD-1-expressing cells among Treg cells in the same tissue or blood, as a biomarker for predicting the effectiveness in suppressing the progression of, suppressing the recurrence of, and/or treating malignant tumor with an immune checkpoint inhibitor.

[5-8] The use according to any one of the preceding items [5-1], [5-2], [5-5] and [5-6], wherein the respective PD-1 expression intensities is represented by the MFI measured by flow cytometry, the expression intensity or expression intensity score measured by multiplex immunohistochemical staining, the signal intensity or expression intensity score measured by in situ hybridization, the expression intensity or signal intensity measured by mass cytometry, the expression level or gene count value measured by single cell RNA sequencing, or the expression intensity or expression intensity score measured by mass imaging.

[5-9] The use according to any one of the preceding items [5-3] to [5-7], wherein the respective numbers of CD8+ T cells and Treg cells in tumor tissue or blood and the respective numbers of PD-1-expressing cells among them are measured by flow cytometry or immunostaining.

[5-10] The use according to any one of the preceding items [5-1] and [5-4] to [5-9], wherein Treg cells are Treg cells (Fr. II).

[5-11] The use according to any one of the preceding items [5-1] to [5-10], wherein the immune checkpoint inhibitor is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[5-12] The use according to the preceding item [5-11], wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283.

[5-13] The use according to the preceding item [5-11], wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072.

[5-14] The use according to the preceding item [5-11], wherein the anti-CTLA-4 antibody is Ipilimumab, AGEN1884 or Tremelimumab.

[5-15] The use according to any one of the preceding items [5-1] to [5-14], wherein the malignant tumor is solid cancer or blood cancer.

[5-16] The use according to the preceding item [5-15], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[5-17] The use according to the preceding item [5-15], wherein the blood cancer is one or more cancers selected from multiple myeloma, malignant lymphoma (e.g., non-Hodgkin's lymphoma (e.g., follicular lymphoma, diffuse large B-cell lymphoma, MALT lymphoma, lymphoplasmacytic lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), central nervous system malignant lymphoma, myelodysplastic syndrome and myeloproliferative syndrome.

[5-18] The use according to any one of the preceding items [5-1] to [5-15], wherein the malignant tumor is childhood cancer or unknown primary cancer.

[5-19] The use according to any one of the preceding items [5-1] to [5-18], wherein the patient with malignant tumor is a patient who is prior to administration of the immune checkpoint inhibitor.

[5-20] Use of a ratio of the PD-1 expression intensity in CD8$^+$ T cells in tumor tissue or blood from a patient with malignant tumor prior to administration of a drug containing an anti-PD-1 antibody or anti-PD-L1 antibody as an active ingredient to the PD-1 expression intensity in Treg cells (Fr. II) in the same tumor tissue or blood, as a biomarker for predicting the effectiveness in suppressing the progression of, suppressing the recurrence of, and/or treating malignant tumor with the same drug;
  wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283;
  wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
  wherein the malignant cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[5-21] Use of combination of:
(a1) a ratio of the PD-1 expression intensity in CD8$^+$ T cells in tumor tissue or blood from a patient with malignant tumor prior to administration of a drug containing an anti-PD-1 antibody or anti-PD-L1 antibody as an active ingredient to the PD-1 expression intensity in Treg cells (Fr. II) in the same tumor tissue or blood, or
(a2) a ratio of the percentage (%) of the number of PD-1-expressing cells among the same CD8$^+$ T cells to the percentage (%) of the number of PD-1-expressing cells among the same Treg cells (Fr. II), and
(b) the percentage (%) of the number of PD-1-expressing cells among the same CD8$^+$ T cells,
as a biomarker for predicting the effectiveness in suppressing the progression of, suppressing the recurrence of, and/or treating malignant tumor with the same drug;
  wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 or JNJ-63723283;
  wherein the anti-PD-L1 antibody is Atezolizumab, Avelumab, Durvalumab, BMS-936559, STI-1014, KN035, LY3300054, HLX20, SHR-1316, CS1001, MSB2311, BGB-A333, KL-A167, CK-301, AK106, AK104, ZKAB001, FAZ053, CBT-502, JS003 or CX-072; and
  wherein the malignant cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[5-22] The use according to any one of the preceding items [5-1] to [5-21], wherein the tumor tissue is at least a tumor mass itself, invasive periphery of the tumor, or one containing lymph node adjacent to the tumor.

Advantage Effects of Invention

By measuring the biomarkers according to the present invention, it becomes possible to identify a patient with malignant tumor on which the effect of the immune checkpoint inhibitor can be more expected.

BRIEF DESCRIPTION OF DRAWINGS

FIG. 1 It shows the ratio of the PD-1 expression MFI of CD8$^+$ T cells to the PD-1 expression MFI of Treg cells derived from a tumor tissue prior to administration of Nivolumab, for each of a patient group with non-small cell lung cancer (7 patients) who showed complete response (CR) or partial response (PR) based on RECIST guideline and a patient group with the same cancer (7 cases) who showed stable disease (SD) or progressive disease (PD) based on the same guideline, for Nivolumab.

FIG. 2 It shows the ratio of the PD-1 expression MFI of CD8$^+$ T cells to the PD-1 expression MFI of Treg cells (Fr. II) derived from a tumor tissue prior to administration of Nivolumab, for each of the patient group with non-small cell lung cancer (7 patients) on which the effect of Nivolumab was CR or PR and the patient group with the same cancer (7 patients) on which it was SD or PD.

FIG. 3 It shows the ratio of the PD-1 expression MFI of CD8$^+$ T cells to the PD-1 expression MFI of Treg cells derived from a tumor tissue prior to administration of Nivolumab, for each of a patient group with gastric cancer (3 patients) on which the effect of Nivolumab was PR and a patient group with the same cancer (14 patients) on which it was SD or PD.

FIG. 4 It shows the ratio of the PD-1 expression MFI of CD8$^+$ T cells to the PD-1 expression MFI of Treg cells (Fr. II) derived from a tumor tissue prior to administration of Nivolumab, for each of the patient group with gastric cancer (3 patients) on which the effect of Nivolumab was PR and the patient group with the same cancer (14 patients) on which it was SD or PD.

FIG. 5 It shows the PD-1 expression MFI values of CD8$^+$ T cells derived from a tumor tissue prior to administration of Nivolumab, for each of the patient group with non-small cell lung cancer (7 patients) on which the effect of Nivolumab was CR or PR and the patient group with the same cancer (7 patients) on which it was SD or PD.

FIG. 6 It shows the PD-1 expression MFI values of CD8$^+$ T cells derived from a tumor tissue prior to administration of Nivolumab, for each of the patient group with gastric cancer (3 patients) on which the effect of Nivolumab was PR and the patient group with the same cancer (14 patients) on which it was SD or PD.

FIG. 7 It shows the PD-1 expression percentage (%) among CD8$^+$ T cell derived from a tumor tissue prior to administration of Nivolumab, for each of the patient group with non-small cell lung cancer (7 patients) on which the effect of Nivolumab was CR or PR and the patient group with the same cancer (7 patients) on which it was SD or PD.

FIG. 8 It shows the PD-1 expression percentage (%) among CD8$^+$ T cells derived from a tumor tissue prior to administration of Nivolumab, for each of the patient group with gastric cancer (3 patients) on which the effect of Nivolumab was PR and the patient group with the same cancer (14 patients) on which it was SD or PD.

FIG. 9 Left panel: it shows the PD-1 expression percentage (%) among CD8$^+$ T cells derived from a tumor tissue prior to administration of Nivolumab, for each of a patient group with non-small cell lung cancer on which the effect of Nivolumab was CR or PR or it was maintained as SD for at least 6 months (the Responder group: 7 patients) and a patient group with the same cancer on which it was maintained as SD only for less than 6 months or it was PD (the Non-Responder group: 5 patients). Right panel: it shows the PD-1 expression percentage (%) among CD8$^+$ T cells derived from a tumor tissue prior to administration of Nivolumab, for each of a patient group with gastric cancer on which the effect of Nivolumab was CR or PR or it was maintained as SD for at least 6 months (the Responder group: 7 patients) and a patient group with the same cancer on which it was maintained as SD only for less than 6 months or it was PD (the Non-Responder group: 16 patients).

FIG. 10 Upper panel: it shows the progression-free survival (PFS) after administration of Nivolumab in the respective patient groups with non-small cell lung cancer (12 patients) divided into two groups, based on the median (52.9%) of the PD-1 expression percentage (%) among CD8$^+$ T cells derived from a tumor tissue. Lower panel: it shows the progression-free survival (PFS) after administration of Nivolumab in the respective patient groups with gastric cancer (23 patients) divided into two groups, based on the median (55.8%) of the PD-1 expression percentage (%) among CD8$^+$ T cells derived from a tumor tissue.

FIG. 11 It shows the PD-1 expression percentage (%) among Treg cells (Fr. II) derived from a tumor tissue prior to administration of Nivolumab, for the Responder group (7 patients) and the Non-Responder group (16 patients), respectively, among the patients with gastric cancer administered with Nivolumab. In the figure, "eTreg" represents Treg cells (Fr. II).

FIG. 12 It shows the progress-free survival (PFS) after administration of Nivolumab, in the respective patient groups of gastric cancer (23 patients) divided into two groups, based on the median (62.3%) of the PD-1 expression percentage (%) among Treg cells (Fr. II) derived from a tumor tissue.

FIG. 13 Left panel: it shows the ratio of the PD-1 expressing MFI of CD8$^+$ T cells to the PD-1 expressing MFI of Treg cells derived from a tumor tissue prior to administration of Nivolumab, for each of the Responder group (7 patients) and the Non-Responder group (5 patients), among the patients with non-small cell lung cancer administered with Nivolumab. Right panel: it shows the ratio of the PD-1 expressing MFI of CD8$^+$ T cells to the PD-1 expressing MFI of Treg cells derived from a tumor tissue prior to administration of Nivolumab, for each of the Responder group (7 patients) and the Non-Responder group (16 patients), among the patients with gastric cancer administered with Nivolumab.

FIG. 14 It shows analysis results to identify the patients on which the effect of Nivolumab can be expected, based on the respective PD-1 expression percentages (%) among Treg cells (Fr. II) and CD8$^+$ T cells derived from tumor tissues from each of patients with non-small cell lung cancer (12 patients) and patients with gastric cancer (23 patients). The PD-1 expression percentage (%) in CD8$^+$ T cells was plotted on horizontal axis, and the PD-1 expression percentage (%) in Treg cells (Fr. II) was plotted on vertical axis. "Group R" is identified as the patient group satisfying the condition that the PD-1 expression percentage (%) among CD8+ T cells is 40% or more, and a ratio of the PD-1 expression percentage (%) in CD8+ T cells to the PD-1 expression percentage (%) in Treg cells (Fr. II) is 1.0 or more.

FIG. 15 It shows analysis results to identify the patients on which the effect of Nivolumab can be expected, based on the respective PD-1 expression MFIs in Treg cells (Fr. II) and CD8+ T cells and the PD-1 expression percentage (%) among the same CD8+ T cells. The PD-1 expression percentage (%) in CD8+ T cells was plotted on horizontal axis, and a ratio of the PD-1 expression MFI in CD8+ T cells to the PD-1 expression MFI in Treg cells (Fr. II) was plotted on vertical axis. "Group R" is identified as the patient group satisfying the condition that the PD-1 expression percentage (%) among CD8+ T cells is 40% or more, and a ratio of the PD-1 expression MFI in CD8+ T cells to the PD-1 expression MFI in Treg cells (Fr. II) is 1.0 or more.

FIG. 16 It shows the progression-free survival (PFS) after administration of Nivolumab, in each of the "Group R" group (the PD-1 expression percentage among CD8+ T cells % 40% and the ratio of the PD-1 expression MFI in CD8+ T cells to the PD-1 expression MFI in Treg cells (Fr. II)=1.0) and the other group of patients ("The other") among cancer patients (12 patients with non-small cell lung cancer and 23 patients with gastric cancer).

FIG. 17 It shows analysis results to identify the patients on which the effect of Nivolumab can be expected, based on the respective PD-1 expression MFIs in Treg cells (Fr. II) and CD8+ T cells derived from a tumor tissue of non-small cell lung cancer (7 patients) and the PD-1 expression percentage (%) among the same CD8+ T cells. The change rate in tumor volume (%) was plotted on horizontal axis, and the numerical value calculated by multiplying a ratio of the PD-1 expression MFI in CD8+ T cells to the PD-1 expression MFI in Treg cells (Fr. II) by the PD-1 expression percentage (%) among CD8+ T cells was plotted on vertical axis.

FIG. 18 It shows analysis results to identify the patients on which the effect of Nivolumab can be expected, based on the respective PD-1 expression percentage (%) among Treg cells (Fr. II) and CD8+ T cells derived from a tumor tissue of non-small cell lung cancer (7 patients). The change rate in tumor volume (%) was plotted on horizontal axis, and the numerical value calculated by dividing the square of PD-1 expression percentage (%) among CD8+ T cells by the PD-1 expression percentage (%) among Treg cells (Fr. II) was plotted on vertical axis. The patient of which the numerical value is extremely low (around 0.0010) is indicated by a broken line frame.

FIG. 19 It shows the respective progression-free survivals (PFS) after administration of Nivolumab for a reference value-positive group (a group having the respective reference values or more: BM+) and a negative group (a group having less than the respective reference values: BM−) when the reference value (CUT) was set to 25, 40, and 60, for patients with non-small cell lung cancer (18 patients).

FIG. 20 It shows the respective progression-free survivals after administration of Nivolumab for a reference value positive group (a group having the respective reference values or more: BM+) and a negative group (a group having less than the respective reference values: BM−) when the reference value (CUT) was set to 90 and 100, for patients with non-small cell lung cancer (18 patients).

FIG. 21 It shows the respective progression-free survivals (PFS) after administration of Nivolumab for a reference value-positive group (a group having the respective reference values or more: BM+) and a negative group (a group having less than the respective reference values: BM−) when the reference value (CUT) was set to 25, 40, and 60, for patients with gastric cancer (29 patients).

FIG. 22 It shows the respective progression-free survivals (PFS) after administration of Nivolumab for a reference value-positive group (a group having the respective reference values or more: BM+) and a negative group (a group having less than the respective reference values: BM−) when the reference value (CUT) was set to 90 and 100, for patients with gastric cancer (29 patients).

FIG. 23 It shows the ratio (left panel) of Biomarker 1 (in the case of Treg cells) and ratio (right panel) of Biomarker 1 (in the case of Treg cells (Fr. II)) of the present inventions prior to administration of Nivolumab, for each of the Responder group (2 patients) and the Non-Responder group (1 patient) of patients with neck cancer administrated with Nivolumab.

FIG. 24 It shows the respective PD-1 expression percentages (%) of Biomarker 3 (left panel) and Biomarker 4 (in the case of Treg cells (Fr. II)) (right panel) of the present inventions prior to administration of Nivolumab, for each of the Responder group (2 patients) and the Non-Responder group (1 patient) of patients with neck cancer administrated with Nivolumab.

FIG. 25 It shows the respective numerical values of Biomarker 6 of the present invention prior to administration of Nivolumab, for the Responder group (2 patients) and the Non-Responder group (1 patient) of patients with head and neck cancer administered with Nivolumab.

FIG. 26 It shows the respective numerical values of Biomarker 7 of the present invention (based on the PD-1 expression percentage (%) in Treg cells (Fr.II)) prior to administration of Nivolumab, for the Responder group (2 patients) and the Non-Responder group (1 patient) of patients with head and neck cancer administered with Nivolumab, respectively.

FIG. 27 It shows the result from which the respective PD-1 expression percentages (%) among CD8+ T cells derived from tumor tissues prior to administration of Nivolumab, for patients with head and neck cancer administered with Nivolumab (3 patients), were plotted on horizontal axis, and the respective PD-1 expression percentages (%) in Treg cells (Fr. II) derived from tumor tissues from the same patient group were plotted on vertical axis. "Group R" represents a region including a patient group satisfying the condition represented by Biomarker 5 of the present invention.

DESCRIPTION OF EMBODIMENTS

In the present specification, the term "substance inhibiting an immune checkpoint" includes, for example, anti-PD-1 antibodies (e.g., Nivolumab, Cemiplimab (REGN-2810), Pembrolizumab (MK-3475), Spartalizumab (PDR-001), Tislelizumab (BGB-A317), AMP-514 (MEDI0680), Dostarlimab (ANB011/TSR-042), Toripalimab (JS001), Camrelizumab (SHR-1210), Genolimzumab (CBT-501), Sintilimab (IBI308), STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188 and JNJ-63723283, etc.), anti-PD-L1 antibodies (e.g., Atezolizumab (RG7446/MPDL3280A), Avelumab (PF-06834635/MSB0010718C), Durvalumab (MEDI4736), BMS-936559, STI-1014, KN035, LY3300054, HLX20, SHR-1316, CS1001 (WBP3155), MSB2311, BGB-A333, KL-A167, CK-301, AK106, AK104, ZKAB001, FAZ053, CBT-502 (TQB2450), JS003 and CX-072, etc.), PD-1 antagonists (e.g., AUNP-12, the respective compounds such as BMS-M1 to BMS-M10 (see WO2014/151634, WO2016/039749, WO2016/057624, WO2016/077518, WO2016/100285, WO2016/100608, WO2016/126646, WO2016/149351, WO2017/151830 and WO2017/176608), BMS-1, BMS-2, BMS-3, BMS-8, BMS-37, BMS-200, BMS-202, BMS-230, BMS-242, BMS-1001, BMS-1166 (see WO2015/034820, WO2015/160641, WO2017/066227 and Oncotarget. 2017 Sep. 22; 8 (42): 72167-72181), the respective compounds of Incyte-1 to Incyte-6 (see WO 2017/070089, WO2017/087777, WO2017/106634, WO 2017/112730, WO 2017/192961 and WO2017/205464), CAMC-1 to CAMC-4 (see WO 2017/202273, WO2017/202274, WO2017/202275 and WO2017/202276), RG_1 (see WO2017/118762) ant DPPA-1 (see Angew. Chem. Int. Ed. 2015, 54, 11760-11764), etc.), PD-L1/VISTA antagonists (e.g., CA-170 etc.), PD-L1/TIM3 antagonists (e.g., CA-327 etc.), anti-PD-L2 antibodies, PD-L1 fusion proteins, PD-L2 fusion proteins (e.g., AMP-224 etc.), anti-CTLA-4 antibodies (e.g., Ipilimumab (MDX-010), AGEN1884 and Tremelimumab, etc.), anti-LAG-3 antibodies (e.g., Relatlimab (BMS-986016/ONO-4482), LAG525, REGN3767 and MK-4280, etc.), LAG-3 fusion proteins (e.g., IMP321 etc.), anti-Tim3 antibodies (e.g., MBG453 and TSR-022, etc.), anti-KIR antibodies (e.g., Lililumab (BMS-986015, ONO-4483), IPH2101, LY3321367 and MK-4280, etc.), anti-BTLA antibodies, anti-TIGIT antibodies (e.g., Tiragolumab (MTIG-7192A/RG-6058/RO-7092284) and BMS-986207 (ONO-4686), anti-VISTA antibody (e.g., JNJ-61610588) and anti-CSF-1R antibody or CSF-1R inhibitor (e.g., Cabiralizumab (FPA008/BMS-986227/ONO-4687), Emactuzumab (RG7155/RO5509554), LY3022855, MCS-110, IMC-CS4, AMG820, Pexidartinib, BLZ945 and ARRY-382, etc.), etc. And, in the present specification, a drug containing these substances as an active ingredient is referred to as "immune checkpoint inhibitor." Nivolumab can be produced according to the method described in WO2006/121168, Pembrolizumab can be produced according to the method described in WO2008/156712, and BMS-936559 can be produced according to the method described in WO2007/005874. And, ipilimumab can be produced according to the method described in WO2001/014424.

The "substance inhibiting an immune checkpoint inhibitor" in the present invention is preferably an anti-PD-1 antibody and anti-PD-L1 antibody. Particularly preferred examples of anti-PD-1 antibodies includes Nivolumab, Cemiplimab, Pembrolizumab, Spartalizumab, Tislelizumab, and Toripalimab, Sintilimab and Camrelizumab, and those of anti-PD-L1 antibodies include Atezolizumab, Avelumab, Durvalumab and BMS-936559.

In the present specification, $CD8^+$ T cells mean T cells which are positive for surface antigen CD8 among T cells, and can be identified as, for example, CD3-positive, CD4-negative, and CD8-positive cells. In the present specification, "positive" means that a certain marker molecule is expressed on cell surface, and that the specific binding of an antibody to the marker molecule at a certain strength can be confirmed, and "negative" means that any specific binding of the antibody to the marker molecule at a certain intensity cannot be confirmed.

In the present invention, Treg cells or regulatory T cells are T cells which exhibit an inhibitory activity against immune response, and can be identified as, for example, CD3-positive, CD4-positive, CD8-negative and FoxP3-positive cells. Among them, "Fraction II Treg cells", "Treg cells (Fr.II)" or "eTreg cells" are effector Treg cells having particularly strong immunosuppressive effects among Treg cells and bearing immunosuppressive activities. They can be identified as CD45RA-negative, CD25-positive and FoxP3-strongly positive Treg cells (see Immunity, Volume 30, Issue 6, 2009, pp. 899-911 and International Immunology, Volume 28, No. 8, 2016, pp. 401.-409).

In the present invention, the "tumor tissue" includes, for example, a tissue containing at least a tumor mass itself, invasive peripheral portions of the tumor or lymph nodes adjacent to the tumor, and can be obtained by known methods, for example, forceps biopsy, fine needle aspiration, needle biopsy, surgical biopsy or surgical operation for removing tumors.

In the present invention, $CD8^+$ T cells and Treg cells may be obtained by mechanically crushing tumor tissues, extracting, and if necessary, further isolating and further purifying the tumor tissues by a known method. The destruction of the tumor tissues may be subjected to enzyme treatment.

In the present invention, "blood" from which $CD8^+$ T cells or Treg cells are collected includes, for example, peripheral blood, and further if necessary, $CD8^+$ T cells and Treg cells in blood may be isolated and further purified by specific gravity centrifugation method and the like.

In the present invention, the number of $CD8^+$ T cells, the number of PD-1-expressing $CD8^+$ T cells, the number of Treg cells, the number of PD-1-expressing Treg cells, and the respective PD-1 expression intensities of $CD8^+$ T cells and Treg cells can be calculated by measuring with, for example, flow cytometry or the like. Specifically, mononuclear cells isolated from tumor tissues, peripheral blood and the like are stained with fluorescent dye-labeled antibodies. Here, the fluorescent dye-labeled antibodies also include unlabeled primary antibodies and fluorescent dye-labeled secondary antibodies corresponding thereto. Mononuclear cells stained with these antibodies are detected by flow cytometry. In addition, the number of $CD8^+$ T cells and the number of PD-1-expressing $CD8^+$ T cells as well as the number of Treg cells and the number of PD-1-expressing Treg cells can also be determined by immunostaining, while the PD-1 expression intensity can be determined by known multiple immunohistochemical staining (e.g., fluorescence or mass-cytometry), in situ hybridization (e.g., FISH, CISH, SISH and DISH), mass cytometry, single cell RNA sequencing or mass imaging. Herein, the PD-1 expression intensity may be defined as the MFI measured by flow cytometry, the expression intensity or expression intensity score measured by multiple immunohistochemical staining, the signal intensity or expression intensity score measured by in situ hybridization, the expression intensity or signal intensity measured by mass cytometry, the expression level or gene count value measured by single cell RNA sequencing, or the expression intensity or expression intensity score measured by mass imaging.

Respective PD-1-expressing $CD8^+$ T cells or respective PD-1-expressing Treg cells, which are measured in Biomarkers 3 to 7, are a cell population expressing PD-1 at a certain threshold or higher, and in, for example, measure by flow cytometry, which is not detected when negative control fluorescent dye-labeled antibodies which does not recognize PD-1 are used or when no fluorescent dye-labeled antibody to PD-1 is used, and which is a cell population having the fluorescence intensity which can be detected in only when fluorescent dye-labeled anti-PD-1 antibodies are used. It should be noted that, in the present specification, the "percentage (%) of the number of PD-1-expressing cells among $CD8^+$ T cells", "percentage (%) of the number of PD-1- expressing cells among Treg cells", and "percentage (%) of the number of PD-1-expressing cells among Treg cells (Fr. II)" may be referred to as the "PD-1 expression percentage (%) among CD8$^+$ T cells", "PD-1 expression percentage (%) among Treg cells", and "PD-1 expression percentage (%) in Treg cells (Fr. II)", respectively.

In the present invention, "prior to administration of a drug containing a substance inhibiting an immune checkpoint as an active ingredient" or "prior to administration of an immune checkpoint inhibitor" includes the case of no history of treatment with the drug containing a substance inhibiting an immune checkpoint as an active ingredient in the past and being administered for the very first time, and further, the case of being prior to administration of the drug in the case that in the past, there is some treatment history with the immune checkpoint inhibitor or other anti-neoplastic agents (including an immune checkpoint inhibitor other than the immune checkpoint inhibitor).

In the present invention, the term "about" used for the respective values calculated from the ratio, percentage, or MFI or a combination thereof, constituting the biomarkers, means that it may change by as much as 10% below or above an indicated value.

The respective biomarkers are measured in patients with malignant tumor prior to administration of an immune checkpoint inhibitor, to which the immune checkpoint inhibitor is administered and then which are divided into a response group and a non-response group, and the reference value (cut-off value) of the biomarker of the present invention can be determined in advance, based on the measured values of the biomarker prior to administration in the respective groups. For example, in the case that the malignant tumor is solid cancer, the determination whether or not it has responded can be determined based on Complete Response: CR, Partial Response: PR, Progressive Disease: PD, Stable Disease: SD which is identified according to the RECIST guideline (Response Evaluation Criteria in Solid Tumor, 2000). For example, it may be determined that a patient diagnosed as CR, PR or SD has responded (in this specification, may be referred to as a "Responder"), and a patient diagnosed as PD has not responded (in this specification, may be referred to as "non-responder"). Alternatively, it may be determined that a patient diagnosed as CR or PR has responded, and a patient diagnosed as SD or PD has not responded. In addition, it may be determined that a patient diagnosed as CR or PR and a patient diagnosed as SD for at least 6 months have responded, and a patient diagnosed as SD for less than 6 months and a patient diagnosed as PD have not responded. The determination based on the same criteria is done at any time from the start of treatment by administration of the immune checkpoint inhibitor, for example, up to 12 months, preferably 10 months, more preferably 8 months, and more preferably 6 months. Whether it has responded or not responded can also be determined based on the overall response rate (ORR), progression-free survival (PFS), overall survival (OS), survival rate, or median survival time.

The reference value (cut-off value) of the biomarkers of the present invention can be determined, for example, by ROC (receiver operating characteristic curve) analysis. The respective biomarkers are measured in a patient with malignant tumor prior to an immune checkpoint inhibitor, to which the immune checkpoint inhibitor is administered and then which are dividing into a response group and a non-response group. Most appropriate value in the ROC analysis can be set by calculating sensitivity and specificity at the respective reference values and plotting them on coordinates with the horizontal axis as specificity and the vertical axis as sensitivity.

Further, the reference value (cut-off value) of the biomarker of the present invention can be set based on, for example, the upper limit or lower limit of 95% confidence intervals calculated in each of the response group and the non-response group. In the case that it is predicted that the same intervals of both groups is clearly separated, it can be set in the separated area between the same intervals of both groups. For example, in the case of Biomarkers 1 to 3, 6, and 7, an arbitrary value between the lower limit of the 95% confidence interval of the response group and the upper limit of the same interval of the non-response group can be set as the reference value. On the other hand, in the case that the same intervals of both groups are not dissociated and a patient on which the therapeutic effect of the immune checkpoint inhibitor can be expected is selected, for example, in the case of Biomarkers 1 to 3, 6 and 7, the lower limit of the 95% confidence interval of the response group can be set as the reference value.

Biomarkers 1 to 3 of the present invention are used in identifying a patient with malignant tumor having more than or equal to the ratio or percentage or the MFI value set in advance as the respective reference values, Biomarker 4 is used in identifying a patient with malignant tumor having less than the percentage set in advance as the reference value, Biomarker 5 is used in identifying a patient with malignant tumor satisfying the condition regarding combination of the reference value set in advance, and Biomarkers 6 and 7 are used in identifying a patient with malignant tumor having more than or equal to the numerical value set in advance as the reference value, as a patient on which the effect of the immune checkpoint inhibitor can be expected. Conversely, they can be used in identify a patient with malignant tumor having less than the same ratio or percentage or the same MFI value set in advance as the respective same reference value (Biomarkers 1 to 3), a patient with malignant tumor having the percentage as the same reference value, or more (Biomarker 4), a patient with malignant tumor not satisfying the condition regarding combination of the same reference value (Biomarker 5), or a patient with malignant tumor having less than the numerical value as the same reference value (Biomarkers 6 and 7), as a patient on which any effect of the immune checkpoint inhibitor cannot be expected.

The reference value (cutoff value) of the ratio referred to as Biomarker 1 in the present invention is an arbitrary ratio between about 0.7 and about 1.9, specifically, about 0.7, about 0.74, about 0.8, about 0.9, about 0.95, about 1.0, about 1.1, about 1.2, about 1.25, about 1.27, about 1.3, about 1.4, about 1.5, about 1.6, about 1.7, about 1.8 or about 1.9. Further, the reference value of the same ratio may have an upper limit having equal to or less than an arbitrary ratio between about 2.6 and about 5.9, if necessary. In particular, in the case of non-small cell lung cancer, the reference value of the same ratio is preferably about 1.2, while in the case of gastric cancer, it is preferably about 0.7. In measuring for calculating the reference value of the same ratio, Treg cells may be limited to a fraction containing Treg cells (Fr. II). Further, the "PD-1 expression intensity" in the same biomarker may be used for calculating the same ratio instead of the number of PD-1 expression (expression amount) per cell. In addition, in determining the number of PD-1 expression per cell, a known measuring method using a fluorescent labeled bead used for preparing a calibration curve for antigen molecule quantification (e.g., BD QuantiBRITE (registered trademark) PE Kit and Quantum (registered trademark) FITC MESF Kit or the like) may be used as appropriate. In addition, as a unit of the expression number (expression amount) of a cell surface antigen molecule used in these measurement methods, for example, Molecules of Equivalent Soluble Fluorochrome (MESF) may be used.

The reference value (cutoff value) of the MFI referred to as Biomarker 2 in the present invention is an arbitrary MFI between about 400 and about 850, and specifically, about 400, about 410, about 450, about 500, about 550, about 600, about 650, about 700, about 750, about 800, about 810 or about 850. Further, the MFI may have an upper limit having equal to or less than an arbitrary MFI between about 2050 to about 2810, if necessary. In particular, in the case of non-small cell lung cancer, the reference value of the MFI is preferably about 800, while in the case of gastric cancer, it is preferably about 410.

The reference value (cutoff value) of the percentage (%) referred to as Biomarker 3 in the present invention is an arbitrary percentage between about 35% and about 70%, and specifically, about 35%, about 36%, about 37%, about 38%, about 39%, about 40%, about 41%, about 42%, about 43%, about 44%, about 45%, about 49.7%, about 50%, about 50.7%, about 51.8, about 56.8%, about 60% or about 70%. In particular, in the case of non-small cell lung cancer, the reference value of the same percentage is preferably an arbitrary percentage between about 49.7 and 51.8%, while in the case of gastric cancer, preferably, it is an arbitrary percentage between about 50.7 and 56.8%.

The reference value (cutoff value) of the percentage (%) referred to as Biomarker 4 in the present invention is an arbitrary percentage between about 65% and about 55%, and specifically, about 65%, about 64%, about 63%, about 62%, about 61%, about 60%, about 59%, about 58.4%, about 58%, about 57%, about 56% or about 55%. In particular, in the case of gastric cancer, the reference value of the same percentage is preferably about 58.4%. Similarly, in measuring for calculating the reference value of the same percentage, Treg cells may be limited to a fraction containing Treg cells (Fr. II).

Biomarker 5 in the present invention, that is, the combination of either of (a1) the ratio of the PD-1 expression intensity in $CD8^+$ T cells in tumor tissue or blood from a patient with malignant tumor to the PD-1 expression intensity in Treg cells in the same tumor tissue or blood or (a2) the ratio of the percentage (%) of the number of PD-1-expressing cells among the same $CD8^+$ T cells to the percentage (%) of the number of PD-1 expressing cells among the same Treg cells and (b) the percentage (%) of the number of PD-1-expressing cells among the same $CD8^+$ T cells can be used in more accurately identifying a patient satisfying the condition of the combined reference value (cutoff value) set in advance, as a patient on which the effect of the immune checkpoint inhibitor can be expected, or a patient not satisfying the same condition, as a patient on which any effect of the immune checkpoint inhibitor cannot be expected.

For example, when the ratio described in the preceding (a1) or (a2) is about 0.8 or more, and the percentage (%) described in the preceding (b) is about 35% or more, about 36% or more, about 37% or more, 38% or more, about 39% or more, about 40% or more, about 41% or more, about 42% or more, about 43% or more, about 44% or more or about 45% or more; when the ratio described in the preceding (a1) or (a2) is about 0.9 or more, and the percentage (%) described in the preceding (b) is about 35% or more, about 36% or more, about 37% or more, about 38% or more, about 39% or more, about 40% or more, about 41% or more, about 42% or more, about 43% or more, about 44% or more or about 45% or more; when the ratio described in the preceding (a1) or (a2) is about 1.0 or more, and the percentage (%) described in the preceding (b) is about 35% or more, about 36% or more, about 37% or more, about 38% or more, about 39% or more, about 40% or more, about 41% or more, about 42% or more, about 43% or more, about 44% or more or about 45% or more; when the ratio described in the preceding (a1) or (a2) is about 1.1 or more, and the percentage (%) described in the preceding (b) is about 35% or more, about 36% or more, about 37% or more, about 38% or more, about 39% or more, about 40% or more, about 41% or more, about 42% or more, about 43% or more, about 44% or more or about 45% or more; or when the ratio described in the preceding (a1) or (a2) is about 1.2 or more, and the percentage (%) described in the preceding (b) is about 35% or more, about 36% or more, about 37% or more, about 38% or more, about 39% or more, about 40% or more, about 41% or more, about 42% or more, about 43% or more, about 44% or more or about 45% or more, it can be identified as a patient on which the effect of the immune checkpoint inhibitor can be expected. That is, more preferably, when the ratio described in the preceding (a1) or (a2) is about 0.9 or more, and the percentage (%) described in the preceding (b) is about 39% or more, about 40% or more, or about 41% or more; when the ratio described in the preceding (a1) or (a2) is about 1.0 or more, and the percentage (%) described in the preceding (b) is about 39% or more, about 40% or more, or about 41% or more; or when the ratio described in the preceding (a1) or (a2) is about 1.1 or more, and the percentage (%) described in the preceding (b) is about 39% or more, about 40% or more, or about 41% or more, further preferably, when the ratio described in the preceding (a1) or (a2) is about 1.0 or more, and the percentage (%) described in the preceding (b) is about 40% or more. Similarly, in measuring for calculating the reference value of the percentage, Treg cells also may be limited to a fraction containing Treg cells (Fr. II). Further, the "PD-1 expression intensity" in the biomarkers may be used for calculating the same ratio, instead of the number of PD-1 expressions (expression amount) per cell.

Biomarker 6 in the present invention, that is, the numerical value calculated by multiplying the ratio of the PD-1 expression intensity in $CD8^+$ T cells in tumor tissue or blood from the patient with malignant tumor to the PD-1 expression intensity in Treg cells in the same tumor tissue or blood by the percentage (%) of the number of PD-1-expressing cells among the same $CD8^+$ T cells can be used in more accurately identifying a patient satisfying the condition of the reference value (cutoff value) set in advance, as a patient on which the effect of the immune checkpoint inhibitor can be expected, or a patient not satisfying the same condition, as a patient on which any effect of the immune checkpoint inhibitor cannot be expected. For example, when the numerical value is about 25 or more, about 40 or more, about 46.0 or more, about 50 or more, about 60 or more, about 90 or more, or about 100 or more, it can be identified as the patient on which the effect of the immune checkpoint inhibitor can be expected, and which is more preferably the case that the numerical value is about 46.0 or more, about 50 or more, about 60 or more, about 90 or more, or about 100 or more.

Biomarker 7 in the present invention, that is, the numerical value calculated by dividing the square of the percentage (%) of the number of PD-1-expressing cells among $CD8^+$ T cells in tumor tissue or blood from the patient with malignant tumor by the percentage (%) of the number of PD-1-expressing cells among Treg cells in the same tissue or blood can be used in more accurately identifying a patient satisfying the condition of the reference value (cutoff value: CUT) set in advance, as a patient on which the effect of the immune checkpoint inhibitor can be expected, or a patient not satisfying the same condition, as a patient on which any effect of the immune checkpoint inhibitor cannot be expected. For example, when the numerical value is about 25 or more, about 40 or more, about 44.4 or more, about 50 or more, about 60 or more, about 90 or more, or about 100 or more, it can be identified as the patient on which the effect of the immune checkpoint inhibitor can be expected, and which is preferably the case of about 40 or more, about 44.4 or more, about 50 or more, about 60 or more, about 90 or more, or about 100 or more, for a patient with non-small cell lung cancer. That is more preferably the case that the numerical value is about 60 or more, about 90 or more, or about 100 or more for any malignant tumors.

[Applicable Diseases and Patients]

Examples of malignant tumors to which the drug or method for identifying a patient of the present invention can be applied, in the case of solid cancer, include, for example, one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

On the other hand, in the case of blood cancer, its examples include, for example, one or more cancers selected from multiple myeloma, malignant lymphoma (e.g., non-Hodgkin's lymphoma (e.g., follicular lymphoma, diffuse large B-cell lymphoma, primary mediastinal B-cell lymphoma, MALT lymphoma, lymphoplasmacytic lymphoma, fungoid mycosis, Sezary syndrome, chronic or acute lymphocytic leukemia, peripheral T cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), central nervous system malignant lymphoma, myelodysplastic syndrome and myeloproliferative syndrome.

In the present specification, examples of the "treatment of malignant tumor" include, for example, therapies (i) to decrease the proliferation of tumor cells, (ii) to reduce symptoms caused by malignant tumor, (iii) to improve the quality of life of a patient with malignant tumor (iv) to reduce the dose of other already administered anti-neoplastic drugs or cancer therapeutic adjuvants and/or (v) to prolong the survival of a patient with malignant tumor. The term "suppressing the progress of malignant tumor" means to delay the progress of malignant tumor, to stabilize symptoms associated with malignant tumor, and to reverse the progress of symptoms. And, the term "suppressing the recurrence of malignant tumor" means to prevent the recurrence of malignant tumor in a patient in which cancer lesion had been completely or substantially eliminated or removed by treatment of malignant tumor or cancer resection surgery.

In the present invention, the immune checkpoint inhibitor can be prescribed to the following malignant tumor patient satisfying the condition of at least one of Biomarkers 1 to 7 according to the present invention, that is, (a) a patient with malignant tumor on which the therapeutic effects of other anti-neoplastic drugs are insufficient or not sufficient or patient with malignant tumor worsened after treatment with other anti-neoplastic agents, (b) a patient with incurable or unresectable, metastatic, recurrent, refractory and/or distant metastatic malignant tumor, (c) a patient with malignant tumor in which TPS or CPS is 50% or more, 25% or more, 10% or more, 5% or 1% or more, (d) a patient with MSI-H or dMMR malignant tumor (e) a patient with BRAF V600E mutation-positive malignant melanoma or non-small cell lung cancer, (f) a patient with EGFR gene mutation-positive or ALK fusion gene-positive malignant tumor, or (g) a patient with malignant tumor with TMB high frequency.

On the other hand, in the present invention, the immune checkpoint inhibitor may be required to be prescribed to the following malignant tumor patient satisfying the condition of at least one of Biomarkers 1 to 7 according to the present invention, that is, (a) a patient with malignant tumor which has not been treated with other anti-neoplastic drugs, (b) a patient with malignant tumor in which TPS or CPS is less than 50%, less than 25%, less than 10%, less than 5% or less than 1%, (c) a patient with malignant tumor without MSI-H and/or dMMR or with MSI-L, (d) a patient with BRAF V600 wild type malignant melanoma or non-small cell lung cancer, (e) a patient with EGFR gene mutation-negative and/or ALK fusion gene-negative non-small cell lung cancer, or (f) a patient with malignant tumor with TMB low frequency.

Furthermore, it can be prescribed as a postoperative adjuvant therapy for preventively suppressing recurrence or metastasis after surgical resection of a malignant tumor or preoperative adjuvant therapy performed before surgical resection.

Herein, examples of "other anti-neoplastic drugs" include the anti-neoplastic drugs listed in the section [combination and combination preparation] below, that are, alkylating agents, platinum preparations, antimetabolite antagonists (e.g., anti-folate, pyridine metabolism inhibitors and purine metabolism inhibitors), ribonucleotide reductase inhibitors, nucleotide analogs, topoisomerase inhibitors, microtubule polymerization inhibitors, microtubule depolymerization inhibitors, antitumor antibiotics, cytokine preparations, anti-hormonal drugs, molecular targeted drugs, and cancer immunotherapeutic drugs. Further, "the therapeutic effects of anti-neoplastic drugs are insufficient or not sufficient" means, for example, the case to be still determined as stable disease (SD) or progressive disease (PD) according to RECIST by even treatment with anti-neoplastic drug.

[Prescription]

The dosage of a substance inhibiting an immune checkpoint according to the present invention varies depending on age, body weight, symptoms, therapeutic effect, administration method, treatment time, etc., but usually it is orally administered at a range from 1 ng to 1000 mg per dose for an adult once to several times per day, or parenterally administered at a range of 0.1 ng to 100 mg per dose for an adult once to several times a day, or continuously administered intravenously for a period ranging from 30 minutes to 24 hours per day. Of course, as described above, since the dose varies depending on various conditions, a dose smaller than the preceding dose may be sufficient, or it may be required to administer it over that range.

For example, in the case of Nivolumab, which is an anti-PD-1 antibody, it is administered with the following usage and dosage, that is, 3 mg/kg (body weight) or 2 mg/kg (body weight) per one dose of Nivolumab may be administered by intravenous drip infusion to a patient with malignant melanoma every 2 weeks or 3 weeks, respectively; or 3 mg/kg (body weight) per one dose of Nivolumab may be administered by intravenous drip infusion every 2 weeks to a patient with non-small cell lung cancer, renal cell cancer, classical Hodgkin's lymphoma, head and neck cancer, gastric cancer, or malignant pleural mesothelioma. Further, as another usage and dose, for example, 240 mg or 480 mg per one dose of Nivolumab may be administered by intravenous drip infusion every 2 weeks or 4 weeks, respectively, to a patient with malignant melanoma, non-small cell lung cancer, renal cell carcinoma, urothelial carcinoma, MSI-H or dMMR-positive colorectal cancer (including a child patient aged 12 years or older), gastric cancer, hepatocellular carcinoma, small cell lung cancer, or malignant pleural mesothelioma. Furthermore, as another usage and dosage, for example, in combination with Ipilimumab, 1 mg/kg (body weight) per one dose of Nivolumab may be administered by intravenous drip infusion to a patient with malignant melanoma 4 times every 3 weeks, and then 3 mg/kg (body weight) per one dose of Nivolumab may be administered by intravenous drip infusion every 2 weeks; or 80 mg per one dose of Nivolumab may be administered by intravenous drip infusion 4 times every 3 weeks, and then 240 mg per one dose of Nivolumab may be administered by intravenous drip infusion every 2 weeks. In addition, for example, to a patient with renal cell cancer, in combination with Ipilimumab, 240 mg per one dose of Nivolumab may be administered by intravenous drip infusion 4 times every 3 weeks, and then 240 mg per one dose of Nivolumab may be administered by intravenous drip infusion every 2 weeks. In the case of Pembrolizumab, which is an anti-PD-1 antibody as well, it is administered in the following usage and dosage: 200 mg per one dose of Pembrolizumab may be administered by intravenous drip infusion every 3 weeks to a patient with malignant melanoma, non-small cell lung cancer, classical Hodgkin's lymphoma, head and neck cancer, MSI-H or dMMR positive solid cancer or colon cancer, urothelial carcinoma, cervical cancer, primary mediastinal B cell lymphoma, liver cell cancer, gastric cancer or Merkel cell carcinoma. Further, as another usage and dosage, for example, 2 mg/kg (body weight) (up to 200 mg at a time) per one dose of Pembrolizumab may be administered by intravenous drip infusion every 3 weeks to a patient with classical Hodgkin's lymphoma in children aged 2 years or older, MSI-H or dMMR-positive solid cancer or colorectal cancer or primary mediastinal B-cell lymphoma.

Further, in the case of Avelumab which is an anti-PD-L1 antibody, 10 mg/kg (body weight) per one dose of Avelumab may be administered by intravenous drip infusion to a patient with Merkel cell carcinoma or urothelial carcinoma every 2 weeks. In the case of Atezolizumab which is an anti-PD-L1 antibody as well, 1200 mg per one dose of Atezolizumab may be administered by intravenous drip infusion every 3 weeks to a patient with non-small cell lung cancer or urothelial carcinoma; or in combination with paclitaxel, 840 mg per one dose of Atezolizumab may be administered by intravenous drip infusion every 2 weeks to a patient with triple negative breast cancer. Furthermore, in the case of Durvalumab which is an anti-PD-L1 antibody as well, 10 mg/kg (body weight) per one dose of Durvalumab may be administered by intravenous drip infusion every 2 weeks to a patient with non-small cell lung cancer or urothelial carcinoma.

In the case of Ipilimumab which is an anti-CTLA-4 antibody, 3 mg/kg (body weight) per one dose of Ipilimumab, in single administration or in combination with Nivolumab, may be administered by intravenous drip infusion to a patient with malignant melanoma per a day 4 times every 3 weeks; or 1 mg/kg (body weight) per one dose of Ipilimumab, in combination with Nivolumab, is administered by intravenous drip infusion to a patient with renal cell carcinoma or MSI-H or dMMR-positive colorectal cancer per a day 4 times every 3 weeks.

[Combination and Combination Preparation]

In order to (1) suppress the progression of, suppress the recurrence of and/or enhance the therapeutic effect on malignant tumor, (2) decrease the dose of other combined drugs, and/or (3) reduce the side effects of other combined drugs, the immune checkpoint inhibitor of the present invention may be used in combination with one or more kinds of other drugs (mainly, anti-neoplastic drug) to be used for the purpose above of treating malignant tumors. In the present invention, the form of formulation in which it is prescribed in combination with other drugs may be that of a combination preparation which both components are mixed in one preparation or that of separated preparations. When administering an immune checkpoint inhibitor and other drugs separately, the immune checkpoint inhibitor may be administered first, followed by administration of other drugs, or other drugs may be administered first, followed by administration of the immune checkpoint inhibitor, and both may be administered simultaneously for a certain period during both administrations. Further, the administration methods of the respective drugs may be the same or different. Depending on the nature of the drug, it can also be provided as a kit containing an immune checkpoint inhibitor and other drugs. Herein, the dose of other drugs can be appropriately selected based on a dose clinically used as a standard. Further, other drugs may be administered in combination of two or more kinds of other drugs at an appropriate ratio. In addition, examples of other drugs include those which would be found in the future, as well as those which have been found to date.

Examples of anti-neoplastic drugs, exemplified as a main example of other drugs, include, for example, alkylating drugs (e.g., Dacarbazine, Nimustine, Temozolomide, Fotemustine, Bendamustine, Cyclophosphamide, Ifosfamide, Carmustine, Chlorambucil, and Procarbazine, etc.), platinum preparations (e.g., Cisplatin, Carboplatin, Nedaplatin and Oxaliplatin, etc.), antimetabolites (e.g., anti-folates (e.g., Pemetrexed, Leucovorin and Methotrexate, etc.), pyridine metabolism inhibitors (e.g., TS-1 (registered trademark), 5-fluorouracil, UFT, Carmofur, Doxifluridine, FdUrd, Cytarabine and Capecitabine, etc.), purine metabolism inhibitors (e.g., Fludarabine, Cladribine and Nelarabine, etc.), ribonucleotide reductase inhibitors, nucleotide analogs (e.g., Gemcitabine etc.), topoisomerase inhibitors (e.g., Irinotecan, Nogitecan and Etoposide, etc.), microtubule polymerization inhibitors (e.g., Vinblastine, Vincristine, Vindesine, Vinorelbine and Eribulin, etc.), microtubule depolymerization inhibitors (e.g., Docetaxel and Paclitaxel), antitumor antibiotics (e.g., bleomycin, Mitomycin C, Doxorubicin, Daunorubicin, Idarubicin, Etoposide, Mitoxantrone, Vinblastine, Vincristine, Peplomycin, Amrubicin, Aclarubicin and Epirubicin, etc.), cytokine preparations (e.g., IFN-α2a, IFN-α2b, Peg IFN-α2b, natural IFN-β and Interleukin-2, etc.), anti-hormonal drugs (e.g., Tamoxifen, Fulvestrant, Goserelin, Leuprorelin, Anastrozole, Letrozole and Exemestane, etc.), molecular targeted drugs, cancer immunotherapeutic drugs and other antibody drugs and the like.

Herein, examples of the molecular target drug include, for example, ALK inhibitors (e.g., Crizotinib, Ceritinib, Ensartinib, Alectinib and Lorlatinib), BCR-ABL inhibitors (e.g., Imatininib and Dasatinib), EGFR inhibitors (e.g., Erlotinib, EGF816, Afatinib, Osimertinib mesilate, Gefitinib and Rociletinib), B-Raf inhibitors (e.g., Sorafenib, Vemurafenib, TAK-580, Dabrafenib, Encorafenib, LXH254, Emurafenib and BGB-3111), VEGFR inhibitors (e.g., Bevacizumab, Apatinib, Lenvatinib, Aflibercept and Axitinib), FGFR inhibitors (e.g., AZD4547, B-701, FGF401 and INCB054828), c-Met inhibitors (e.g., Savolitinib, merestinib, Capmatinib, INC280 and Glesatinib), Axl inhibitors (e.g., ONO-7475 and BGB324), Mek inhibitors (e.g., Cobimetinib, Binimetinib, Selumetinib and Trametinib), CDK inhibitors (e.g., Dinaciclib, Abemaciclib, Palbociclib and trilaciclib), Btk inhibitors (e.g., ONO-4059, Ibrutinib and Acalabrutinib), PI3K-δ/γ inhibitors (e.g., TGR-1202, INCB050465 and IPI-549), JAK-1/2 inhibitors (e.g., Itacitinib and Ruxolitinib), ERK inhibitors (e.g., SCH 900353), TGFbR1 inhibitors (e.g., Galunisertib), Cancer cell stemness kinase inhibitors (e.g., Amcasertib), FAK inhibitors (e.g., Defactinib), Syk/FLT3 dual inhibitors (e.g., TAK-659), ATR inhibitors (eg, AZD6738), Weel kinase inhibitors (e.g., AZD1775), multi-tyrosine kinase inhibitors (e.g., Sunitinib, Pazopanib, Cabozantinib, Regorafenib, Nintedanib, Sitravatinib and Midostaurin), mTOR inhibitors (e.g., Temsirolimus, Everolimus, Vistusertib and Irinotecan), HDAC inhibitors (e.g., Vorinostat, Romidepsin, Entinostat, Chidamide, Mocetinostat, Citarinostat, Panobinostat and Valproate), PARP inhibitors (e.g., Niraparib, Olaparib, Veliparib, Rucaparib and Beigene-290), Aromatase inhibitors (e.g., Exemestane and Letrozole), EZH2 inhibitors (e.g., tazemetostat), Galectin-3 inhibitors (e.g., GR-MD-02), STAT3 inhibitors (e.g., Napabucasin), DNMT inhibitors (e.g., Azacitidine), SMO inhibitors (e.g., Vismodegib), Hsp90 inhibitors (e.g., XL888), γ-tubulin-specific inhibitors (e.g., Glaziovianin A and Plinabulin), HIF2a inhibitors (e.g., PT2385), Glutaminase inhibitors (e.g., CB-839), E3 ligase inhibitors (e.g., Avadomide), Nrf2 activators (e.g., Omaveloxolone), Arginase inhibitors (e.g., CB-1158), cell cycle inhibitors (e.g., Trabectedin), Ephrin B4 inhibitors (e.g., sEphB4-HAS), IAP antagonists (e.g., Birinapant), anti-Her2 antibodies (e.g., Trastuzumab, Trastuzumab emtansine, Pertuzumab and Margetuximab), anti-EGFR antibodies (e.g., Cetuximab, Panitumumab, Necitumumab and Nimotuzumab), Anti-VEGF antibodies (e.g., Bevacizumab), anti-VEGFR2 antibodies (e.g., Ramucirumab), anti-CD20 antibodies (e.g., Rituximab, Ofatumumab, Ublituximab and Obinutuzumab), anti-CD30 antibodies (e.g., Brentuximab Vedotin), anti-CD38 antibodies (e.g., Daratumumab), anti-DR5 antibodies (e.g., DS-8273a), anti-CA125 antibodies (e.g., Oregovomab), anti-DLL4 antibodies (e.g., Demcizumab), anti-fucosyl GM1 antibodies (e.g., BMS-986012), anti-gpNMB antibodies (e.g., Glembatumumab vedotin), anti-Mesothelin antibodies (e.g., BMS-986148), anti-MMP9 antibody (e.g., Andecaliximab), anti-GD2 antibodies (e.g., Dinutuximab-β), anti-c-Met antibodies (e.g., ABT-399), anti-FOLR1 antibodies (e.g., Mirvetuximab soravtansine), anti-Ang2-VEGF bispecific antibodies (e.g., Vanucizumab), Anti-CD30-CD16A bispecific antibodies (e.g., AFM13), anti-CD79b antibody (e.g., Polatuzumab Vedotin), anti-FAP antibody/IL-2 fusion protein (e.g., RO6874281), anti-CEA antibody/IL-2 fusion proteins (e.g., Cergutuzumab amunaleukin), anti-CEA-CD3 bispecific antibodies (e.g., RO6958688), anti-DLL3 antibodies (e.g., Rovalpituzumab tesirine), anti-CD3-CD19 bispecific antibodies (e.g., Blinatumomab), anti-CD20-CD3 bispecific antibodies (e.g., REGN1979) and the like.

In addition, examples of cancer immunotherapeutic drugs include anti-PD-1 antibodies (e.g., Nivolumab, Cemiplimab (REGN-2810), Pembrolizumab (MK-3475), Spartalizumab (PDR-001), Tislelizumab (BGB-A317), AMP-514 (MEDI0680), Dostarlimab (ANB011/TSR-042), Toripalimab (JS001), Camrelizumab (SHR-1210), Genolimzumab (CBT 501), Sintilimab (IBI308), STI-A1110, ENUM 388D4, ENUM 244C8, GLS010, MGA012, AGEN2034, CS1003, BAT 1306, AK105, AK103, BI 754091, LZM009, CMAB819, Sym021, GB226, SSI-361, JY034, HX008, ISU106, ABBV181, BCD-100, PF-06801591, CX-188 and JNJ-63723283, etc.), anti-PD-L1 antibodies (e.g., Atezolizumab (RG7446/MPDL3280A), Avelumab (PF-06834635/MSB0010718C), Durvalumab (MEDI4736), BMS-936559, STI-1014, KN035, LY3300054, SHR-1316, CS1001 (WBP3155), MSB2311, BGB-A333, KL-A167, CK-301, AK106, AK104, ZKAB001, FAZ053, CBT-502 (TQB2450), JS003 and CX-072, etc.), PD-1 antagonists (e.g., AUNP-12, each compound of BMS-M1 to BMS-M10, BMS-1, BMS-2, BMS-3, BMS-8, BMS-37, BMS-200, BMS-202, BMS-230, BMS-242, BMS-1001, BMS-1166, each compound of Incyte-1 to Incyte-6, CAMC-1 to CAMC-4, RG_1 and DPPA-1), PD-L1/VISTA antagonists (e.g., CA-170 etc.), PD-L1/TIM3 antagonists (e.g., CA-327 etc.) Etc.), anti-PD-L2 antibodies, PD-L1 fusion proteins, PD-L2 Fusion proteins (e.g., AMP-224 etc.), anti-CTLA-4 antibodies (e.g., Ipilimumab (MDX-010), AGEN1884 and Tremelimumab, etc.), anti-LAG-3 antibodies (e.g., Relatlimab (BMS-986016/ONO-4482), LAG525, REGN3767 and MK-4280, etc.), LAG-3 fusion proteins (e.g., IMP321 etc.), anti-Tim3 antibodies (e.g., MBG453 and TSR-022, etc.), anti-KIR antibodies (e.g., Lirilumab (BMS-986015/ONO-4483), IPH2101, LY3321367 and MK-4280, etc.), anti-BTLA antibodies, anti-TIGIT antibodies (e.g., Tiragolumab (MTIG-7192A/RG-6058/RO-7092284) and BMS-986207 (ONO-4686)), anti-VISTA antibodies (e.g., JNJ-61610588 etc.), anti-CD137 antibodies (e.g., Urelumab (ONO-4481/BMS-663513) and Utomilumab (PF-05082566), etc.), anti-CSF-1R antibodies or CSF-1R inhibitors (e.g., Cabiralizumab (FPA008/BMS-986227/ONO-4687), Emactuzumab (RG7155/RO5509554), LY3022855, MCS-110, IMC-CS4, AMG820, Pexidartinib, BLZ945 and ARRY-382, etc.), Anti-OX40 antibodies (e.g., MEDI6469, PF-04518600, MEDI0562, MEDI6383, Efizonerimod, GSK3174998, BMS-986178 and MOXR0916, etc.), anti-HVEM antibodies, anti-CD27 antibodies (e.g., Varlilumab (CDX-1127) etc.), anti-GITR antibodies (e.g., MK-4166, INCAGN01876, GWN323 and TRX-518, etc.), anti-CD28 antibody, anti-CCR4 antibodies (e.g., Mogamulizumab etc.), anti-B7-H3 antibodies (e.g., Enoblituzumab etc.), anti-ICOS agonist antibodies (e.g., JTX-2011 and GSK3359609, etc.), anti-CD4 antibodies (e.g., MTRX-1011A, TRX-1, Ibalizumab, huB-F5, Zanolimumab, 4162W94, Clenoliximab, Keliximab, AD-519, PRO-542, Cedelizumab, TNX-355, Dacetuzumab, Tregalizumab, Priliximab, MDX-CD4, CAMPATH-9 and IT1208, etc.), anti-DEC-205 antibody/NY-ESO-1 fusion proteins (e.g., CDX-1401 etc.), anti-SLAMF7 antibodies (e.g., Elotuzumab etc.), anti-CD73 Antibodies (e.g., Oleclumab and BMS-986179, etc.), anti-CD122 antibodies (e.g., NKTR-214 etc.), anti-CD40 agonistic antibodies (e.g., ABBV-428, APX005M and RO7009789, etc.), IDO inhibitors (e.g., Epacadostat, Indoximod and BMS-986205, etc.), TLR agonists (e.g., Motolimod, CMP-001, G100, IMO-2125, SD-101 and MEDI9197, etc.), Adenosine A2A receptor antagonists (e.g., Preladenant, AZD4635, PBF 509 and CPI-444, etc.), anti-NKG2A antibodies (e.g., Monalizumab etc.), anti-CSF-1 antibodies (e.g., PD0360324 etc.), immunopotentiators (e.g., PV-10 etc.), IL-15 superagonists (e.g., ALT-803 etc.), soluble LAG3 (e.g., IMP321 etc.), CD47 antagonists (e.g., ALX148 etc.) and IL-12 antagonists (e.g., M9241 etc.) and the like.

Furthermore, examples of other antibody drugs include for example, anti-IL-1β antibodies (e.g., Canakinumab etc.) and anti-CCR2 antibodies (e.g., Plozalizumab etc.) and the like.

[Preparation]

When administering the substance inhibiting an immune checkpoint or the immune checkpoint inhibitor according to the present invention alone or in combination with other drugs, it is used as an oral solid or oral liquid preparation for oral administration, a sustained-release preparation or controlled-release preparation for oral administration, or a parenteral injection, external preparation, inhalant, suppository or the like for parenteral administration.

Examples for the oral solid preparations for oral administration include, for example, tablets, pills, capsules, powders, granules and the like. Examples of the capsules include hard capsules, soft capsules, and the like.

Such oral solid preparations are used in the form of a formulation containing one or more active substance(s) directly or mixed with excipients (e.g., lactose, mannitol, glucose, microcrystalline cellulose, and starch, etc.), binders (e.g., hydroxypropylcellulose, polyvinylpyrrolidone, and magnesium aluminate metasilicate, etc.), disintegrants (e.g., calcium cellulose glycolate, etc.), lubricants (e.g., magnesium stearate etc.), stabilizers, solubilizing agents (e.g., glutamic acid and aspartic acid, etc.) and the like, according to a conventional method. If necessary, it may be coated with coating agents (e.g., sucrose, gelatin, hydroxypropylcellulose, and hydroxypropylmethylcellulose phthalate, etc.), or may be coated with two or more layers. Further, its examples include capsules comprised by absorbable materials such as gelatin.

Examples of the liquid preparations for oral administration include pharmaceutically acceptable solutions, suspensions, emulsions, syrups and elixirs. In such solutions, one or more active substances are dissolved, suspended or emulsified in a commonly used diluent (e.g., purified water, ethanol, or a mixture thereof). Further, this liquid preparation may contain wetting agents, suspending agents, emulsifying agents, sweetening agents, flavoring agents, fragrances, preservatives, buffering agents or the like.

Further, sustained-release preparations for oral administration are also available. A gel-forming substance used in these sustained-release preparations is a substance which swells in a solvent, connects its colloid particles to each other, forms a three-dimensional network structure, and can form a jelly-like substance which has lost fluidity. It is mainly used as a binder, a thickener and a sustained-release base in pharmaceutical preparations. For example, gum arabic, agar, polyvinylpyrrolidone, sodium alginate, propylene glycol alginate, carboxyvinyl polymer, carboxymethylcellulose, sodium carboxymethylcellulose, guar gum, gelatin, hydroxypropylmethylcellulose, hydroxypropylcellulose, polyvinyl alcohol, methylcellulose or hydroxyethylmethylcellulose can be used.

When formulated and used as an injection or infusion solution for drop infusion, the injection or infusion solution may be in any form of an aqueous solution, suspension or emulsion, and by adding a solvent at the time of use, it may be formulated as a solid preparation together with a pharmaceutically acceptable carrier so that it may be used in the form of a solution, suspension or emulsion. Examples of solvents used for injection or infusion solution for drop infusion include, for example, distilled water for injection, physiological saline, glucose solution and isotonic solution (e.g., a solution of sodium chloride, potassium chloride, glycerin, mannitol, sorbitol, boric acid, borax, propylene glycol, or the like).

Herein, examples of pharmaceutically acceptable carriers include, for example, stabilizers, dissolution aids, suspending agents, emulsifiers, soothing agents, buffering agents, preservatives, antiseptic agents, pH adjusters, antioxidants, and the like. As the stabilizer, for example, various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, dibutylhydroxytoluene or the like can be used. As the dissolution aids, for example, alcohols (e.g., ethanol), polyalcohols (e.g., propylene glycol and polyethylene glycol, etc.), nonionic surfactants (e.g., Polysorbate 20 (registered trademark), polysorbate 80 (registered trademark) and HCO-50, etc.) can be used. As the suspending agents, for example, glyceryl monostearate, aluminum monostearate, methyl cellulose, carboxymethyl cellulose, hydroxymethyl cellulose, sodium lauryl sulfate or the like can be used. As the emulsifiers, for example, gum arabic, sodium alginate, tragacanth or the like can be used. As the soothing agents, for example, benzyl alcohol, chlorobutanol, sorbitol or the like can be used. As the buffering agents, for example, a phosphate buffer, acetate buffer, borate buffer, carbonate buffer, citrate buffer, Tris buffer, glutamate buffer, epsilon aminocaproate buffer, or the like can be used. As the preservatives, for example, methyl paraoxybenzoate, ethyl paraoxybenzoate, propyl paraoxybenzoate, butyl paraoxybenzoate, chlorobutanol, benzyl alcohol, benzalkonium chloride, sodium dehydroacetate, sodium edetate, boric acid, borate sand or the like can be used. As the antiseptic agents, for example, benzalkonium chloride, paraoxybenzoic acid, chlorobutanol or the like can be used. As the pH adjustors, for example, hydrochloric acid, sodium hydroxide, phosphoric acid, acetic acid or the like can be used. As the antioxidants, (1) water-soluble antioxidants such as ascorbic acid, cysteine hydrochloride, sodium bisulfate, sodium metabisulfite, sodium sulfite and the like, (2) oil-soluble antioxidants such as ascorbyl palmitate, butylated hydroxyanisole, butylated hydroxytoluene, lecithin, propyl gallate, α-tocopherol and the like, and (3) metal chelating agents such as citric acid, ethylenediaminetetraacetic acid, sorbitol, tartaric acid, phosphoric acid and the like can be used.

The injections or infusion solutions for drop infusion can be manufactured by sterilizing in the final step or sterilizing by a sterile operation method, for example, filtering by a filter or the like, and then filling in a sterile container. The injections or infusion solutions for drop infusion are prepared by dissolving a sterile powder (which may contain a pharmaceutically acceptable carrier powder) by vacuum drying and freeze-drying in a suitable solvent before use.

Examples of the form of external preparation for parenteral administration include, for example, an aerosol preparation, inhalant preparation, spray preparation, aerosol preparation, ointment preparation, gel preparation, cream preparation, compress preparation, patch preparation, liniment preparation and nasal drop preparation. They contain one or more active substances and are prepared by known methods or commonly used formulations.

The aerosol preparation, inhalant preparation and spray preparation may contain stabilizers such as sodium bisulfite and buffering agents to give isotonicity, for example, isotonic agents such as sodium chloride, sodium citrate and citric acid, other than commonly used diluents. The method for producing sprays is described in detail, for example, in U.S. Pat. Nos. 2,868,691 and 3,095,355.

Examples of inhalant preparation for parenteral administration include aerosol preparations, powder preparations for inhalation, and liquid preparations for inhalation, and the liquid preparations for inhalation may be in the form of which it is dissolved or suspended in water or other suitable medium before use.

These inhalant preparations are manufactured according to known methods. For example, in the case of the liquid preparation for inhalation, antiseptic agents (e.g., benzalkonium chloride and paraben, etc.), coloring agents, buffering agents (e.g., sodium phosphate and sodium acetate, etc.), tonicity agents (e.g., sodium chloride and concentrated glycerin, etc.), thickeners (e.g., carboxyvinyl polymer etc.), absorption enhancers or the like are appropriately selected and prepared as needed.

In the case of powder preparations for inhalation, lubricants (e.g., stearic acid and salts thereof, etc.), binders (e.g., starch and dextrin, etc.), excipients (e.g., lactose and cellulose, etc.), coloring agents, antiseptic agents (e.g., benzalkonium chloride and paraben, etc.), absorption enhancers or the like is appropriately selected and prepared as needed.

When administering a liquid preparation for inhalation, a nebulizer (e.g., atomizer and nebulizer, etc.) is usually used and when administering a powder preparation for inhalation, an inhaler for powdered drug is usually used.

The ointment is produced as a known or commonly used formulation. For example, it is prepared by mixing or melting one or more active substances in a base. The ointment base is selected from known or commonly used ones. For example, any one selected from higher fatty acids or higher fatty acid esters (e.g., adipic acid, myristic acid, palmitic acid, stearic acid, oleic acid, adipic acid ester, myristic acid ester, palmitic acid ester, stearic acid ester and oleic acid ester, etc.), waxes (e.g., beeswax, spermaceti and ceresin, etc.), surfactants (e.g., polyoxyethylene alkyl ether phosphate etc.), higher alcohols (e.g., cetanol, stearyl alcohol and cetostearyl alcohol, etc.), silicone oils (e.g., dimethylpolysiloxane etc.), hydrocarbons (e.g., hydrophilic petrolatum, white petrolatum, purified lanolin and liquid paraffin, etc.), glycols (e.g., ethylene glycol, diethylene glycol, propylene glycol and polyethylene glycol and macrogol, etc.), vegetable oils (e.g., castor oil, olive oil, sesame oil and turpentine oil, etc.), animal oils (e.g., mink oil, egg yolk oil, squalene and squalene, etc.), water, absorption enhancers and anti-rash agents are used alone or in combination of two or more kinds. Further, it may contain a humectant, preservative, stabilizer, antioxidant or flavoring agent.

The gel is produced as a known or commonly used formulation. For example, it is prepared by melting one or more active substances in a base. The gel base is selected from known or commonly used ones. For example, any one selected from lower alcohols (e.g., ethanol and isopropyl alcohol, etc.), gelling agents (e.g., carboxymethylcellulose, hydroxyethylcellulose, hydroxypropylcellulose and ethylcellulose, etc.), neutralizing agents (e.g., triethanolamine and diisopropanolamine, etc.), surfactants (e.g., polyethylene glycol monostearate etc.), gums, water, absorption enhancers and rash preventives are used alone or in combination of two or more. Further, it may contain a preservative, antioxidant or flavoring agent.

The cream is produced as a known or commonly used formulation. For example, it is produced by melting or emulsifying one or more active substances in a base. The cream base is selected from known or commonly used ones. For example, any one selected from higher fatty acid esters, lower alcohols, hydrocarbons, polyhydric alcohols (e.g., propylene glycol, 1,3-butylene glycol, etc.), higher alcohols (e.g., 2-hexyldecanol and cetanol, etc.), emulsifiers (e.g., polyoxyethylene alkyl ethers and fatty acid esters, etc.), water, absorption enhancers and rash preventive agents are used alone or in combination of two or more kinds. Further, it may contain a preservative, antioxidant or flavoring agent.

The poultice is produced by a known or commonly used formulation. For example, it is manufactured by melting one or more active substances in a base material, forming a kneaded product, and spreading and coating the mixture on a support. The poultice base is selected from known or commonly used ones. For example, thickeners (e.g., polyacrylic acid, polyvinylpyrrolidone, gum arabic, starch, gelatin, methylcellulose, etc.), wetting agents (e.g., urea, glycerin, propylene glycol, etc.), fillers (e.g., kaolin, zinc oxide, talc, calcium, magnesium, etc.), water, dissolution aid, tackifier, and anti-rash agent is/are used alone or in combination of two or more. Further, it may contain a preservative, antioxidant or flavoring agent.

The patch is produced by a known or commonly used formulation. For example, it is produced by melting one or more active substances in a base material, and spreading and coating on a support. The base for the patch is selected from known or commonly used ones. For example, those selected from a polymer base, oil and fat, higher fatty acid, tackifier and anti-rash agent is/are used alone or in combination of two or more. Further, it may contain a preservative, antioxidant or flavoring agent.

The liniment is manufactured by a known or commonly used formulation. For example, it is prepared by making one or more active substances dissolved, suspended or emulsified in alone or in combination of two or more selected from water, alcohols (e.g., ethanol, polyethylene glycol, etc.), higher fatty acid, glycerin, soap, emulsifier and suspending agent. Further, it may contain a preservative, antioxidant or flavoring agent.

Other compositions for parenteral administration include suppositories for rectal administration and pessaries for vaginal administration, which contain one or more active substances and are formulated in a conventional manner.

[Test/Measurement Kit]

The present invention also includes tests or measurement kits for measuring an index constituting Biomarkers 1 to 7 according to the present invention, respectively. For example, when the PD-1 expression intensity is measured, the test or measurement kit is based on flow cytometry, multiple immunohistochemical staining (e.g., fluorescence or mass cytometry), in situ hybridization (e.g., FISH, CISH, SISH and DISH), mass cytometry, single cell RNA sequencing or mass imaging. On the other hand, when the number of CD8+ T cells, the number of PD-1-expressing CD8+ T cells, the number of Treg cells or the number of PD-1-expressing Treg cells is measured, it may be based on flow cytometry or immunostaining. In any case, the tests or measurement kits based on flow cytometry is preferred.

In this specification, the contents of all patent documents and non-patent documents or references explicitly cited may be incorporated herein as a part of the present specification. The present invention will be described in more detail with reference to the following examples, but the scope of the present invention is not limited thereto. Various changes and modifications can be made by those skilled in the art based on the description of the present invention, and these changes and modifications are also included in the present invention.

EXAMPLE

Example 1: Collection of Lymphocytes from Tumor Tissue and Identification of T Cells by Flow Cytometry Tumor tissues were collected from cancer patients prior to administration of Nivolumab, and tumor infiltrating lymphocytes were separated by fracturing the tissues with gentleMACS Dissociator (MiltenyiBiotec). Peripheral blood mononuclear cells were prepared from peripheral blood from the same patient prior to administration of the substance inhibiting an immune checkpoint by density gradient centrifugation using Ficoll. The tumor-infiltrating lymphocytes and peripheral blood mononuclear cells after separation were suspended in PBS containing fetal bovine serum at 2% as the final concentration (hereinafter, referred to as "FACSBuffer"), and then to which Human Fc-Receptor Binding Inhibitor (ThermoFisher) was added, and the mixture of which was stored at 4° C. for 10 minutes. Thereafter, the fluorescent-labeled antibodies to various cell surface markers (CD3, CD8, CD4, CD45RA and PD-1) were added thereto, and then the mixture of which was stored at 4° C. for 15 minutes. After washing with FACS Buffer, the cells were fixed and permeabilized using Foxp3/Transcription Factor Staining Buffer Set (ThermoFisher), and to which the fluorescent-labeled antibodies to intracellular protein FoxP3 was added, and the mixture of which was stored at 4° C. for 30 minutes. After washing with FACS Buffer, the expressions of the respective proteins were analyzed with LSRFortessa X-20 (Becton Dickinson).

In the present example, among the collected lymphocyte cells, CD3-positive, CD4-positive, CD8-negative and FoxP3-positive cells were defined as Treg cells, and CD3-positive, CD4-positive, CD8-negative, CD45RA-negative and FoxP3-strong positive cells were defined as Treg cells (Fr. II), and CD3-positive, CD4-negative and CD8-positive cells were defined as CD8+ T cells.

Example 2: Evaluation of Biomarkers for Determining the Effectiveness of Nivolumab Based on the Respective PD-1 Expression Intensities in Treg Cells and CD8+ T Cells (Non-Small Cell Lung Cancer)

The respective PD-1 expression intensities in Treg cells, Treg cells (Fr. II) and CD8+ T cells derived from tumor tissues from 15 patients with non-small cell lung cancer prior to administration of Nivolumab were measured by flow cytometry, and their average fluorescence intensities (MFI) were calculated.

Among the patients with non-small cell lung cancer, 7 patients showed the effects identified as CR or PR by Nivolumab administration, and 7 patients showed SD or PD. The remaining one patient could not be evaluated, and was excluded from the following evaluations.

FIGS. 1 and 2 show the respective results about the ratios of the PD-1 expression MFI in CD8+ T cells to the PD-1 expression MFI in Treg cells and Treg cells (Fr. II), calculated in each of a patient group showing CR or PR (hereinafter, referred to as "CR/PR group") and a patient group showing SD or PD (hereinafter, referred to as "SD/PD group"). Furthermore, the upper and lower limits of the 95% confidence interval were calculated based on the average value and standard deviation of the same ratios in the respective groups. Table 1 shows its results.

TABLE 1

| Ratio A | | | |
|---|---|---|---|
| | Mean ± S.D. | Upper Limit (95% Confidence Interval) | Lower Limit (95% Confidence Interval) |
| CR/PR Group | 2.15 ± 0.46 | 2.58 | 1.72 |
| SD/PD Group | 1.01 ± 0.28 | 1.27 | 0.75 |
| Ratio B | | | |
| | Mean ± S.D. | Upper Limit (95% Confidence Interval) | Lower Limit (95% Confidence Interval) |
| CR/PR Group | 2.13 ± 0.45 | 2.55 | 1.72 |
| SD/PD Group | 0.99 ± 0.28 | 1.25 | 0.74 |

In this table, Ratio A indicates the ratio of PD-1 expression MFI in CD8+ T cells to the PD-1 expression MFI in Treg cells, and Ratio B indicates the ratio of PD-1 expression MFI in CD8 T cells to the PD-1 expression MFI in Treg cells (Fr. II).

As described above, in the case that for Ratio A, the upper limit value 1.27 of the SD/PD group was set as the reference value (cutoff value), while for Ratio B, the upper limit value 1.25 of the SD/PD group was set as the reference value, for example, a patient with non-small cell lung cancer exhibiting the ratio which is the same value or more can be identified as a patient on which the effect of Nivolumab can be more expected.

Example 3: Evaluation of Biomarkers for Determining the Effectiveness of Nivolumab, Based on the Respective PD-1 Expression Intensities in Treg Cells and CD8+ T Cells (Gastric Cancer)

The respective PD-1 expression intensities in Treg cells, Treg cells (Fr. II) and CD8+ T cells derived from tumor tissues from 17 patients with gastric cancer prior to administration of Nivolumab were measured by flow cytometry, and their MFIs were calculated.

Among the patients with gastric cancer, 3 patients showed the effects identified as PR by Nivolumab administration, and 14 patients showed SD or PD.

FIGS. 3 and 4 show the respective results about the ratios of the PD-1 expression MFI in CD8+ T cells to the PD-1 expression MFI in Treg cells and Treg cells (Fr. II), calculated in a patient group showing PR and the "SD/PD group". Furthermore, the upper and lower limits of the 95% confidence interval were calculated based on the average value and standard deviation of the same ratios in the respective groups. Table 2 shows its results.

TABLE 2

| Ratio A | | | |
|---|---|---|---|
| | Mean ± S.D. | Upper Limit (95% Confidence Interval) | Lower Limit (95% Confidence Interval) |
| PR Group | 1.79 ± 1.40 | 5.26 | 1.68 |
| SD/PD Group | 0.61 ± 0.22 | 0.74 | 0.48 |

| Ratio B | | | |
|---|---|---|---|
| | Mean ± S.D. | Upper Limit (95% Confidence Interval) | Lower Limit (95% Confidence Interval) |
| PR Group | 1.91 ± 1.57 | 5.82 | 1.99 |
| SD/PD Group | 0.59 ± 0.20 | 0.70 | 0.47 |

In this table, Ratio A indicates the ratio of PD-1 expression MFI in $CD8^+$ T cells to the PD-1 expressing MFI in Treg cells, and Ratio B indicates the ratio of PD-1 expression MFI in $CD8^+$ T cells to the PD-1 expression MFI in Treg cells (Fr. II).

As described above, in the case that for Ratio A, the upper limit value 0.74 of the SD/PD group was set as the reference value, while for Ratio B, the upper limit value 0.70 of the SD/PD group was set as the reference value, for example, a patient with gastric cancer exhibiting the ratio which is the same value or more can be identified as a patient on which the effect of Nivolumab can be more expected.

Example 4: Evaluation of a Biomarker for Determining the Effectiveness of Nivolumab, Based on the PD-1 Expression Intensity in $CD8^+$ T Cells (Non Small Cell Lung Cancer)

The PD-1 expression intensities in $CD8^+$ T cells derived from tumor tissues from 15 patients with non-small cell lung cancer prior to administration of Nivolumab (the same patient group in Example 2) were measured by flow cytometry, and their MFIs were calculated.

FIG. 5 shows the respective results of the same MFIs calculated in the CR/PR group and the SD/PD group. Furthermore, the upper and lower limits of the 95% confidence interval were calculated based on the mean and standard deviation of the same MFIs in the respective groups. Table 3 shows its results.

TABLE 3

| | Mean ± S.D. | Upper Limit (95% Confidence Interval) | Lower Limit (95% Confidence Interval) |
|---|---|---|---|
| CR/PR Group | 1643 ± 434 | 2045 | 1242 |
| SD/PD Group | 559 ± 268 | 807 | 312 |

As described above, in the case that the upper limit value 807 of the SD/PD group was set as the reference value, for example, a patient with non-small cell lung cancer exhibiting the MFI which is the same value or more can be identified as a patient on which the effect of Nivolumab can be more expected.

Example 5: Evaluation of a Biomarker for Determining the Effectiveness of Nivolumab Based on the PD-1 Expression Intensity in $CD8^+$ T Cells (Gastric Cancer)

The PD-1 expression intensities in $CD8^+$ T cells derived from tumor tissues from 17 patients with gastric cancer prior to administration of Nivolumab (the same patient group in Example 3) were measured by flow cytometry, and their MFIs were calculated.

FIG. 6 shows the respective results of the same MFIs calculated in the PR group and the SD/PD group. Furthermore, the upper and lower limits of the 95% confidence interval were calculated based on the mean and standard deviation of the same MFIs in the respective groups. Table 4 shows its results.

TABLE 4

| | Mean ± S.D. | Upper Limit (95% Confidence Interval) | Lower Limit (95% Confidence Interval) |
|---|---|---|---|
| PR Group | 977 ± 738 | 2809 | 855 |
| SD/PD Group | 335 ± 130 | 410 | 260 |

As described above, in the case that the upper limit value 410 of the SD/PD group was set as the reference value, for example, a patient with gastric cancer exhibiting the MFI which is the same value or more can be identified as a patient on which the effect of Nivolumab can be more expected.

Example 6: Evaluation of a Biomarker for Determining the Efficacy of Nivolumab, Based on the PD-1 Expression Percentage Among $CD8^+$ T Cells (1) (Non-Small Cell Lung Cancer)

The number of PD-1-expressing $CD8^+$ T cells derived from tumor tissues from 15 patients with non-small cell lung cancer prior to administration of Nivolumab (the same patient group in Example 2) were measured by flow cytometry, and the PD-1 expression percentages (%) among $CD8^+$ T cells were calculated.

FIG. 7 shows the respective results of the same percentages calculated in the CR/PR group and the SD/PD group. Furthermore, the upper and lower limits of the 95% confidence interval were calculated based on the mean and standard deviation of the same percentages in the respective groups. Table 5 shows its results.

TABLE 5

| | Mean ± S.D. | Upper Limit (95% Confidence Interval) | Lower Limit (95% Confidence Interval) |
|---|---|---|---|
| CR/PR Group | 87.7 ± 18.5 | 104.8 | 70.6 |
| SD/PD Group | 29.6 ± 21.7 | 49.7 | 9.5 |

As described above, in the case that the upper limit value 49.7 of the SD/PD group was set as the reference value, for example, a patient with non-small cell lung cancer exhibiting the PD-1 expression percentage which is the same value or more can be identified as a patient on which the effect of Nivolumab can be more expected.

Example 7: Evaluation of a Biomarker for Determining the Effectiveness of Nivolumab, Based on the PD-1 Expression Percentage Among CD8+ T Cells (1) (Gastric Cancer)

The number of PD-1-expressing CD8+ T cells derived from tumor tissues from 17 patients with gastric cancer prior to administration of Nivolumab (the same patient group in Example 3) were measured by flow cytometry, and the PD-1 expression percentages (%) among CD8+ T cells were calculated.

FIG. 8 shows the respective results of the same percentages calculated in the PR group and the SD/PD group. Furthermore, the upper and lower limits of the 95% confidence interval were calculated based on the mean and standard deviation of the same percentages in the respective groups. Table 6 shows its results.

TABLE 6

|  | Mean ± S.D. | Upper Limit (95% Confidence Interval) | Lower Limit (95% Confidence Interval) |
|---|---|---|---|
| PR Group | 74.6 ± 9.6 | 98.6 | 50.7 |
| SD/PD Group | 48.6 ± 10.5 | 54.7 | 42.5 |

As described above, in the case that the lower limit value 50.7 of the PR group was set as the reference value, for example, a patient with gastric cancer exhibiting the PD-1 expression percentage which is the same value or more can be identified as a patient on which the effect of Nivolumab can be more expected.

Example 8: Evaluation of Biomarkers for Determining the Effectiveness of Nivolumab, Based on the PD-1 Expression Percentage Among CD8+ T Cells (2) (Non Small Cell Lung Cancer: NSCLC)

The number of PD-1-expressing CD8+ T cells derived from tumor tissues from 12 patients with non-small cell lung cancer prior to administration of Nivolumab were measured by flow cytometry, and the PD-1 expression percentages (%) among CD8+ T cells were calculated.

The left panel in FIG. 9 shows the results of the same percentages calculated in the Responder group (patients showing CR and PR and ones maintaining SD for at least 6 months: 7 patients) and the Non-Responder group (patients maintaining SD only for less than 6 months and ones showing PD: 5 patients). Furthermore, the upper and lower limits of the 95% confidence interval were calculated based on the mean and standard deviation of the same percentages in the respective groups. Table 7 shows its results.

TABLE 7

|  | Mean ± SD | Upper Limit (95% Confidence Interval) | Lower Limit (95% Confidence Interval) |
|---|---|---|---|
| Responder Group | 78.9 ± 20.5 | 97.9 | 59.9 |
| Non-responder Group | 29.6 ± 17.8 | 51.8 | 7.5 |

As described above, in the case that the upper limit value 51.8 of the Non-Responder group was set as the reference value, for example, a patient with non-small cell lung cancer exhibiting the PD-1 expression percentage which is the same value or more can be identified as a patient on which the effect of Nivolumab can be more expected.

The same patients with non-small cell lung cancer were divided into two groups, based on the median PD-1 expression ratio (52.9%). The upper panel in FIG. 10 shows the result of progression-free survival (PFS) calculated in the respective groups.

Example 9: Evaluation of Biomarkers for Determining the Effectiveness of Nivolumab, Based on the PD-1 Expression Percentage in CD8+ T Cells (2) (Gastric Cancer: GC)

The number of PD-1-expressing CD8+ T cells derived from tumor tissues from 23 patients with gastric cancer prior to administration of Nivolumab were measured by flow cytometry, and the PD-1 expression percentages (%) among CD8+ T cells were calculated.

The right panel in FIG. 9 shows the respective results of the same percentages calculated in the Responder group (7 patients) and the Non-Responder group (16 patients) (both groups were identified according to the same criteria as that in Example 8). Furthermore, the upper and lower limits of the 95% confidence interval were calculated based on the mean and standard deviation of the same percentages in the respective groups. Table 8 shows its results.

TABLE 8

|  | Mean ± S. D. | Upper Limit (95% Confidence Interval) | Lower Limit (95% Confidence Interval) |
|---|---|---|---|
| Responder Group | 72.5 ± 17.0 | 88.2 | 56.8 |
| Non-responder Group | 49.6 ± 16.3 | 58.3 | 40.9 |

As described above, in the case that the lower limit value 56.8 of the Responder group was set as the reference value, for example, a patient with gastric cancer exhibiting the PD-1 expression percentage which is the same value or more can be identified as a patient on which the effect of Nivolumab can be more expected.

The same patients with gastric cancer were divided into two groups, based on the median PD-1 expression ratio (55.8%). The lower panel in FIG. 10 shows the result of progression-free survival (PFS) calculated in the respective groups.

Example 10: Evaluation of Biomarkers for Determining the Effectiveness of Nivolumab, Based on the PD-1 Expression Percentage in Treg Cells (Fr. II) (Gastric Cancer: GC)

The number of PD-1-expressing Treg cells (Fr. II) derived from tumor tissues from 23 patients with gastric cancer prior to administration of Nivolumab were measured by flow cytometry, and the PD-1 expression percentages (%) among Treg cells (Fr. II) were calculated.

FIG. 11 shows the respective results of the same percentages calculated in the Responder group (7 patients) and the Non-Responder group (16 patients) (both groups were identified according to the same criteria as that in Example 8). Furthermore, the upper and lower limits of the 95% confidence interval were calculated based on the mean and standard deviation of the same percentages in the respective groups. Table 9 shows its results.

TABLE 9

|  | Mean ± SD | Upper Limit (95% Confidence Interval) | Lower Limit (95% Confidence Interval) |
| --- | --- | --- | --- |
| Responder Group | 38.1 ± 22.0 | 58.4 | 17.8 |
| Non-responder Group | 65.6 ± 14.1 | 73.1 | 58.1 |

As described above, in the case that the upper limit value 58.4 of the Responder group was set as the reference value, for example, a patient with gastric cancer exhibiting the PD-1 expression percentage which is less than the same value can be identified as a patient on which the effect of Nivolumab can be more expected.

The same patients with gastric cancer were divided into two groups, based on the median PD-1 expression ratio (62.3%). FIG. 12 shows the result of progression-free survival (PFS) calculated in the respective groups.

Example 11: Evaluation of a Biomarker for Determining the Effectiveness of Nivolumab, Based on the Respective PD-1 Expression Intensities in Treg Cells (Fr II) and $CD8^+$ T Cells (Non-Small Cell Lung Cancer)

The respective PD-1 expression intensities in Treg cells (Fr. II) and $CD8^+$ T cells derived from tumor tissues from 12 patients with non-small cell lung cancer prior to administration of Nivolumab were measured by flow cytometry, and the average fluorescence intensities (MFI) were calculated.

The left panel in FIG. 13 shows the results of the ratios of the PD-1 expression MFI in $CD8^+$ T cells to the PD-1 expression MFI in Treg cells (Fr. II), calculated in the Responder group (7 patients) and the Non-Responder group (5 patients) (both groups were identified according to the same criteria as that in Example 8), respectively. Furthermore, the upper and lower limits of the 95% confidence interval were calculated based on the mean and standard deviation of the same ratios in the respective groups. Table 10 shows its results.

TABLE 10

|  | Mean ± SD | Upper Limit (95% Confidence Interval) | Lower Limit (95% Confidence Interval) |
| --- | --- | --- | --- |
| Responder Group | 1.88 ± 0.34 | 2.19 | 1.57 |
| Non-responder Group | 0.87 ± 0.26 | 1.20 | 0.54 |

As described above, in the case that the upper limit value 1.20 of the Non-Responder group was set as the reference value, for example, a patient with non-small cell lung cancer exhibiting the ratio which is the same value or more can be identified as a patient on which the effect of Nivolumab can be more expected.

Example 12: Evaluation of a Biomarker for Determining the Effectiveness of Nivolumab, Based on the Respective PD-1 Expression Intensities in Treg Cells (Fr. II) and $CD8^+$ T Cells (Gastric Cancer)

The respective PD-1 expression intensities in Treg cells (Fr. II) and $CD8^+$ T cells derived from tumor tissues from 23 patients with gastric cancer prior to administration of Nivolumab were measured by flow cytometry, and the average fluorescence intensities (MFI) were calculated.

The right panel in FIG. 13 shows the respective results of the ratios of the PD-1 expression MFI in $CD8^+$ T cells to the PD-1 expression MFI in Treg cells (Fr. II), calculated in the Responder group (7 patients) and the Non-Responder group (16 patients) (both groups were identified according to the same criteria as that in Example 8). Furthermore, the upper and lower limits of the 95% confidence interval were calculated based on the mean and standard deviation of the same ratios in the respective groups. Table 11 shows its results.

TABLE 11

|  | Mean ± SD | Upper Limit (95% Confidence Interval) | Lower Limit (95% Confidence Interval) |
| --- | --- | --- | --- |
| Responder Group | 2.06 ± 0.91 | 2.90 | 1.22 |
| Non-responder Group | 0.78 ± 0.32 | 0.95 | 0.61 |

As described above, in the case that the upper limit value 0.95 of the Non-Responder group was set as the reference value, for example, a patient with gastric cancer exhibiting the ratio which is the same value or more can be identified as a patient on which the effect of Nivolumab can be more expected.

Example 13: Evaluation of a Biomarker for Determining the Effectiveness of Nivolumab, Based on the Respective PD-1 Expression Percentages (%) Among Treg Cells (Fr. II) and $CD8^+$ T Cells The PD-1 expression percentages (%) among $CD8^+$ T cells derived from the respective tumor tissues from the patients with non-small cell lung cancer (12 patients) and the patients with gastric cancer (23 patients), analyzed and calculated in Example 8 and 9, were plotted on horizontal axis, and the PD-1 expression percentages (%) among Treg cells (Fr. II) derived from the respective tumor tissues from the patient groups, analyzed and calculated according to Example 10, were plotted on vertical axis.

As shown in FIG. 14, it was confirmed that the Responder group and the Non-Responder group were selected by setting the condition that the PD-1 expression percentage (%) among $CD8^+$ T cells is 40% or more and a ratio of the PD-1 expression percentage (%) among $CD8^+$ T cells to the PD-1 expression percentage (%) among Treg cells (Fr. II) is 1.0 or more. Therefore, it was confirmed that a patient satisfying the same condition can be identified as a patient on which the effect of Nivolumab can be more expected.

Further, from analysis results shown in FIG. 15, it was confirmed that a patient in which the PD-1 expression percentage (%) among $CD8^+$ T cells is 40% or more and a ratio of the PD-1 expression MFI in $CD8^+$ T cells to the PD-1 expression MFI in Treg cells (Fr. II) is 1.0 or more can be identified as a patient on which the effect of Nivolumab can be more expected, as well.

The same patients with non-small cell lung cancer (12 patients) and the same patients with gastric cancer (23 patients) were divided into two groups consisting the patient group "Group R" satisfying the same condition and the patient group "The others" not satisfying that. FIG. 16 shows the result of progression-free survival (PFS) calculated in the respective groups.

Example 14: Evaluation of a Biomarker for Determining the Effectiveness of Nivolumab, Based on the Respective PD-1 Expression Intensities and the PD-1 Expression Percentages (%) of Treg Cells (Fr. II) and CD8$^+$ T Cells The respective PD-1 expression intensities in Treg cells (Fr. II) and CD8$^+$ T cells derived from tumor tissues from 13 patients with non-small cell lung cancer prior to administration of Nivolumab were measured by flow cytometry, and the average fluorescence intensities (MFI) were calculated. Further, the respective numbers of the PD-1-expressing CD8$^+$ T cells derived from the same tumor tissues were measured by flow cytometry, and the PD-1 expression percentage (%) among CD8$^+$ T cells were calculated. The change rates in tumor volume (%) were plotted on horizontal axis, and the numerical values calculated by multiplying ratios of the PD-1 expression intensity in the same CD8$^+$ T cells to the PD-1 expression intensity in the same Treg cells by the PD-1 expression percentages (%) among the same CD8$^+$ T cells were plotted on vertical axis. FIG. 17 shows its results. One of the 13 patients was excluded from the results because of missing data.

Furthermore, the upper and lower limits of the 95% confidence interval were calculated based on the mean and standard deviation of the same ratios in a group which the tumor volume was unchanged or reduced and the group in which the tumor volume increased. Table 12 shows its results.

TABLE 12

| N = 13 | Mean ± SD | Upper Limit 95% Confidence Interval | Lower Limit 95% Confidence Interval |
|---|---|---|---|
| Unchanged or reduced Group | 853.0 ± 997.7 | 2091.8 | −385.8 |
| Increased Group | 30.4 ± 18.6 | 46.0 | 14.9 |

As shown in FIG. 17, for example, it was confirmed that the group which the tumor volume was unchanged or reduced and the group in which the tumor volume increased were selected by setting the condition that the same numerical value is 60 or more (represented by a broken line) or the same numerical value is 46.0 or more (the upper limit of the 95% confidence interval of the group in which it increased), as shown in Table 12. Therefore, it was confirmed that a patient satisfying the same condition can be identified as a patient on which the effect of Nivolumab can be more expected.

Example 15: Evaluation of a Biomarker for Determining the Effectiveness of Nivolumab, Based on the Respective PD-1 Expression Percentages (%) in Treg Cells (Fr. II) and CD8$^+$ T Cells The respective numbers of PD-1-expressing Treg cells (Fr. II) and CD8$^+$ T cells derived from tumor tissues from 13 patients with non-small cell lung cancer prior to administration of Nivolumab were measured by flow cytometry, and the respective PD-1 expression percentages (%) among Treg cells (Fr. II) and CD8$^+$ T cells were calculated. The change rates in tumor volume (%) were plotted on horizontal axis, and the numerical values calculated by dividing the square of PD-1 expression percentages (%) among CD8$^+$ T cells by the PD-1 expression percentages (%) in Treg cells (Fr. II) were plotted on vertical axis. FIG. 18 shows its results.

Furthermore, the upper and lower limits of the 95% confidence interval were calculated based on the mean and standard deviation of the same ratios in a group which the tumor volume was unchanged or reduced and the group in which the tumor volume increased.

TABLE 13

| N = 12 | Mean ± SD | Upper Limit 95% Confidence Interval | Lower Limit 95% Confidence Interval |
|---|---|---|---|
| Unchanged or reduced Group | 163.8 ± 173.4 | 379.1 | −51.4 |
| Increased Group | 27.3 ± 18.5 | 44.4 | 10.2 |

As shown in FIG. 18, for example, it was confirmed that the group which the tumor volume was unchanged or reduced and the group in which the tumor volume increased were selected by setting the condition that the same numerical value is 60 or more (represented by a broken line) or the same numerical value is 44.4 or more (the upper limit of the 95% confidence interval of the group in which it increased), as shown in Table 13. Therefore, it was confirmed that a patient satisfying the same condition can be identified as a patient on which the effect of Nivolumab can be more expected.

Example 16: Evaluation of a Biomarker for Determining the Effectiveness of Nivolumab, Based on the Respective PD-1 Expression Percentages (%) in Treg Cells (Fr. II and CD8$^+$ T Cells Based on the respective PD-1 expression percentages (%) among Treg cells (Fr. II) and CD8$^+$ T cells derived from the respective tumor tissues from patients with non-small cell lung cancer (18 patients) and patients with gastric cancer (29 patients), the numerical values calculated by dividing the square of PD-1 expression percentages (%) among CD8$^+$ T cells by the PD-1 expression percentages (%) among Treg cells (Fr. II) were calculated, in the same manner as that in Example 15. FIG. 19 to 22 show the respective progression-free survival (PFS) after administration of Nivolumab in the reference value-positive group (a group having the respective reference value or more: BM+) and the negative group (a group having less than the respective reference value: BM−) in the case that the reference value (CUT) based on the same numerical value is 25, 40, 60, 90, or 100, for the same patients with non-small cell lung cancer and the same patients with gastric cancer. It was confirmed that in the evaluation of the progression-free survival, for the patients with non-small cell lung cancer, for example, a patient having the reference value of 40 or more can be identified as a patient on which the effect of Nivolumab can be more expected, while for the patients with gastric cancer, a patient having the reference value of 25 or more can be identified as a patient on which the effect of Nivolumab can be more expected.

Example 17: Evaluation of Biomarkers for Determining the Effectiveness of Nivolumab in Patients with Head and Neck Cancer The respective PD-1 expression intensities and PD-1 expression percentages (%) in Treg cells, Treg cells (Fr. II) and CD8$^+$ T cells derived from tumor tissues from 3 patients with head and neck cancer prior to administration of Nivolumab were measured by flow cytometry.

Table 14 shows the result (Response) of determination of the effectiveness after administration of Nivolumab to the same patients with head and neck cancer, the ratio referred to as Biomarker 1 of the present invention, the MFI value referred to as Biomarker 2 of the present invention, and the respective PD-1 expression percentages (%) referred to as Biomarker 3 and 4 of the present invention.

TABLE 14

|  | Response | Ratio A | Ratio B | Calculated Value C | Calculated Value D | Calculated Value E |
|---|---|---|---|---|---|---|
| Patient 1 | PD | 0.42 | 0.39 | 139 | 32.3 | 85.0 |
| Patient 2 | PR | 1.21 | 1.18 | 326 | 72.6 | 53.5 |
| Patient 3 | SD | 1.40 | 1.38 | 517 | 90.1 | 67.0 |

In the table, Ratio A represents the ratio referred to as Biomarker 1 (in the case of Treg cells) of the present invention, Ratio B represents the ratio referred to as Biomarker 1 (in the case of Treg cells (Fr. II)). Calculated Value C represents the MFI value referred to as Biomarker 2 of the present invention, and Calculated Values D and E represent the PD-1 expression percentages (%) referred to as Biomarker 3 and 4 of the present invention, respectively.

The left panel in FIG. 23 shows the results of the respective ratios referred to as Biomarker 1 of the present invention in Treg cells, for the Responder group (2 patients) and Non-Responder group (1 patient) (both groups is identified according to the same criteria as that in Example 8) among the patients with head and neck cancer, administered with Nivolumab, and the right panel shows the ratio referred to as Biomarker 1 in Treg cells (Fr. II). Further, the left panel and right panel in FIG. 24 show the respective PD-1 expression percentages (%) referred to as Biomarker 3 and Biomarker 4 in Treg cells (Fr. II) of the present invention, for the Responder group (2 patients) and Non-Responder group (1 patient) among the same patients with head and neck cancer, respectively.

Furthermore, FIG. 25 shows the respective numerical values referred to as Biomarker 6 of the present invention for the Responder group (2 patients) and Non-Responder group (1 patient) among the same patients with head and neck cancer, and FIG. 26 shows the respective numerical values referred to as Biomarker 7 (based on the PD-1 expression percentages (%) in Treg cells (Fr. II)) of the present invention for the Responder group (2 patients) and Non-Responder group (1 patient) among the same patients with head and neck cancer.

Furthermore, FIG. 27 shows the result that the PD-1 expression percentages (%) in $CD8^+$ T cells derived from tumor tissues from the same patients with head and neck cancer (3 patients), analyzed and calculated above, were plotted on horizontal axis and the PD-1 expression percentages (%) in Treg cells (Fr. II) derived from tumor tissues from the same patients were plotted on vertical axis.

Example 18: Calculation of the Ratio Referred to as Biomarker 1 of the Present Invention, Based on the MESF Value The respective PD-1 expression intensities in Treg cells, Treg cells (Fr. II) and $CD8^+$ T cells derived from tumor tissues from patients with non-small cell lung cancer (2 patients), a patient with head and neck cancer (1 patient) and a patient with colorectal cancer (1 patient) were measured by flow cytometry, and the average fluorescence intensities (MFI) were calculated. Further, a calibration curve for quantifying antigen molecule was prepared by a known measurement method using fluorescently labeled beads, and Molecules of Equivalent Soluble Fluorochrome (MESF), which is the number of cell surface antigen molecule-expressing cells (expression amount) determined from "PD-1 expression intensity" of the same biomarker, were calculated. Table 15 shows the MESF values and the ratios referred to as Biomarker 1 of the present invention, based on the same MESF values.

TABLE 15

|  | MFI | | | MESF | | |
|---|---|---|---|---|---|---|
|  | Calculated Value A | Calculated Value B | Ratio A | Calculated Value C | Calculated Value D | Ratio B |
| Patient 1 with Non-small cell lung cancer | 714 | 667 | 0.93 | 40064 | 37600 | 0.94 |
| Patient 2 with Non-small cell lung cancer | 458 | 728 | 1.59 | 26104 | 40137 | 1.54 |
| Patient with head and neck cancer | 551 | 1273 | 2.31 | 31694 | 68827 | 2.17 |
| Patient with colorectal cancer | 560 | 2204 | 3.94 | 36571 | 138800 | 3.80 |

In the table, Calculated Value A indicates the PD-1 expression intensity (MFI) in Treg cells (Fr. II), and Calculated Value B indicates the PD-1 expression intensity (MFI) in $CD8^+$ T cells. Calculated Value C indicates the number of PD-1-expressing Treg cells (Fr. II) (expression amount), and Calculated Value D indicates the number of PD-1-expressing $CD8^+$ T cells (expression amount). Ratio A indicates the ratio of Calculated Value B to Calculated Value A, and Ratio B indicates the ratio of Calculated Value D to Calculated Value C. In calculating the ratio referred to as Biomarker 1, it was confirmed that the MESF value can be used instead of the PD-1 expression MFI.

INDUSTRIAL APPLICABILITY

According to the present invention, by evaluating the ratio of the respective PD-1 expression intensities in Treg cells and $CD8^+$ T cells from tumor tissues or blood, patients with malignant tumor on which the effects of immune checkpoint inhibitors can be more expected can be identified.

The invention claimed is:

1. A method for suppressing progression of, suppressing recurrence of, and/or treating malignant tumor, comprising:
   obtaining a tumor tissue sample from a patient with malignant tumor;
   detecting amounts of a PD-1 expression intensity in CD8$^+$ T cells and a PD-1 expression intensity in Treg cells in the tumor tissue sample;
   identifying that the patient has a ratio of the PD-1 expression intensity in CD8$^+$ T cells to the PD-1 expression intensity in Treg cells in the tumor tissue of 0.7 or more; and
   administering an effective amount of an agent containing a substance inhibiting an immune checkpoint as an active ingredient, to the patient in need thereof, identified as having the ratio of 0.7 or more.

2. The method according to claim 1, wherein the ratio of the PD-1 expression intensity in CD8$^+$ T cells to the PD-1 expression intensity in Treg cells in the tumor tissue is 1.2 or more.

3. The method according to claim 1, wherein the ratio of the PD-1 expression intensity in CD8$^+$ T cells to the PD-1 expression intensity in Treg cells in the tumor tissue is 1.5 or more.

4. A method for suppressing progression of, suppressing recurrence of, and/or treating malignant tumor, comprising:
   obtaining a tumor tissue sample from a patient with malignant tumor;
   identifying that the patient satisfies at least one of criterion (a1) or (a2) and criterion (b); and
   administering an effective amount of an agent containing a substance inhibiting an immune checkpoint as an active ingredient, to the patient in need thereof, identified as satisfying at least one of the criterion (a1) or (a2) and criterion (b)
   wherein the criteria (a1), (a2) and (b) are as follow:
   (a1) a ratio of a PD-1 expression intensity in CD8$^+$ T cells in tumor tissue from the patient to a PD-1 expression intensity in Treg cells in the same tumor tissue is 0.8 or more,
   (a2) a ratio of a percentage (%) of the number of PD-1-expressing cells among the same CD8$^+$ T cells to a percentage (%) of the number of PD-1-expressing cells among the same Treg cells is 0.8 or more, and
   (b) a percentage (%) of the number of PD-1-expressing cells among the same CD8$^+$ T cells is 35% or more.

5. The method according to claim 4, wherein the ratio described in at least one of (a1) or (a2) is 0.9 or more.

6. The method according to claim 4, wherein the ratio described in at least one of (a1) or (a2) is 1.0 or more.

7. The method according to claim 4, wherein the ratio described in at least one of (a1) or (a2) is 1.1 or more.

8. The method according to claim 4, wherein the percentage described in (b) is 40% or more.

9. A method for suppressing progression of, suppressing recurrence of, and/or treating malignant tumor, comprising:
   obtaining a tumor tissue sample from a patient with malignant tumor;
   identifying that the patient satisfies criterion (a); and
   administering an effective amount of an agent containing a substance inhibiting an immune checkpoint as an active ingredient, to the patient in need thereof, identified as satisfying the criterion (a),
   wherein the criterion (a) is a numerical value calculated by multiplying a ratio of a PD-1 expression intensity in CD8$^+$ T cells in tumor tissue from the patient to a PD-1 expression intensity in Treg cells in the same tumor tissue by a percentage (%) of the number of PD-1-expressing cells among the same CD8$^+$ T cells is 25 or more.

10. A method for suppressing progression of, suppressing recurrence of, and/or treating malignant tumor, comprising:
    obtaining a tumor tissue sample from a patient with malignant tumor;
    identifying that the patient satisfies criterion (a); and
    administering an effective amount of an agent containing a substance inhibiting an immune checkpoint as an active ingredient, to the patient within need thereof, identified as satisfying the criterion (a)
    wherein the criterion (a) is a numerical value calculated by dividing a square of a percentage (%) of a number of PD-1-expressing cells among CD8$^+$ T cells in tumor tissue from the patient by a percentage (%) of a number of PD-1-expressing cells among Treg cells in the same tissue is 25 or more.

11. The method according to claim 9 or 10, wherein the numerical value is 60 or more.

12. The method according to claim 1, 4, 9, or 10, wherein the Treg cells are Treg cells Fr. II.

13. The method according to claim 1, 4, 9, or 10, wherein the patient with malignant tumor is a patient who is prior to administration of a drug containing the substance inhibiting an immune checkpoint.

14. The method according to claim 1, 4, 9, or 10, wherein the substance inhibiting an immune checkpoint is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody, or CSF-1R inhibitor.

15. The method according to claim 14, wherein the anti-PD-1 antibody is Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI754091, LZM009, CMAB819, Sym021, GB226, SSI-361, JY034, HX008, ISU106, ABBV181, BCD-100, PF-06801591, CX-188, or JNJ-63723283.

16. The method according to claim 1, 4, 9, or 10, wherein the malignant tumor is solid cancer or blood cancer.

17. The method according to claim 16, wherein the solid cancer is one or more cancers selected from malignant melanoma, non-small cell lung cancer, small cell lung cancer, head and neck cancer, renal cell carcinoma, clear cell renal cell carcinoma, breast cancer, ovarian cancer, serous ovarian cancer, clear cell carcinoma of the ovary, nasopharyngeal cancer, uterine cancer, anal cancer, colorectal cancer, rectum cancer, colon cancer, hepatocellular carcinoma, esophageal cancer, esophageal adenocarcinoma, gastric cancer, esophagogastric junction cancer, small intestine cancer, pancreatic cancer, urothelial cancer, prostate cancer, fallopian tube cancer, primary peritoneal cancer, malignant pleural mesothelioma, gallbladder cancer, bile duct cancer, biliary tract cancer, skin cancer, testicular cancer, vaginal cancer, vulvar cancer, penile cancer, small intestine cancer, endocrine cancer, thyroid cancer, parathyroid cancer, adrenal cancer, spinal tumor, brain tumor, squamous cell carcinoma, bone/soft tissue sarcomas and Kaposi's sarcoma.

18. The method according to claim 1, 4, 9, or 10, wherein the patient with malignant tumor has not been treated with any other anti-neoplastic agents.

19. The method according to claim 1, wherein the ratio described in claim 1 is 1.0 or more.

* * * * *

UNITED STATES PATENT AND TRADEMARK OFFICE
CERTIFICATE OF CORRECTION

PATENT NO. : 12,240,903 B2
APPLICATION NO. : 17/058794
DATED : March 4, 2025
INVENTOR(S) : Hiroyoshi Nishikawa et al.

Page 1 of 1

It is certified that error appears in the above-identified patent and that said Letters Patent is hereby corrected as shown below:

On the Title Page

Page 2, Column 2, Line 26, Other Publications, after "201980036678.6.", insert --¶Communication dated Nov. 8, 2024 from the Intellectual Property Office of Singapore in Application No. 11202011651S.--

Signed and Sealed this
Twenty-ninth Day of July, 2025

Coke Morgan Stewart
*Acting Director of the United States Patent and Trademark Office*